US009120776B2

(12) United States Patent
Yamamoto et al.

(10) Patent No.: US 9,120,776 B2
(45) Date of Patent: Sep. 1, 2015

(54) CONDENSED HETEROCYCLIC COMPOUND

(71) Applicant: Takeda Pharmaceutical Company Limited, Osaka-shi, Osaka (JP)

(72) Inventors: Satoshi Yamamoto, Kanagawa (JP); Junya Shirai, Kanagawa (JP); Yoshiyuki Fukase, Kanagawa (JP); Yoshihide Tomata, Kanagawa (JP); Ayumu Sato, Kanagawa (JP); Atsuko Ochida, Kanagawa (JP); Kazuko Yonemori, Kanagawa (JP); Hideyuki Nakagawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/346,071

(22) PCT Filed: Sep. 21, 2012

(86) PCT No.: PCT/JP2012/074282

§ 371 (c)(1),
(2) Date: Mar. 20, 2014

(87) PCT Pub. No.: WO2013/042782

PCT Pub. Date: Mar. 28, 2013

(65) Prior Publication Data

US 2014/0228409 A1 Aug. 14, 2014

(30) Foreign Application Priority Data

Sep. 22, 2011 (JP) ................................ 2011-207358

(51) Int. Cl.

*A61K 31/403* (2006.01)
*A61K 31/404* (2006.01)
*C07D 401/12* (2006.01)
*C07D 209/88* (2006.01)
*C07D 209/08* (2006.01)

(52) U.S. Cl.

CPC ............ *C07D 401/12* (2013.01); *A61K 31/403* (2013.01); *A61K 31/404* (2013.01); *C07D 209/08* (2013.01); *C07D 209/88* (2013.01)

(58) Field of Classification Search

USPC ........ 514/339, 411, 415; 546/276.7; 548/444, 548/503

See application file for complete search history.

(56) References Cited

U.S. PATENT DOCUMENTS

| | | | |
|---|---|---|---|
| 4,977,153 | A | 12/1990 | Louis et al. |
| 6,080,767 | A | 6/2000 | Klein et al. |
| 6,140,504 | A | 10/2000 | Klein et al. |
| 6,277,865 | B1 | 8/2001 | Klein et al. |
| 6,323,227 | B1 | 11/2001 | Klein et al. |
| 2002/0016339 | A1 | 2/2002 | Klein et al. |
| 2003/0171309 | A1 | 9/2003 | Halazy et al. |
| 2003/0212012 | A1 | 11/2003 | Halazy et al. |
| 2004/0067988 | A1 | 4/2004 | Klein et al. |
| 2004/0102634 | A1 | 5/2004 | Matsuura et al. |
| 2006/0247307 | A1 | 11/2006 | Kitahara et al. |
| 2006/0264486 | A1 | 11/2006 | Ma et al. |
| 2008/0167318 | A1 | 7/2008 | Halazy et al. |
| 2008/0176904 | A1 | 7/2008 | Govek et al. |
| 2008/0221157 | A1 | 9/2008 | Chakravarty et al. |
| 2009/0163511 | A1 | 6/2009 | Darwish et al. |
| 2009/0253758 | A1 | 10/2009 | Miller |
| 2009/0275609 | A1 | 11/2009 | Yu et al. |
| 2009/0298854 | A1 | 12/2009 | Ma et al. |
| 2010/0041721 | A1 | 2/2010 | Miller |
| 2011/0059958 | A1 | 3/2011 | Nishida et al. |
| 2011/0135650 | A1 | 6/2011 | Chackalamannil et al. |
| 2011/0224267 | A1 | 9/2011 | Miller |
| 2011/0245222 | A1 | 10/2011 | Payan et al. |
| 2011/0263046 | A1 | 10/2011 | Deuschle et al. |
| 2011/0319412 | A1 | 12/2011 | Sakagami et al. |
| 2012/0108606 | A1 | 5/2012 | Darwish et al. |
| 2013/0023660 | A1 | 1/2013 | Yu et al. |

(Continued)

FOREIGN PATENT DOCUMENTS

| | | |
|---|---|---|
| JP | 2003-529584 | 10/2003 |
| WO | 86/06717 | 11/1986 |

(Continued)

OTHER PUBLICATIONS

Registry STN Database accession No. 736964-37-7, Sep. 2004—1 page.

(Continued)

*Primary Examiner* — Kristin Vajda

(74) *Attorney, Agent, or Firm* — Hamre, Schumann, Mueller & Larson, P.C.

(57) ABSTRACT

The present invention provides a fused heterocyclic compound having an RORγt inhibitory action. The present invention relates to a compound represented by the formula (I'):

(I')

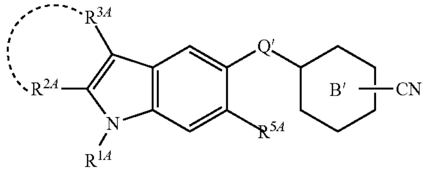

wherein each symbol is as defined in the specification, provided that 2-(2-((4-cyanophenyl)amino)-2-oxoethoxy)-N-(9-ethyl-9H-carbazol-3-yl)acetamide and N-(4-cyanophenyl)-N'-(9-ethyl-9H-carbazol-3-yl)-3-methylpentanediamide are excluded, or a thereof.

12 Claims, 3 Drawing Sheets

(56) References Cited

U.S. PATENT DOCUMENTS

| | | | |
|---|---|---|---|
| 2013/0116288 | A1 | 5/2013 | Miller |
| 2013/0211075 | A1 | 8/2013 | Ushio et al. |
| 2014/0045882 | A1 | 2/2014 | Darwish et al. |

FOREIGN PATENT DOCUMENTS

| | | |
|---|---|---|
| WO | 97/24118 | 7/1997 |
| WO | 99/00356 | 1/1999 |
| WO | 01/72705 | 10/2001 |
| WO | 01/74769 | 10/2001 |
| WO | 02/100812 | 12/2002 |
| WO | 2004/074236 | 9/2004 |
| WO | 2004/098498 | 11/2004 |
| WO | 2006/005941 | 1/2006 |
| WO | 2006/091496 | 8/2006 |
| WO | 2009/076631 | 6/2009 |
| WO | 2010/049144 | 5/2010 |
| WO | 2010/065717 | 6/2010 |
| WO | 2010/101246 | 9/2010 |
| WO | 2011/123681 | 10/2011 |
| WO | 2012/050159 | 4/2012 |

OTHER PUBLICATIONS

Registry STN Database accession No. 737780-18-6, Sep. 2004—1 page.

Ivanov, et al., "The orphan Nuclear Receptor RORγt Directs the Differentiation Program of Proinflammatory IL-17$^+$ T Helper Cells", Cell, vol. 126, Sep. 2006, pp. 1121-1133.

Manel, et al., "The differentiation of human $T_H$-17 cells requires transforming growth factor-β and induction of the nuclear receptor RORγt", Nature Immunology, vol. 9, No. 6, Jun. 2008, pp. 641-649.

Solt, et al., "Suppression of $T_H$17 differentiation and autoimmunity by a synthetic ROR ligand", Nature, vol. 472, Apr. 2011, p. 491.

Kumar, et al., "The Benzenesulfoamide T0901317 [*N*-2,2,2 -Trifluoroethyl]-*N*-[4-[2,2,2-trifluoro-1-hydroxy-1-(trifluoromethypethyl)ethnyl]phenyl]-benzenesulfonamide] Is a Novel Retinoic Acid Receptor-Related Orphan Receptor-α/γ Inverse Agonist", Mol. Pharmacol., vol. 77, No. 2, 2010, pp. 228-236.

Huh, et al., "Digoxin and its derivatives suppress $T_H$17 cell differentiation by antagonizing RORγt activity", Nature, vol. 472, Apr. 2011, pp. 486-490.

Wang, et al., "Identification of SR1078, a Synthetic Agonist for the Orphan Nuclear Receptors RORα and RORγ", ACS Chemical Biology, vol. 5, No. 11, pp. 1029-1034, 2010.

Xu, et al., "Ursolic Acid Suppresses Interleukin-17 (IL-17) Production by Selectively Antagonizing the Function of RORγt Protein", The Journal of Biological Chemistry, vol. 286, 2011, pp. 22707-22710.

Wang, et al., "Modulation of Retinoic Acid Receptor-related Orphan Receptor α and γ Activity by 7-Oxygenated Sterol Ligands", The Journal of Biological Chemistry, vol. 285, 2010, pp. 5013-5025.

Wang, et al., "A second class of nuclear receptors for oxysterols: Regulation of RORα and RORγ activity by 24*S*-hydroxycholesterol (cerebrosterol)", Biochimica et Biophysica Acta, vol. 1801, 2010, pp. 917-923.

Jin, et al., "Structural Basis for Hydroxycholesterols as Natural Ligands of Orphan Nuclear receptor RORγ", Mol. Endocrinol, vol. 24, No. 5, 2010, pp. 923-929.

Registry STN Database accession No. 1036688-95-5, Jul. 2008—1 page.

Registry STN Database accession No. 1327387-55-2, Sep. 2011—1 page.

Registry STN Database accession No. 1036676-51-3, Jul. 2008—1 page.

Registry STN Database accession No. 1015722-56-1, Apr. 2008—1 page.

Registry STN Database accession No. 745025-44-9, Sep. 2004—1 page.

Registry STN Database accession No. 568539-93-5, Aug. 2003—1 page.

n=6, mean±SE ##:p<0.01 vs normal; student's t test,
*:p<0.025 vs control;
William's test n=6, mean±SE ##:p<0.01 vs normal; student's t test,
*:p<0.025 vs control;
William's test n=6, means ± SE

CONDENSED HETEROCYCLIC COMPOUND

TECHNICAL FIELD

The present invention relates to a fused heterocyclic compound having an RORγt inhibitory action, a medicament containing the compound, and the like.

BACKGROUND OF THE INVENTION

Th17 cell and inflammatory cytokine (IL-17A, IL-17F and the like) produced thereby cause various autoimmune disease such as inflammatory bowel disease (IBD), rheumatoid arthritis, multiple sclerosis or psoriasis, and a decrease in QOL as a severe etiology cell and factor accompanying enhancement of a systemic new immune response. However, the existing therapeutic drugs show only limited effects, and therefore, the earliest possible development of a novel therapeutic drug has been desired.

Involvement of T cells, inter alia, Th17 cell and inflammatory cytokines (IL-17A, IL-17F and the like) produced thereby, in the pathology of these autoimmune disease has been drawing attention in recent years.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation (non-patent documents 1 and 2).

Therefore, a medicament that inhibits the action of RORγt is expected to show a treatment effect on various autoimmune disease by suppressing differentiation and activation of Th17 cells.

As a compound that regulates RORγ activity, patent document 1 describes a compound represented by the formula:

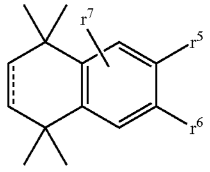

wherein r5 and r6 may together form

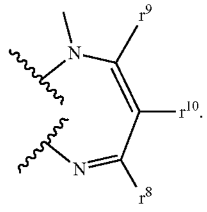

As a compound having an RORα and RORγ inverse agonist activity, non-patent document 3 describes a compound represented by the formula:

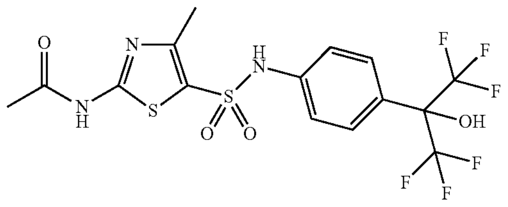 [SMILES: CC(=O)Nc1nc(C)c(S(=O)(=O)Nc2ccc(C(O)(C(F)(F)F)C(F)(F)F)cc2)s1]

(SR1001)

and non-patent document 4 describes a compound represented by the formula:

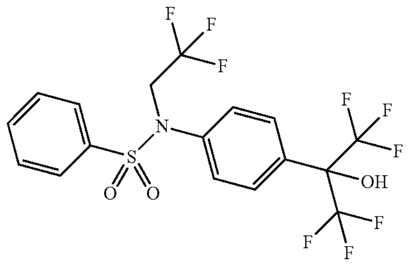 [SMILES: O=S(=O)(c1ccccc1)N(CC(F)(F)F)c1ccc(C(O)(C(F)(F)F)C(F)(F)F)cc1]

(TO901317).

As a compound that antagonizes an RORγt activity, non-patent document 5 describes a compound represented by the formula:

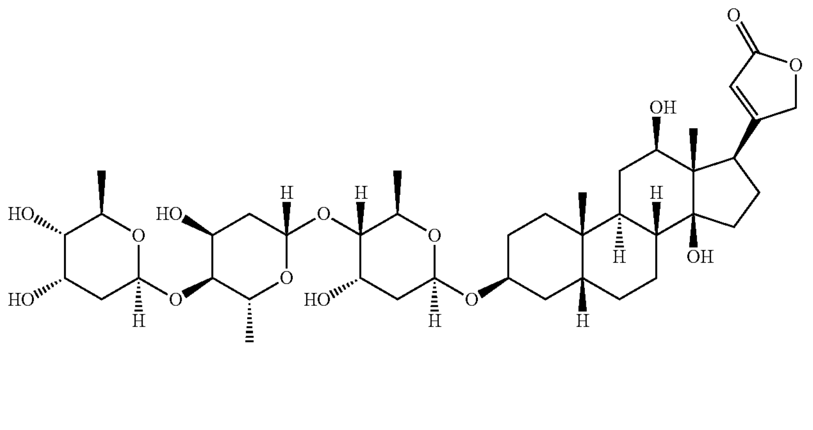

(Digoxin).

As a compound having an RORα and RORγ agonist activity, non-patent document 6' describes a compound represented by the formula:

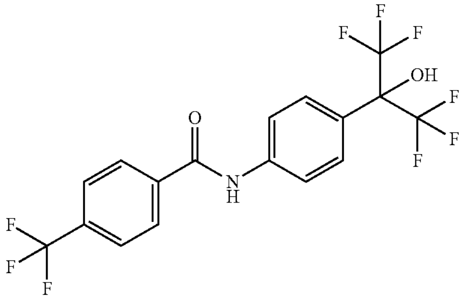 [SMILES: O=C(Nc1ccc(C(O)(C(F)(F)F)C(F)(F)F)cc1)c1ccc(C(F)(F)F)cc1]

(SR1078).

As a compound that regulates RORα and RORγ activities, non-patent document 7 describes a compound represented by the formula:

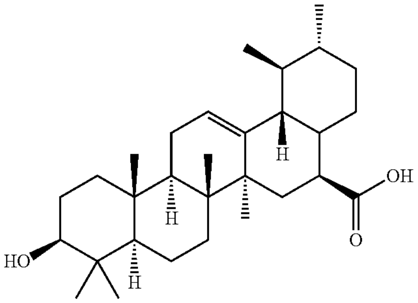

(Ursolic acid).

As a compound that regulates RORα and RORγ activities, non-patent document 8 describes compounds represented by the formulas:

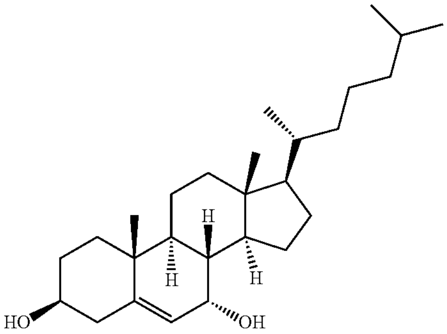

(7α-hydroxycholesterol)

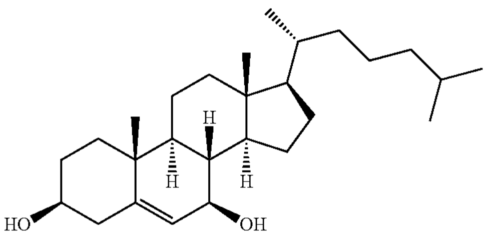

(7β-hydroxycholesterol)

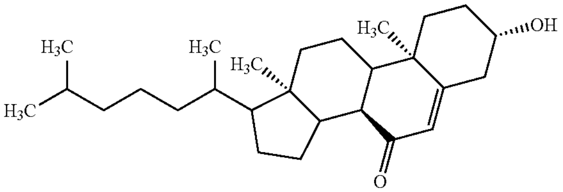

(24-ketocholesterol), and non-patent document 9 describes a compound represented by the formula:

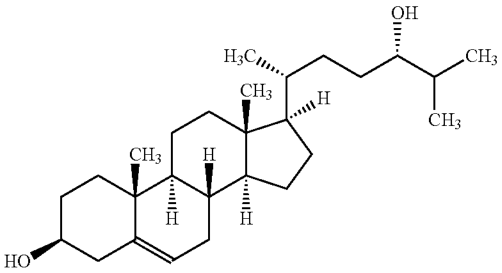

(24S-hydroxycholesterol).

As a ligand of RORγ, non-patent document 10 describes compounds represented by the formulas:

A

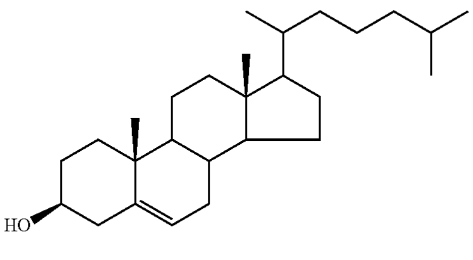

Cholesterol

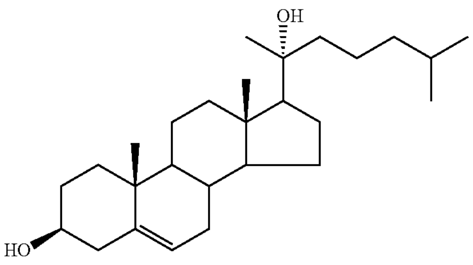

20α-Hydroxycholesterol

-continued

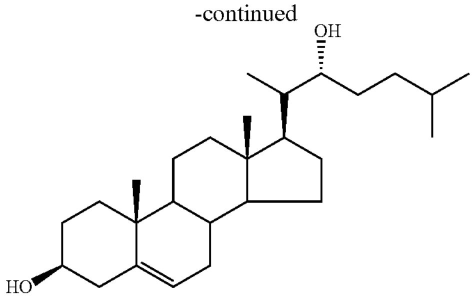

22(R)-Hydroxycholesterol

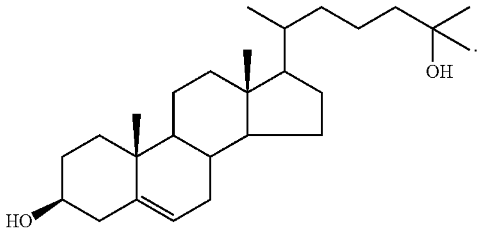

25-Hydroxycholesterol

DOCUMENT LIST

Patent Document patent document 1: WO 2010/049144

Non-Patent Document non-patent document 1: Cell 126, 1121-1133 (2006)
non-patent document 2: Nat. Immunol. 9, 641-649 (2008)
non-patent document 3: Nature, 2011, 472, 491
non-patent document 4: Mol. Pharmacol., 2010, 77(2): 228
non-patent document 5: Nature, 2011, 472, 486
non-patent document 6: ACS Chem. Biol. 2010, 5(11), 1029
non-patent document 7: The Journal of Biological Chemistry, 2011, 286, 22707
non-patent document 8: The Journal of Biological Chemistry, 2010, 285, 5013
non-patent document 9: Biochimica et Biophysica Acta, 1801 (2010), 917
non-patent document 10: Mol. Endocrinol, May 2010, 24(5), 923

SUMMARY OF THE INVENTION

Problems to be Solved by the Invention

The present invention aims to provide a compound having a superior RORγt inhibitory action, and useful as an agent for the prophylaxis or treatment of inflammatory bowel disease (IBD), ulcerative colitis (UC), Crohn's disease (CD), rheumatoid arthritis, multiple sclerosis, psoriasis and the like.

Means of Solving the Problems

The present inventors have found that a compound represented by the following formula (I) and (I') or a salt thereof has a superior RORγt inhibitory action based on the specific chemical structure thereof and affords superior efficacy as an agent for the prophylaxis or treatment of inflammatory bowel disease (IBD), ulcerative colitis (UC), Crohn's disease (CD), rheumatoid arthritis, multiple sclerosis, psoriasis and the like. The present inventors have conducted intensive studies based on the finding and completed the present invention.

Accordingly, present invention relates to

[1] a Compound represented by the formula (I'):

(I')

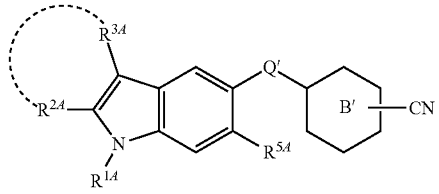

wherein $R^{1A}$ is an optionally substituted hydrocarbon group or an optionally substituted hydrocarbon-oxy group, $R^{2A}$ and $R^{3A}$ are each independently a hydrogen atom, an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^{2A}$ and $R^{3A}$ optionally form, together with the carbon atoms which they are bonded to, an optionally substituted hydrocarbon ring, $R^{5A}$ is a hydrogen atom or a halogen atom, Q' is a bivalent group selected from (I'a)

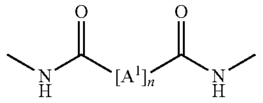

(I'b)

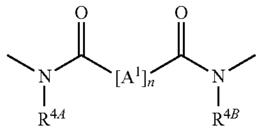

(I'c)

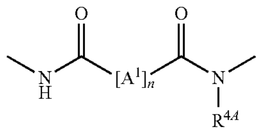

(I'd)

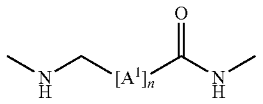

(I'e)

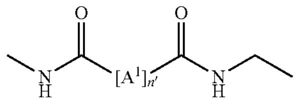

(I'f)

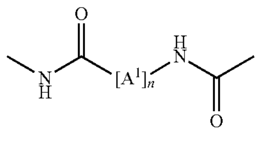

-continued (I'g)

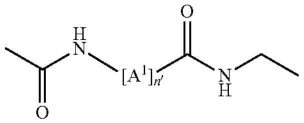

(I'h)

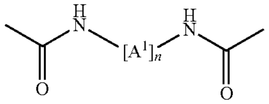

(I'i)

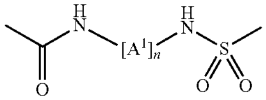

(I'j)

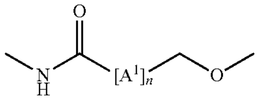

(I'k)

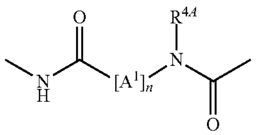

(I'l)

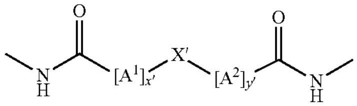

(I'm)

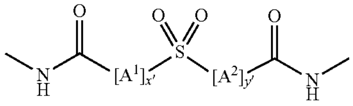

(I'n)

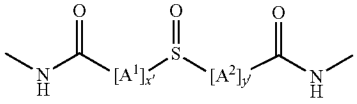

(I'o)

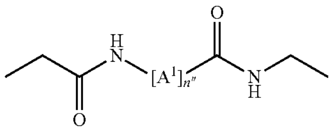

and (I'p)

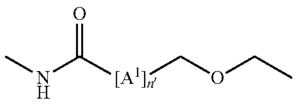

wherein

[$A^1$] are the same or different and each is a methylene group optionally substituted by substituent(s) selected from a hydroxy group, a phenyl group and an optionally substituted $C_{1-6}$ alkyl group, wherein the two substituents bonded to the single carbon atom are optionally combined to each other to form a hydrocarbon ring, and [$A^2$] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [$A^1$] or [$A^2$] is optionally combined to the substituent on the adjacent methylene group to form an optionally substituted hydrocarbon ring, $R^{4A}$ and $R^{4B}$ are the same or different and each is an optionally substituted hydrocarbon group, X' is an oxygen atom, a sulfur atom, or an imino group having an optionally substituted hydrocarbon group or a hydrogen atom, n is an integer of 1 to 5, n' is an integer of 1 to 4, n" is an integer of 1 to 3, and x' and y' are each 0 or natural number, and the sum is 0 to 4, and Ring B' is a benzene ring optionally having additional substituent(s), or a pyridine ring optionally having additional substituent(s), provided that when $R^{5A}$ is a halogen atom, then Ring B' is a benzene ring optionally having additional substituent(s), provided that 2-(2-((4-cyanophenyl)amino)-2-oxoethoxy)-N-(9-ethyl-9H-carbazol-3-yl)acetamide and N-(4-cyanophenyl)-N'-(9-ethyl-9H-carbazol-3-yl)-3-methylpentanediamide are excluded (hereinafter sometimes to be referred to as compound (I')) or a salt thereof;

[2] the compound or salt of [1], wherein $R^{5A}$ is a hydrogen atom,

Q' is a bivalent group selected from (I'a)

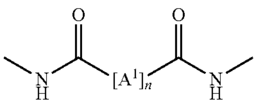

(I'b)

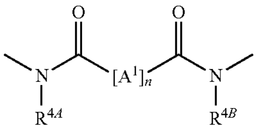

(I'c)

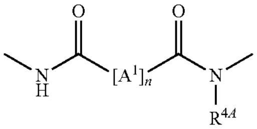

(I'd)

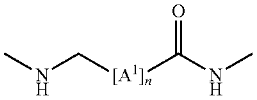

(I'e)

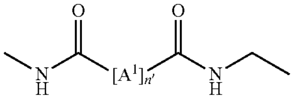

(I'f)

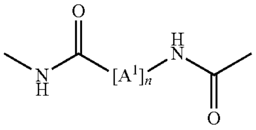

(I'g)

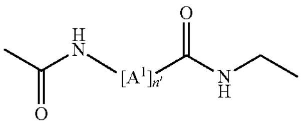

(I'h)

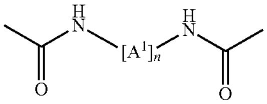

-continued (I'i)

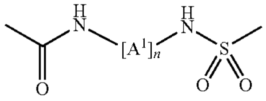

(I'j)

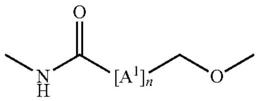

(I'k)

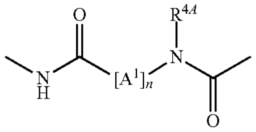

(I'l)

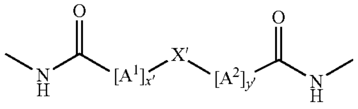

(I'm)

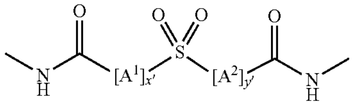

and (I'n)

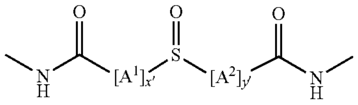

wherein $[A^1]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, and $[A^2]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in $[A^1]$ or $[A^2]$ is optionally combined to the substituent on the adjacent methylene group to form an optionally substituted hydrocarbon ring, and the other symbols are as defined in [1], and Ring B' is a benzene ring optionally further substituted by substituent(s) excluding cyano;

[3] the compound or salt of [1], wherein $R^{2A}$ and $R^{3A}$ are each independently a $C_{1-6}$ alkyl group, or $R^{2A}$ and $R^{3A}$ form, together with the carbon atoms which they are bonded to, an optionally substituted hydrocarbon ring;

[4] the compound or salt of [1], wherein Q' is a bivalent group selected from (I'a)

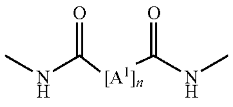

-continued (I'f)

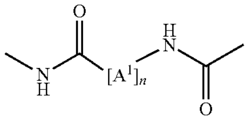

(I'j)

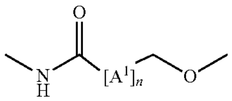

(I'l')

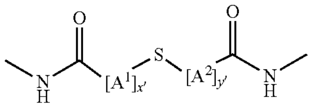

and (I'n)

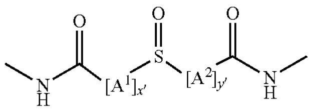

wherein each symbol is as defined in [1];

[5] N-(4-cyanophenyl)-N'-(9-ethyl-2,3,4,9-tetrahydro-1H-carbazol-6-yl)-3-methylpentanediamide or a salt thereof;

[6] N-(3-chloro-4-cyanophenyl)-N'-(9-ethyl-9H-carbazol-3-yl)-3-methylpentanediamide or a salt thereof;

[7] N-{4-[(3-chloro-4-cyanophenyl)amino]-2-methyl-4-oxobutyl}-9-ethyl-9H-carbazole-3-carboxamide or a salt thereof;

[8] a medicament comprising a compound represented by the formula (I'):

(I')

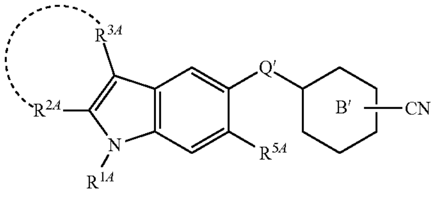

wherein $R^{1A}$ is an optionally substituted hydrocarbon group or an optionally substituted hydrocarbon-oxy group, $R^{2A}$ and $R^{3A}$ are each independently a hydrogen atom, an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^{2A}$ and $R^{3A}$ optionally form, together with the carbon atoms which they are bonded to, an optionally substituted hydrocarbon ring, $R^{5A}$ is a hydrogen atom or a halogen atom, Q' is a bivalent group selected from (I'a)

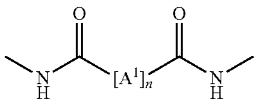

-continued (I'b)

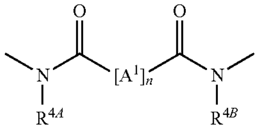

(I'c)

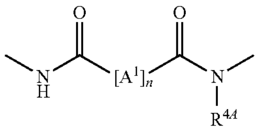

(I'd)

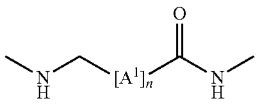

(I'e)

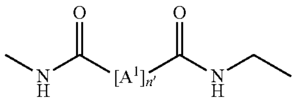

(I'f)

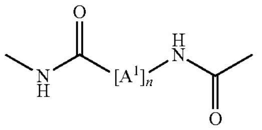

(I'g)

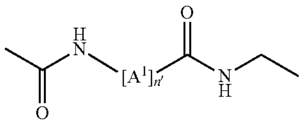

(I'h)

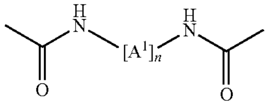

(I'i)

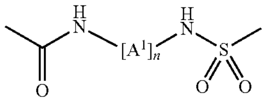

(I'j)

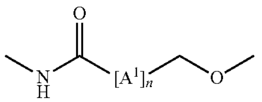

(I'k)

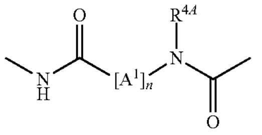

(I'l)

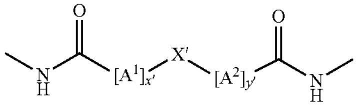

(I'm)

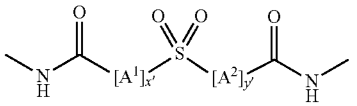

-continued (I'n)

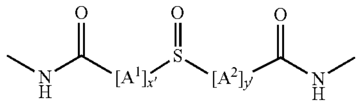

(I'o)

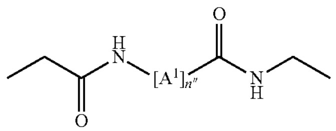

and (I'p)

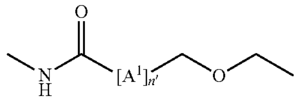

wherein

[$A^1$] are the same or different and each is a methylene group optionally substituted by substituent(s) selected from a hydroxy group, a phenyl group and an optionally substituted $C_{1-6}$ alkyl group, wherein the two substituents bonded to the single carbon atom are optionally combined to each other to form a hydrocarbon ring, and [$A^2$] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [$A^1$] or [$A^2$] is optionally combined to the substituent on the adjacent methylene group to form an optionally substituted hydrocarbon ring, $R^{4A}$ and $R^{4B}$ are the same or different and each is an optionally substituted hydrocarbon group, X' is an oxygen atom, a sulfur atom, or an imino group having an optionally substituted hydrocarbon group or a hydrogen atom, n is an integer of 1 to 5, n' is an integer of 1 to 4, n" is an integer of 1 to 3, and x' and y' are each 0 or natural number, and the sum is 0 to 4, and Ring B' is a benzene ring optionally having additional substituent(s), or a pyridine ring optionally having additional substituent(s), provided that when $R^{5A}$ is a halogen atom, then Ring B' is a benzene ring optionally having additional substituent(s), or a salt thereof;

[9] the medicament of [8], which is an RORγt inhibitor;

[10] the medicament of [8], which is an agent for the prophylaxis or treatment of inflammatory bowel disease (IBD), ulcerative colitis (UC), Crohn's disease (CD), rheumatoid arthritis, multiple sclerosis or psoriasis;

[11] a method of inhibiting RORγt, which comprises administering an effective amount of the compound or salt of [1] to a mammal;

[12] a method for the prophylaxis or treatment of inflammatory bowel disease (IBD), ulcerative colitis (UC), Crohn's disease (CD), rheumatoid arthritis, multiple sclerosis or psoriasis, which comprises administering an effective amount of the compound or salt of [1] to a mammal;

[13] use of the compound or salt of [1] for the production of an agent for the prophylaxis or treatment of inflammatory bowel disease (IBD), ulcerative colitis (UC), Crohn's disease (CD), rheumatoid arthritis, multiple sclerosis or psoriasis;

[14] the compound or salt of [1] for use in the prophylaxis or treatment of inflammatory bowel disease (IBD), ulcerative colitis (UC), Crohn's disease (CD), rheumatoid arthritis, multiple sclerosis or psoriasis; and the like.

The present invention also relates to

[1A] a compound represented by the formula (I):

(I)

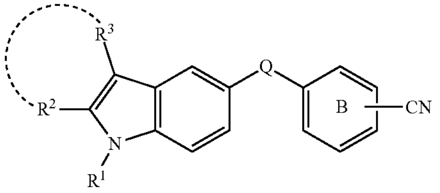

wherein $R^1$ is an optionally substituted hydrocarbon group or an optionally substituted hydrocarbon-oxy group, $R^2$ and $R^3$ are each independently an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^2$ and $R^3$ optionally form, together with the carbon atoms which they are bonded to, an optionally substituted hydrocarbon ring, Q is a bivalent group selected from (Ia)

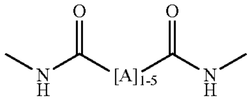

(Ib)

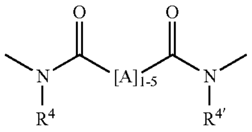

(Ic)

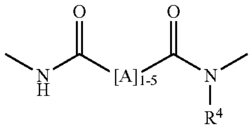

(Id)

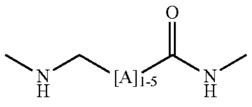

(Ie)

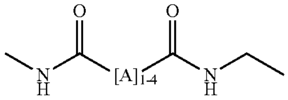

(If)

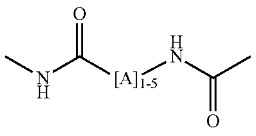

-continued (Ig)

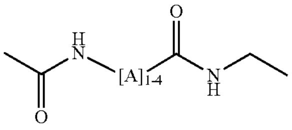

(Ih)

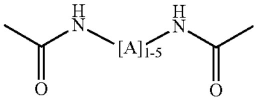

(Ii)

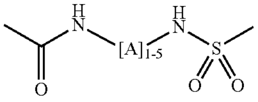

(Ij)

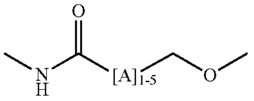

(Ik)

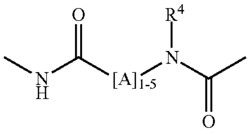

(Il)

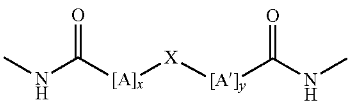

(Im)

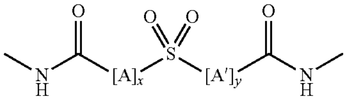

and (In)

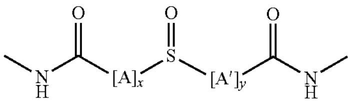

wherein

[A] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, and [A'] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [A] or [A'] is optionally combined to the substituent on the adjacent methylene group to form an optionally substituted hydrocarbon ring, $R^4$ and $R^{4'}$ are the same or different and each is an optionally substituted hydrocarbon group, X is an oxygen atom, a sulfur atom, or an imino group having an optionally substituted hydrocarbon group or a hydrogen atom, and x and y are each 0 or natural number, and the sum is 0 to 4, and Ring B is a benzene ring optionally further substituted by substituent(s) excluding cyano, provided that 2-(2-((4-cyanophenyl)amino)-2-oxoethoxy)-N-(9-ethyl-9H-carbazol-3-yl)acetamide and N-(4-cyanophenyl)-N'-(9-ethyl-9H-carbazol-3-yl)-3-methylpentanediamide are excluded (hereinafter sometimes to be referred to as compound (I)) or a salt thereof;

[2A] the compound or salt of [1A], wherein $R^2$ and $R^3$ are each independently a $C_{1-6}$ alkyl group, or $R^2$ and $R^3$ form, together with the carbon atoms which they are bonded to, an optionally substituted hydrocarbon ring;

[3A] the compound or salt of [1A], wherein Q is (Ia)

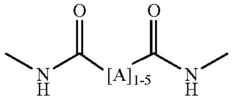

(Ij)

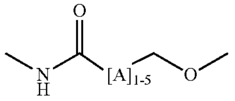

(Il')

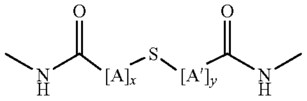

or (In)

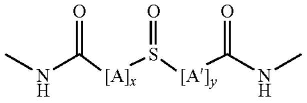

wherein [A], [A'], x and y are as defined in [1A];

[4A] a medicament comprising a compound represented by the formula (I):

(I)

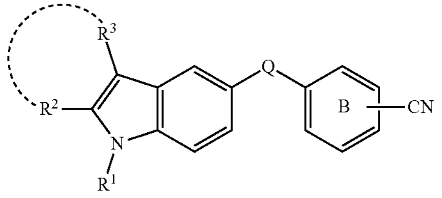

wherein $R^1$ is an optionally substituted hydrocarbon group or an optionally substituted hydrocarbon-oxy group, $R^2$ and $R^3$ are each independently an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^2$ and $R^3$ optionally form, together with the carbon atoms which they are bonded to, an optionally substituted hydrocarbon ring, Q is a bivalent group selected from (Ia)

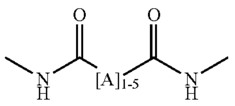

-continued (Ib)

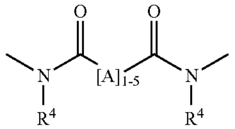

(Ic)

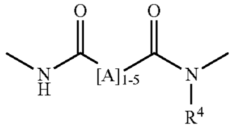

(Id)

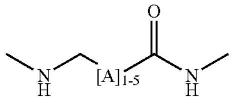

(Ie)

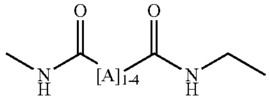

(If)

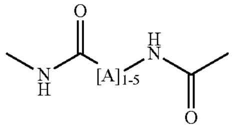

(Ig)

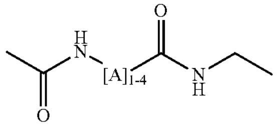

(Ih)

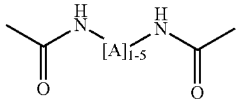

(Ii)

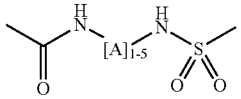

(Ij)

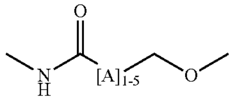

(Ik)

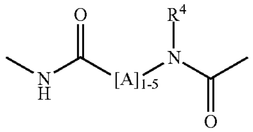

(Il)

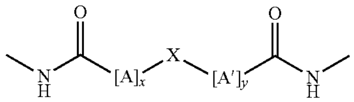

(Im)

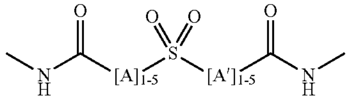

and

-continued (In)

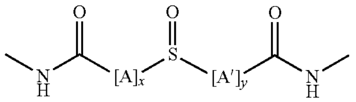

wherein

[A] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, and [A'] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [A] or [A'] is optionally combined to the substituent on the adjacent methylene group to form an optionally substituted hydrocarbon ring, $R^4$ and $R^{4'}$ are the same or different and each is an optionally substituted hydrocarbon group, X is an oxygen atom, a sulfur atom, or an imino group having an optionally substituted hydrocarbon group or a hydrogen atom, and x and y are each 0 or natural number, and the sum is 0 to 4, and Ring B is a benzene ring optionally further substituted by substituent(s) excluding cyano, or a salt thereof;

[5A] the medicament of [4A], which is a RORγt receptor inhibitor.

[6A] the medicament of [4A], which is an agent for the prophylaxis or treatment of inflammatory bowel disease (IBD), Crohn's disease (CD), rheumatoid arthritis, multiple sclerosis or psoriasis;

and the like.

Effect of the Invention

The compound of the present invention has a superior RORγt inhibitory action, and useful as an agent for the prophylaxis or treatment of inflammatory bowel disease (IBD), ulcerative colitis (UC), Crohn's disease (CD), rheumatoid arthritis, multiple sclerosis, psoriasis and the like.

DETAILED DESCRIPTION OF THE INVENTION

Figure 1:
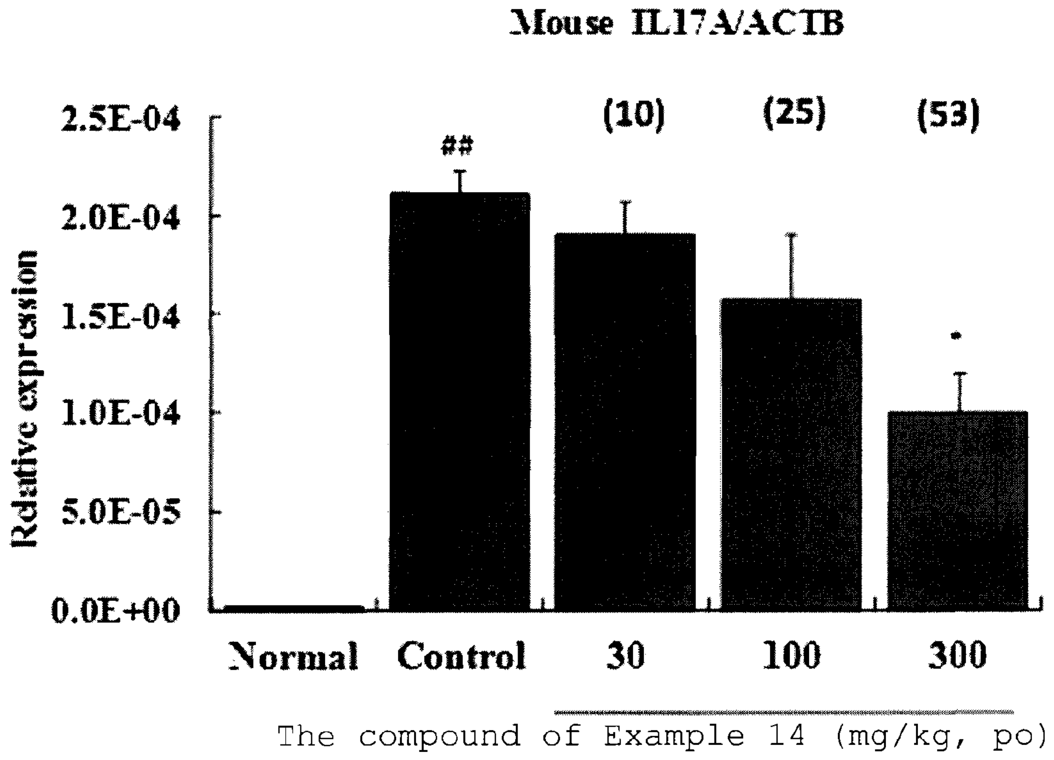
FIG. 1 shows an effect of the compound of Example 14 on IL-17A gene expression caused by stimulation with anti-CD3 antibody in mouse colon.

The present invention is explained in detail in the following.

In the present specification, examples of the "optionally substituted hydrocarbon group" include an optionally substituted alkyl group, an optionally substituted alkenyl group, an optionally substituted alkynyl group, an optionally substituted aralkyl group, an optionally substituted aryl group, an optionally substituted cycloalkyl group, an optionally substituted cycloalkenyl group and the like.

In the present specification, examples of the "optionally substituted alkyl group" include a $C_{1-6}$ alkyl group (e.g., methyl, ethyl, propyl, isopropyl, butyl, isobutyl, sec-butyl, tert-butyl, pentyl, neo-pentyl, hexyl etc.) optionally having substituent(s) selected from (i) a halogen atom (e.g., a fluorine atom, a chlorine atom, a bromine atom, an iodine atom), (ii) a cyano group, (iii) a hydroxyl group, (iv) a nitro group, (v) a formyl group, (vi) an amino group, (vii) a mono- or di-$C_{1-6}$ alkylamino group (e.g., methylamino, ethylamino, propylamino, dimethylamino, diethylamino, dipropylamino etc.), (viii) a $C_{1-6}$ alkyl-carbonylamino group (e.g., acetylamino, ethylcarbonylamino etc.), (ix) a $C_{1-6}$ alkoxy-carbonylamino group (e.g., methoxycarbonylamino, ethoxycarbonylamino, propoxycarbonylamino etc.), (x) a $C_{3-8}$ cycloalkyl group (e.g., cyclopropyl, cyclobutyl, cyclopentyl, cyclohexyl etc.) optionally fused with a benzene ring, (xi) a $C_{3-8}$ cycloalkenyl group (e.g., cyclopropenyl, cyclobutenyl, cyclopentenyl, cyclohexenyl etc.) optionally fused with a benzene ring, (xii) a $C_{6-14}$ aryl group (e.g., phenyl, 1-naphthyl, 2-naphthyl etc.) optionally substituted by substituent(s) selected from a halogen atom (e.g., a fluorine atom, a chlorine atom, a bromine atom, an iodine atom) and a $C_{1-6}$ alkoxy group (e.g., methoxy, ethoxy, propoxy etc.), (xiii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., a fluorine atom, a chlorine atom, a bromine atom, an iodine atom), (xiv) a $C_{7-16}$ aralkyloxy group (e.g., benzyloxy etc.), (xv) a $C_{6-14}$ aryloxy group (e.g., phenoxy etc.) optionally substituted by substituent(s) selected from a $C_{1-6}$ alkoxy group (e.g., methoxy etc.), a $C_{1-6}$ alkyl group (e.g., methyl etc.) and a halogen atom (e.g., a fluorine atom, a chlorine atom, a bromine atom, an iodine atom), (xvi) a carboxyl group, (xvii) a $C_{1-6}$ alkoxy-carbonyl group (e.g., methoxycarbonyl, ethoxycarbonyl, propoxycarbonyl, isopropoxycarbonyl, tert-butoxycarbonyl etc.), (xviii) a $C_{7-16}$ aralkyloxy-carbonyl group (e.g., benzyloxycarbonyl etc.), (xix) a $C_{6-14}$ aryloxy-carbonyl group (e.g., phenoxycarbonyl etc.), (xx) a $C_{1-6}$ alkyl-carbonyl group (e.g., acetyl, ethylcarbonyl, propylcarbonyl, isopropylcarbonyl, 2,2-dimethylpropylcarbonyl etc.), (xxi) a $C_{3-8}$ cycloalkyl-carbonyl group (e.g., cyclopropylcarbonyl, cyclobutylcarbonyl, cyclopentylcarbonyl, cyclohexylcarbonyl etc.), (xxii) a $C_{7-16}$ aralkyl-carbonyl group (e.g., benzylcarbonyl etc.), (xxvii) a carbamoyl group, (xxiv) a thiocarbamoyl group, (xxv) a mono- or di-$C_{1-6}$ alkyl-carbamoyl group (e.g., methylcarbamoyl, ethylcarbamoyl, propylcarbamoyl, isopropylcarbamoyl, dimethylcarbamoyl, diethylcarbamoyl, dipropylcarbamoyl etc.), (xxvi) a mono- or di-$C_{7-16}$ aralkyl-carbamoyl group (e.g., benzylcarbamoyl, dibenzylcarbamoyl etc.), (xxvii) a thiol group,
(xxviii) a $C_{1-6}$ alkylthio group (e.g., methylthio, ethylthio, propylthio etc.),
(xxix) a $C_{7-16}$ aralkylthio group (e.g., benzylthio etc.),
(xxx) a $C_{1-6}$ alkylsulfonyl group (e.g., methylsulfonyl, ethylsulfonyl, propylsulfonyl, isopropylsulfonyl etc.),
(xxxi) a $C_{3-8}$ cycloalkylsulfonyl group (e.g., cyclopropylsulfonyl, cyclobutylsulfonyl, cyclopentylsulfonyl etc.),
(xxxii) a $C_{6-14}$ arylsulfonyl group (e.g., phenylsulfonyl, 1-naphthylsulfonyl, 2-naphthylsulfonyl etc.),
(xxxiii) a $C_{7-16}$ aralkylsulfonyl group (e.g., benzylsulfonyl etc.),
(xxxiv) a 5- to 8-membered non-aromatic heterocyclic group containing, besides carbon atoms, 1 to 4 hetero atoms selected from a nitrogen atom, a sulfur atom and an oxygen atom (e.g., pyrrolidinyl, tetrahydrofuryl, tetrahydrothienyl, piperidyl, tetrahydropyranyl, morpholinyl, thiomorpholinyl, piperazinyl etc.), wherein the non-aromatic heterocyclic group is optionally substituted by $C_{1-6}$ alkyl group(s) (e.g., methyl etc.),
(xxxv) a 5- to 8-membered aromatic heterocyclic group containing, besides carbon atoms, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), wherein the aromatic heterocyclic group is optionally substituted by halogen atom(s) (e.g., a chlorine atom etc.) or $C_{1-6}$ alkyl group(s) (e.g., methyl etc.) and optionally fused with a benzene ring (e.g., benzothienyl etc.),
(xxxvi) a 5- to 8-membered non-aromatic heterocyclyl-carbonyl group containing, besides carbon atoms, 1 to 4 hetero atoms selected from a nitrogen atom, a sulfur atom and an oxygen atom (e.g., pyrrolidinylcarbonyl, tetrahydrofurylcarbonyl, tetrahydrothienylcarbonyl, piperidylcarbonyl, tetrahydropyranylcarbonyl, morpholinylcarbonyl, thiomorpholinylcarbonyl, piperazinylcarbonyl etc.),
(xxxvii) a 5- to 8-membered aromatic heterocyclyl-carbonyl group containing, besides carbon atoms, 1 to 4 hetero atoms selected from a nitrogen atom, a sulfur atom and an oxygen atom (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyrazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, 1,2,3-triazolylcarbonyl, 1,2,4-triazolylcarbonyl, tetrazolylcarbonyl, pyridylcarbonyl, pyridazinylcarbonyl, pyrimidinylcarbonyl, pyrazinylcarbonyl, triazinylcarbonyl etc.),
(xxxviii) an ureido group,
(xxxix) a $C_{1-6}$ alkyl-ureido group (e.g., methylureido, ethylureido, propylureido etc.),
(xxxx) a $C_{6-14}$ aryl-ureido group (e.g., phenylureido, 1-naphthylureido, 2-naphthylureido etc.),
(xxxxi) a $C_{1-4}$ alkylenedioxy group (e.g., methylenedioxy, ethylenedioxy, propylenedioxy etc.),
(xxxxii) an aminosulfonyl group,
(xxxxiii) a mono-N—$C_{1-6}$ alkylaminosulfonyl group (e.g., methylaminosulfonyl, ethylaminosulfonyl etc.),
(xxxxiv) a di-N,N—$C_{1-6}$ alkylaminosulfonyl group (e.g., dimethylaminosulfonyl, diethylaminosulfonyl etc.),
(xxxxv) a bridged $C_{7-10}$ cycloalkyl group (e.g., bicyclo[3.1.1]heptyl, adamantyl etc.) optionally substituted by $C_{1-6}$ alkyl group(s) (e.g., methyl etc.),
(xxxxvi) a $C_{6-14}$ arylthio group (e.g., phenylthio etc.) and the like. The number of the substituents is 1 to 4, preferably 1 to 3. When the number of the substituents is 2 or more, the respective substituents may be the same or different.

In the present specification, examples of the "optionally substituted alkenyl group" include a $C_{2-6}$ alkenyl group (e.g., vinyl, 1-propenyl, allyl, isopropenyl, butenyl, isobutenyl etc.) optionally having 1 to 4, preferably 1 to 3, substituents which the alkyl group of the above-defined "optionally substituted alkyl group" optionally has, and the like. When the number of the substituents is 2 or more, the respective substituents may be the same or different.

In the present specification, examples of the "optionally substituted alkynyl group" include a $C_{2-6}$ alkynyl group (e.g., ethynyl, propargyl, butynyl, 1-hexynyl etc.) optionally having 1 to 4, preferably 1 to 3, substituents which the alkyl group of the above-defined "optionally substituted alkyl group" optionally has, and the like. When the number of the substituents is 2 or more, the respective substituents may be the same or different.

In the present specification, examples of the "optionally substituted aralkyl group" include a $C_{7-12}$ aralkyl group (e.g., benzyl, 2-phenylethyl, 1-phenylethyl, 3-phenylpropyl and the like) optionally having 1 to 4, preferably 1 to 3,
(i) substituents which the alkyl group of the above-defined "optionally substituted alkyl group" optionally has,
(ii) $C_{1-6}$ alkyl groups (e.g., methyl, ethyl, propyl, isopropyl, butyl, isobutyl, sec-butyl, tert-butyl, pentyl, neo-pentyl, hexyl and the like) optionally substituted by substituent(s) selected from a halogen atom (e.g., a fluorine atom, a chlorine atom, a bromine atom, an iodine atom), a $C_{1-6}$ alkoxy group (e.g., methoxy, ethoxy, propoxy and the like), a $C_{6-14}$ arylsulfonyl group and a heterocyclic group (e.g., morpholinyl, pyridyl, imidazopyridyl, benzimidazolyl and the like),
(iii) $C_{7-16}$ aralkyl groups (e.g., benzyl, 2-phenylethyl, 1-phenylethyl, 3-phenylpropyl, 4-phenylbutyl and the like),
(iv) 5- to 8-membered aromatic heterocyclyl-oxy groups containing, besides carbon atoms, 1 to 4 hetero atoms selected from a nitrogen atom, a sulfur atom and an oxygen atom (e.g., furyloxy, thienyloxy, pyrrolyloxy, oxazolyloxy, isoxazolyloxy, thiazolyloxy, isothiazolyloxy, imidazolyloxy, pyrazolyloxy, 1,2,3-oxadiazolyloxy, 1,2,4-oxadiazolyloxy, 1,3,4-oxadiazolyloxy, furazanyloxy, 1,2,3-thiadiazolyloxy, 1,2,4-thiadiazolyloxy, 1,3,4-thiadiazolyloxy, 1,2,3-triazolyloxy, 1,2,4-triazolyloxy, tetrazolyloxy, pyridyloxy, pyridazinyloxy, pyrimidinyloxy, pyrazinyloxy, triazinyloxy and the like), or the like. In the present specification, the substituent of the "optionally substituted aralkyl group" may be present in the aryl part and/or the alkylene part of the aralkyl group. When the number of the substituents is 2 or more, the respective substituents may be the same or different.

In the present specification, examples of the "optionally substituted aryl group" include a $C_{6-14}$ aryl group (e.g., phenyl, naphthyl and the like) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "optionally substituted cycloalkyl group" include a $C_{3-8}$ cycloalkyl group (e.g., cyclopropyl, cyclobutyl, cyclopentyl, cyclohexyl) optionally having 1 to 4, preferably 1 to 3, substituents which the aralkyl group of the above-defined "optionally substituted aralkyl group" optionally has. When the number of the substituents is 2 or more, the respective substituents may be the same or different. Meanwhile, the substituents for "optionally substituted cycloalkyl group" are optionally bonded to form a ring (a cycloalkane ring (a $C_{3-6}$ cycloalkane ring such as a cyclopropane ring, a cyclobutane ring, a cyclopentane ring, a cyclohexane ring), an arene ring (a $C_{6-10}$ arene ring such as a benzene ring, a naphthalene ring)).

In the present specification, examples of the "optionally substituted cycloalkenyl group" include $C_{3-8}$ cycloalkenyl group (e.g., cyclopropenyl, cyclobutenyl, cyclopentenyl, cyclohexenyl and the like) optionally having 1 to 4, preferably 1 to 3, substituents which the aralkyl group of the above-defined "optionally substituted aralkyl group" optionally has. When the number of the substituents is 2 or more, the respective substituents may be the same or different. Meanwhile, the substituents for the "optionally substituted cycloalkenyl group" are optionally bonded to form a ring (a cycloalkane ring (a $C_{3-6}$ cycloalkane ring such as a cyclopropane ring, a cyclobutane ring, a cyclopentane ring and a cyclohexane ring), an arene ring (a $C_{6-10}$ arene ring such as a benzene ring and a naphthalene ring)).

In the present specification, examples of the "optionally, substituted hydrocarbon-oxy group" include a hydrocarbon-oxy group wherein the optionally substituted hydrocarbon moiety is the above-defined "optionally substituted hydrocarbon group".

In the present specification, examples of the "optionally substituted hydrocarbon-amino group" include an amino group optionally mono- or di-substituted by the above-defined "optionally substituted hydrocarbon group". When di-substituted, two "optionally substituted hydrocarbon groups" may be the same or different.

In the present specification, examples of the "optionally substituted hydrocarbon-sulfanyl group" include a hydrocarbon-sulfanyl group wherein the optionally substituted hydrocarbon moiety is the above-defined "optionally substituted hydrocarbon group".

In the present specification, examples of the "optionally substituted hydrocarbon-sulfenyl group" include hydrocarbon-sulfenyl group wherein the optionally substituted hydrocarbon moiety is the above-defined "optionally substituted hydrocarbon group".

In the present specification, examples of the "optionally substituted hydrocarbon-sulfonyl group" include a hydrocarbon-sulfonyl group wherein the optionally substituted hydrocarbon moiety is the above-defined "optionally substituted hydrocarbon group".

In the present specification, examples of the "acyl group" include an "optionally substituted alkylcarbonyl group", an "optionally substituted alkenylcarbonyl group", an "optionally substituted alkynylcarbonyl group", an "optionally substituted aralkylcarbonyl group", an "optionally substituted arylcarbonyl group", an "optionally substituted cycloalkylcarbonyl group", an "optionally substituted alkoxycarbonyl group", an "optionally substituted alkenyloxycarbonyl group", an "optionally substituted alkynyloxycarbonyl group", an "optionally substituted aralkyloxycarbonyl group", an "optionally substituted aryloxycarbonyl group", an "optionally substituted cycloalkyloxycarbonyl group", a "carboxyl group" and the like.

In the present specification, examples of the "optionally substituted alkylcarbonyl group" include a $C_{1-6}$ alkyl-carbonyl group (e.g., methylcarbonyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl and the like) optionally having 1 to 4, preferably 1 to 3, substituents which the alkyl group of the above-defined "optionally substituted alkyl group" optionally has. When the number of the substituents is 2 or more, the respective substituents may be the same or different.

In the present specification, examples of the "optionally substituted alkenylcarbonyl group" include a $C_{2-6}$ alkenylcarbonyl group (e.g., vinylcarbonyl, 1-propenylcarbonyl, allylcarbonyl, isopropenylcarbonyl, butenylcarbonyl, isobutenylcarbonyl and the like) optionally having 1 to 4, preferably 1 to 3, substituents which the alkyl group of the above-defined "optionally substituted alkyl group" optionally has, and the like. When the number of the substituents is 2 or more, the respective substituents may be the same or different.

In the present specification, examples of the "optionally substituted alkynylcarbonyl group" include a $C_{2-6}$ alkynylcarbonyl group (e.g., ethynylcarbonyl, propargylcarbonyl, butynylcarbonyl, 1-hexynylcarbonyl and the like) optionally having 1 to 4, preferably 1 to 3, substituents which the alkyl group of the above-defined "optionally substituted alkyl group" optionally has, and the like. When the number of the substituents is 2 or more, the respective substituents may be the same or different.

In the present specification, examples of the "optionally substituted aralkylcarbonyl group" include a $C_{7-12}$ aralkylcarbonyl group (e.g., benzylcarbonyl, 2-phenylethylcarbonyl, 1-phenylethylcarbonyl, 3-phenylpropylcarbonyl and the like) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "optionally substituted arylcarbonyl group" include a $C_{6-14}$ aryl-carbonyl group (e.g., phenylcarbonyl, naphthylcarbonyl and the like) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "optionally substituted cycloalkylcarbonyl group" include a $C_{3-8}$ cycloalkyl-carbonyl group (e.g., cyclopropylcarbonyl, cyclobutylcarbonyl, cyclopentylcarbonyl, cyclohexylcarbonyl) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "optionally substituted alkoxycarbonyl group" include a $C_{1-6}$ alkoxycarbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like) optionally having 1 to 4, preferably 1 to 3, substituents which the alkyl group of the above-defined "optionally substituted alkyl group" optionally has. When the number of the substituents is 2 or more, the respective substituents may be the same or different.

In the present specification, examples of the "optionally substituted alkenyloxycarbonyl group" include a $C_{2-6}$ alkenyl-oxycarbonyl group (e.g., vinyloxycarbonyl, 1-propenyloxycarbonyl, allyloxycarbonyl, isopropenyloxycarbonyl, butenyloxycarbonyl, isobutenyloxycarbonyl and the like) optionally having 1 to 4, preferably 1 to 3, substituents which the alkyl group of the above-defined "optionally substituted alkyl group" optionally has, and the like. When the number of the substituents is 2 or more, the respective substituents may be the same or different.

In the present specification, examples of the "optionally substituted alkynyloxycarbonyl group" include a $C_{2-6}$ alkynyl-oxycarbonyl group (e.g., ethynyloxycarbonyl, propargyloxycarbonyl, butynyloxycarbonyl, 1-hexynyloxycarbonyl and the like) optionally having 1 to 4, preferably 1 to 3, substituents which the alkyl group of the above-defined "optionally substituted alkyl group" optionally has, and the like. When the number of the substituents is 2 or more, the respective substituents may be the same or different.

In the present specification, examples of the "optionally substituted aralkyloxycarbonyl group" include a $C_{7-12}$ aralkyl-oxycarbonyl group (e.g., benzyloxycarbonyl, 2-phenylethyloxycarbonyl, 1-phenylethyloxycarbonyl, 3-phenylpropyloxycarbonyl and the like) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "optionally substituted aryloxycarbonyl group" include a $C_{6-14}$ aryl-oxycarbonyl group (e.g., phenyloxycarbonyl, naphthyloxycarbonyl and the like) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "optionally substituted cycloalkyloxycarbonyl group" include a $C_{3-8}$ cycloalkyl-oxycarbonyl group (e.g., cyclopropyloxycarbonyl, cyclobutyloxycarbonyl, cyclopentyloxycarbonyl, cyclohexyloxycarbonyl) optionally having 1 to 4, preferably 1 to 3, substituents which the aralkyl group of the above-defined "optionally substituted aralkyl group" optionally has. When the number of the substituents is 2 or more, the respective substituents may be the same or different.

In the present specification, examples of the "halogen atom" include a fluorine atom, a chlorine atom, a bromine atom, and an iodine atom.

In the present specification, examples of the "optionally substituted hydrocarbon ring" include an "optionally substituted arene ring", an "optionally substituted cycloalkane ring", an "optionally substituted cycloalkene ring", corresponding to the above-defined "optionally substituted aryl group", "optionally substituted cycloalkyl group", "optionally substituted cycloalkenyl group", and the like.

Additionally, in the present specification, examples of the "hydrocarbon ring" include an "arene ring", a "cycloalkane ring", a "cycloalkene ring", corresponding to the "aryl group", the "cycloalkyl group", the "cycloalkenyl group", in the above-defined "optionally substituted aryl group", "optionally substituted cycloalkyl group", "optionally substituted cycloalkenyl group", and the like.

In the present specification, examples of the "substituent" of the "benzene ring optionally further substituted by substituent(s) excluding cyano" include a substituent which the aryl group of the above-defined "optionally substituted aryl group" optionally has, an optionally substituted hydrocarbon group and the like. The number of the substituents is preferably 1 to 4, more preferably 1 to 3, further more preferably 1 or 2. When the number of the substituents is 2 or more, the respective substituents may be the same or different.

In the present specification, examples of the "substituent" of the "benzene ring optionally having additional substituent(s)" and the "pyridine ring optionally having additional substituent(s)" include a substituent which the aryl group of the above-defined "optionally substituted aryl group" optionally has, an optionally substituted hydrocarbon group and the like. The number of the substituents is preferably 1 to 4, more preferably 1 to 3, further more preferably 1 or 2. When the number of the substituents is 2 or more, the respective substituents may be the same or different.

The definition of each symbol in the formula (I') is explained in detail in the following.

$R^{1A}$ is an optionally substituted hydrocarbon group or an optionally substituted hydrocarbon-oxy group.

The "optionally substituted hydrocarbon group" for $R^{1A}$ is preferably a $C_{1-6}$ alkyl group (e.g., methyl, ethyl, propyl, isopropyl, butyl, isobutyl, sec-butyl, tert-butyl, pentyl, neopentyl, hexyl etc.) optionally having substituent(s) selected from (i) a halogen atom (e.g., a fluorine atom, a chlorine atom, a bromine atom, an iodine atom),
(ii) a cyano group,
(iii) a hydroxyl group,
(iv) a nitro group,
(v) a formyl group,
(vi) an amino group,
(vii) a mono- or di-$C_{1-6}$ alkylamino group (e.g., methylamino, ethylamino, propylamino, dimethylamino, diethylamino, dipropylamino etc.),
(viii) a $C_{1-6}$ alkyl-carbonylamino group (e.g., acetylamino, ethylcarbonylamino etc.),
(ix) a $C_{1-6}$ alkoxy-carbonylamino group (e.g., methoxycarbonylamino, ethoxycarbonylamino, propoxycarbonylamino etc.),
(x) a $C_{3-8}$ cycloalkyl group (e.g., cyclopropyl, cyclobutyl, cyclopentyl, cyclohexyl etc.) optionally fused with a benzene ring,
(xi) a $C_{3-8}$ cycloalkenyl group (e.g., cyclopropenyl, cyclobutenyl, cyclopentenyl, cyclohexenyl etc.) optionally fused with a benzene ring,
(xii) a $C_{6-14}$ aryl group (e.g., phenyl, 1-naphthyl, 2-naphthyl etc.) optionally substituted by substituent(s) selected from a halogen atom (e.g., a fluorine atom, a chlorine atom, a bromine atom, an iodine atom) and a $C_{1-6}$ alkoxy group (e.g., methoxy, ethoxy, propoxy etc.),
(xiii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., a fluorine atom, a chlorine atom, a bromine atom, an iodine atom),
(xiv) a $C_{7-16}$ aralkyloxy group (e.g., benzyloxy etc.),
(xv) a $C_{6-14}$ aryloxy group (e.g., phenoxy etc.) optionally substituted by substituent(s) selected from a $C_{1-6}$ alkoxy group (e.g., methoxy etc.), a $C_{1-6}$ alkyl group (e.g., methyl etc.) and a halogen atom (e.g., a fluorine atom, a chlorine atom, a bromine atom, an iodine atom),
(xvi) a $C_{1-6}$ alkoxy-carbonyl group (e.g., methoxycarbonyl, ethoxycarbonyl, propoxycarbonyl, isopropoxycarbonyl, tert-butoxycarbonyl etc.),
(xvii) a $C_{7-16}$ aralkyloxy-carbonyl group (e.g., benzyloxycarbonyl etc.),
(xviii) a $C_{6-14}$ aryloxy-carbonyl group (e.g., phenoxycarbonyl etc.),
(xix) a $C_{1-6}$ alkyl-carbonyl group (e.g., acetyl, ethylcarbonyl, propylcarbonyl, isopropylcarbonyl, 2,2-dimethylpropylcarbonyl etc.),
(xx) a $C_{3-8}$ cycloalkyl-carbonyl group (e.g., cyclopropylcarbonyl, cyclobutylcarbonyl, cyclopentylcarbonyl, cyclohexylcarbonyl etc.),
(xxi) a $C_{7-16}$ aralkyl-carbonyl group (e.g., benzylcarbonyl etc.), (xxii) a carbamoyl group, (xxiii) a thiocarbamoyl group, (xxiv) a mono- or di-$C_{1-6}$ alkyl-carbamoyl group (e.g., methylcarbamoyl, ethylcarbamoyl, propylcarbamoyl, isopropylcarbamoyl, dimethylcarbamoyl, diethylcarbamoyl, dipropylcarbamoyl etc.), (xxv) a mono- or di-$C_{7-16}$ aralkyl-carbamoyl group (e.g., benzylcarbamoyl, dibenzylcarbamoyl etc.), (xxvi) a thiol group, (xxvii) a $C_{1-6}$ alkylthio group (e.g., methylthio, ethylthio, propylthio etc.), (xxiii) a $C_{7-16}$ aralkylthio group (e.g., benzylthio etc.), (xxix) a $C_{1-6}$ alkylsulfonyl group (e.g., methylsulfonyl, ethylsulfonyl, propylsulfonyl, isopropylsulfonyl etc.), (xxx) a $C_{3-8}$ cycloalkylsulfonyl group (e.g., cyclopropylsulfonyl, cyclobutylsulfonyl, cyclopentylsulfonyl etc.), (xxxi) a $C_{6-14}$ arylsulfonyl group (e.g., phenylsulfonyl, 1-naphthylsulfonyl, 2-naphthylsulfonyl etc.), (xxxii) a $C_{7-16}$ aralkylsulfonyl group (e.g., benzylsulfonyl etc.), (xxxiii) a 5- to 8-membered non-aromatic heterocyclic group containing, besides carbon atoms, 1 to 4 hetero atoms selected from a nitrogen atom, a sulfur atom and an oxygen atom (e.g., pyrrolidinyl, tetrahydrofuryl, tetrahydrothienyl, piperidyl, tetrahydropyranyl, morpholinyl, thiomorpholinyl, piperazinyl etc.), wherein the non-aromatic heterocyclic group is optionally substituted by $C_{1-6}$ alkyl group(s) (e.g., methyl etc.), (xxxiv) a 5- to 8-membered aromatic heterocyclic group containing, besides carbon atoms, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), wherein the aromatic heterocyclic group is optionally substituted by halogen atom(s) (e.g., a chlorine atom etc.) or $C_{1-6}$ alkyl group(s) (e.g., methyl etc.) and optionally fused with a benzene ring (e.g., benzothienyl etc.), (xxxv) a 5- to 8-membered non-aromatic heterocyclyl-carbonyl group containing, besides carbon atoms, 1 to 4 hetero atoms selected from a nitrogen atom, a sulfur atom and an oxygen atom (e.g., pyrrolidinylcarbonyl, tetrahydrofurylcarbonyl, tetrahydrothienylcarbonyl, piperidylcarbonyl, tetrahydropyranylcarbonyl, morpholinylcarbonyl, thiomorpholinylcarbonyl, piperazinylcarbonyl (xxxvi) a 5- to 8-membered aromatic heterocyclyl-carbonyl group containing, besides carbon atoms, 1 to 4 hetero atoms selected from a nitrogen atom, a sulfur atom and an oxygen atom (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyrazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, 1,2,3-triazolylcarbonyl, 1,2,4-triazolylcarbonyl, tetrazolylcarbonyl, pyridylcarbonyl, pyridazinylcarbonyl, pyrimidinylcarbonyl, pyrazinylcarbonyl, triazinylcarbonyl etc.), (xxxvii) an ureido group, (xxxviii) a $C_{1-6}$ alkyl-ureido group (e.g., methylureido, ethylureido, propylureido etc.), (xxxix) a $C_{6-14}$ aryl-ureido group (e.g., phenylureido, 1-naphthylureido, 2-naphthylureido etc.), (xxxx) a $C_{1-4}$ alkylenedioxy group (e.g., methylenedioxy, ethylenedioxy, propylenedioxy etc.), (xxxxi) an aminosulfonyl group, (xxxxii) a mono-N—$C_{1-6}$ alkylaminosulfonyl group (e.g., methylaminosulfonyl, ethylaminosulfonyl etc.), (xxxxiii) a di-N,N—$C_{1-6}$ alkylaminosulfonyl group (e.g., dimethylaminosulfonyl, diethylaminosulfonyl etc.), (xxxxiv) a bridged $C_{7-10}$ cycloalkyl group (e.g., bicyclo [3.1.1]heptyl, adamantyl etc.) optionally substituted by $C_{1-6}$ alkyl group(s) (e.g., methyl etc.), (xxxxv) a $C_{6-14}$ arylthio group (e.g., phenylthio etc.) and the like. The number of the substituents is 1 to 4, preferably 1 to 3. When the number of the substituents is 2 or more, the respective substituents may be the same or different.

$R^{1A}$ is preferably a $C_{1-6}$ alkyl group (e.g., methyl, ethyl, propyl, isobutyl) optionally substituted by substituent(s) selected from the above-mentioned (i)-(xxxxv), more preferably a $C_{1-6}$ alkyl group (e.g., methyl, ethyl, propyl, isobutyl), particularly preferably methyl, ethyl, propyl or isobutyl.

$R^{2A}$ and $R^{3A}$ are each independently a hydrogen atom, an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^{2A}$ and $R^{3A}$ optionally form, together with the carbon atoms which they are bonded to, an optionally substituted hydrocarbon ring.

The "optionally substituted hydrocarbon group" for $R^{2A}$ or $R^{3A}$ is preferably those similar to the preferable group as the "optionally substituted hydrocarbon group" for $R^{1A}$.

$R^{2A}$ and $R^{3A}$ are preferably each independently a hydrogen atom or an optionally substituted hydrocarbon group, more preferably a hydrogen atom, or a $C_{1-6}$ alkyl group (e.g., methyl) optionally substituted by substituent(s) selected from the above-mentioned (i)-(xxxxv) exemplified as the substituents which the "optionally substituted hydrocarbon group" for $R^{1A}$ optionally has, still more preferably a hydrogen atom or a $C_{1-6}$ alkyl group (e.g., methyl), particularly preferably a hydrogen atom or methyl.

Alternatively, $R^{2A}$ and $R^{3A}$ preferably form, together with the carbon atoms which they are bonded to, an optionally substituted arene ring (e.g., a benzene ring) or an optionally substituted cycloalkene ring (e.g., a cyclohexene ring), more preferably an arene ring (e.g., a benzene ring) or a cycloalkene ring (e.g., a cyclohexene ring), particularly preferably a benzene ring or a cyclohexene ring.

In another embodiment, preferably, $R^{2A}$ and $R^{3A}$ are each independently a $C_{1-6}$ alkyl group, or $R^{2A}$ and $R^{3A}$ form, together with the carbon atoms which they are bonded to, an optionally substituted hydrocarbon ring.

$R^{5A}$ is a hydrogen atom or a halogen atom.

$R^{5A}$ is preferably a hydrogen atom or a chlorine atom, more preferably a hydrogen atom.

Q' is a bivalent group selected from (I'a)

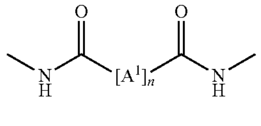

-continued (I'b)

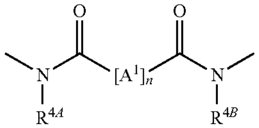

(I'c)

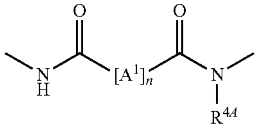

(I'd)

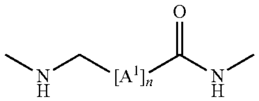

(I'e)

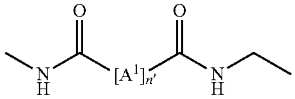

(I'f)

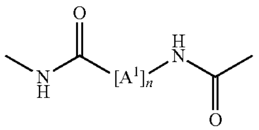

(I'g)

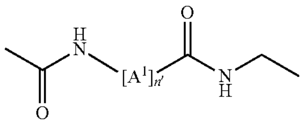

(I'h)

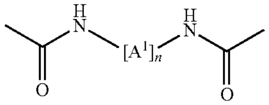

(I'i)

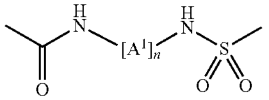

(I'j)

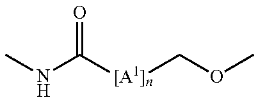

(I'k)

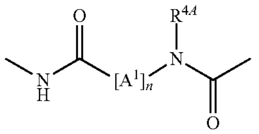

(I'l)

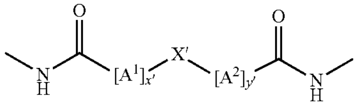

(I'm)

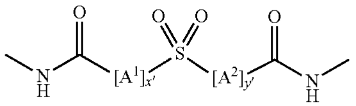

-continued (I'n)

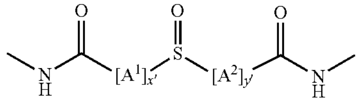

(I'o)

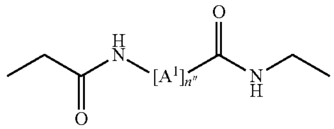

and (I'p)

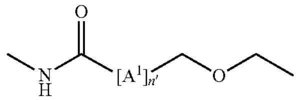

wherein

[$A^1$] are the same or different and each is a methylene group optionally substituted by substituent(s) selected from a hydroxy group, a phenyl group and an optionally substituted $C_{1-6}$ alkyl group, wherein the two substituents bonded to the single carbon atom are optionally combined to each other to form a hydrocarbon ring, and [$A^2$] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [$A^1$] or [$A^2$] is optionally combined to the substituent on the adjacent methylene group to form an optionally substituted hydrocarbon ring, $R^{4A}$ and $R^{4B}$ are the same or different and each is an optionally substituted hydrocarbon group, X' is an oxygen atom, a sulfur atom, or an imino group having an optionally substituted hydrocarbon group or a hydrogen atom, n is an integer of 1 to 5, n' is an integer of 1 to 4, n" is an integer of 1 to 3, and x' and y' are each 0 or natural number, and the sum is 0 to 4.

The "methylene group wherein the two substituents bonded to the single carbon atom are optionally combined to each other to form a hydrocarbon ring" in the above-mentioned definition of [$A^1$] or [$A^2$] means, for example, a methylene group represented by

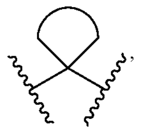 [SMILES: *C(*)(C)C]

and the "methylene group in [$A^1$] or [$A^2$] is optionally combined to the substituent on the adjacent methylene group to form an optionally substituted hydrocarbon ring" means, for example, a group represented by

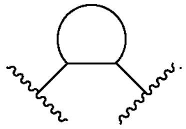 [SMILES: *CC*]

In formula (I'), of the two bonds of the bivalent group for Q', either the right bond or the left bond may be bonded to Ring B, preferably the right bond is bonded to Ring B.

Q' is preferably a bivalent group selected from (I'a)

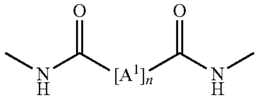

(I'b)

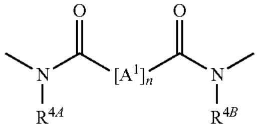

(I'c)

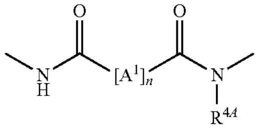

(I'd)

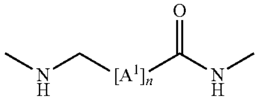

(I'e)

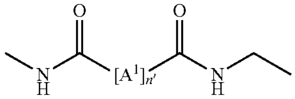

(I'f)

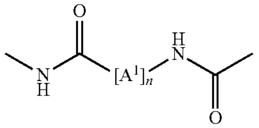

(I'g)

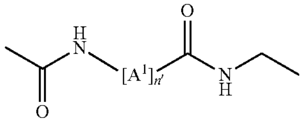

(I'h)

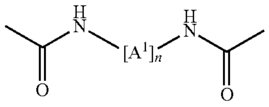

(I'i)

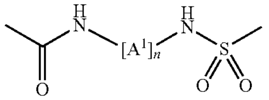

(I'j)

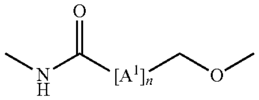

-continued (I'k)

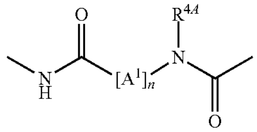

(I'l)

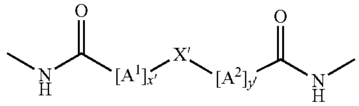

(I'm)

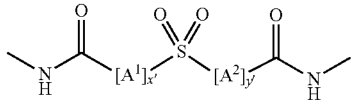

and (I'n)

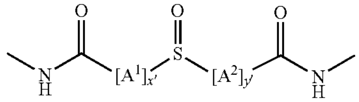

wherein $[A^1]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, and $[A^2]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in $[A^1]$ or $[A^2]$ is optionally combined to the substituent on the adjacent methylene group to form an optionally substituted hydrocarbon ring, and the other symbols are as defined above.

In another embodiment, Q' is preferably a bivalent group selected from (I'a)

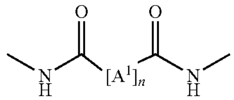

(I'f)

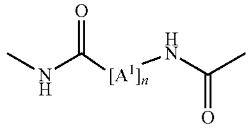

(I'j)

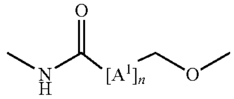

(I'l')

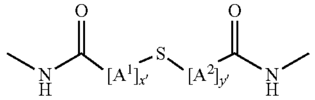

and

-continued (I'n)

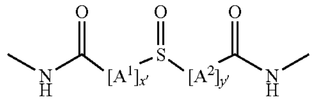

wherein $[A^1]$ are the same or different and each is a methylene group optionally substituted by substituent(s) selected from a hydroxy group, a phenyl group and an optionally substituted $C_{1-6}$ alkyl group, wherein the two substituents bonded to the single carbon atom are optionally combined to each other to form a hydrocarbon ring, and $[A^2]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in $[A^1]$ or $[A^2]$ is optionally combined to the substituent on the adjacent methylene group to form an optionally substituted hydrocarbon ring, n is an integer of 1 to 5, and x' and y' are each 0 or natural number, and the sum is 0 to 4.

(a) When Q' is (I'a): n is preferably an integer of 2 to 4. As the substituent for the methylene group in $[A^1]$, a phenyl group and an optionally substituted $C_{1-6}$ alkyl group (e.g., methyl) are preferable, a phenyl group and a $C_{1-6}$ alkyl group (e.g., methyl) are more preferable, and phenyl and methyl are particularly preferable. Alternatively, the two substituents bonded to the single carbon atom are preferably combined to each other to form a cycloalkane ring (e.g., a cyclopentane ring), particularly preferably a cyclopentane ring. Moreover, the methylene group is preferably combined to the substituent on the adjacent methylene group to form an optionally substituted a cycloalkane ring (e.g., a cyclopropane ring, a cyclobutane ring), more preferably a cycloalkane ring (e.g., a cyclopropane ring, a cyclobutane ring), particularly preferably a cyclopropane ring or a cyclobutane ring.

(b) When Q' is (I'b): n is preferably 3. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable. $R^{4A}$ and $R^{4B}$ are the same or different and each is preferably an optionally substituted $C_{1-6}$ alkyl group (e.g., methyl), more preferably a $C_{1-6}$ alkyl group (e.g., methyl), particularly preferably methyl.

(c) When Q' is (I'c): n is preferably 3. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable. $R^{4A}$ is preferably an optionally substituted $C_{1-6}$ alkyl group (e.g., propyl), or an optionally substituted $C_{7-12}$ aralkyl group (e.g., benzyl), more preferably a $C_{1-6}$ alkyl group (e.g., propyl) optionally substituted by $C_{1-6}$ alkoxy group(s) (e.g., methoxy), or a $C_{7-12}$ aralkyl group (e.g., benzyl), particularly preferably methoxypropyl or benzyl.

(d) When Q' is (I'd): n is preferably 3. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

(e) When Q' is (I'e): n' is preferably 2. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

(f) When Q' is (I'f): n is preferably 3. As the substituent for the methylene group in $[A^1]$, an optionally substituted $C_{1-6}$ alkyl group (e.g., methyl, ethyl) is preferable, a $C_{1-6}$ alkyl group (e.g., methyl, ethyl) is more preferable, and methyl and ethyl are particularly preferable. In another embodiment, the methylene group in $[A^1]$ is preferably unsubstituted.

(g) When Q' is (I'g): n' is preferably 2. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

(h) When Q' is (I'h): n is preferably 3. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

(i) When Q' is (I'i): n is preferably 3. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

(j) When Q' is (I'j): n is preferably 3. As the substituent for the methylene group in $[A^1]$, a hydroxy group and an optionally substituted $C_{1-6}$ alkyl group (e.g., methyl) are preferable, a hydroxy group and a $C_{1-6}$ alkyl group (e.g., methyl) are more preferable, and hydroxy and methyl are particularly preferable. In another embodiment, the methylene group in $[A^1]$ is preferably unsubstituted.

(k) When Q' is (I'k): n is preferably 3. The methylene group in $[A^1]$ is preferably unsubstituted. $R^{4A}$ is preferably an optionally substituted $C_{1-6}$ alkyl group (e.g., ethyl, propyl), more preferably a $C_{1-6}$ alkyl group (e.g., ethyl, propyl) optionally substituted by $C_{1-6}$ alkoxy group(s) (e.g., methoxy), particularly preferably ethyl or methoxypropyl.

(l) When Q' is (I'l): X' is preferably a sulfur atom (i.e., Q' is (I'l')), or an imino group having a $C_{1-6}$ alkyl group (e.g., methyl) or a hydrogen atom, particularly preferably a sulfur atom, or an imino group having a $C_{1-6}$ alkyl group (e.g., methyl). The methylene group in $[A^1]$ or $[A^2]$ is preferably unsubstituted. x' and y' are preferably each 1.

(m) When Q' is (I'm): the methylene group in $[A^1]$ or $[A^2]$ is preferably unsubstituted. x' and y' are preferably each 1.

(n) When Q' is (I'n): the methylene group in $[A^1]$ or $[A^2]$ is preferably unsubstituted. x' and y' are preferably each 1.

(o) When Q' is (I'o): n" is preferably 1. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

(p) When Q' is (I'p): n' is preferably 2. As the substituent for the methylene group in $[A^1]$, an optionally substituted $C_{1-6}$ alkyl group (e.g., methyl) is preferable, a $C_{1-6}$ alkyl group (e.g., methyl) is more preferable, and methyl is particularly preferable.

Ring B' is a benzene ring optionally having additional substituent(s), or a pyridine ring optionally having additional substituent(s), provided that when $R^{5A}$ is a halogen Atom, then Ring B' is a benzene ring optionally having additional substituent(s).

As the "substituent" of the "benzene ring optionally having additional substituent(s)" for Ring B', a halogen atom, a cyano group, a $C_{1-6}$ alkoxy group and an optionally substituted hydrocarbon group are preferable, a halogen atom, a cyano group, a $C_{1-6}$ alkoxy group and an optionally substituted $C_{1-6}$ alkyl group are more preferable, a halogen atom (e.g., a chlorine atom), a cyano group, a $C_{1-6}$ alkoxy group (e.g., methoxy), and a $C_{1-6}$ alkyl group (e.g., methyl) optionally substituted by 1 to 3 halogen atoms (e.g., a fluorine atom) are still more preferable, and a chlorine atom, cyano, methoxy, methyl and trifluoromethyl are particularly preferable. In another embodiment, the “benzene ring optionally having additional substituent(s)” preferably has no substituent(s).

As the “substituent” of the “pyridine ring optionally having additional substituent(s)” for Ring B', an optionally substituted hydrocarbon group is preferable, an optionally substituted $C_{1-6}$ alkyl group is more preferable, a $C_{1-6}$ alkyl group (e.g., methyl) is still more preferable, and methyl is particularly preferable. In another embodiment, the “pyridine ring optionally having additional substituent(s)” preferably has no substituent(s).

Preferable examples of the ring, group, substituent and the like explained in the present specification are more preferably used in combination.

Compound (I') is preferably a compound wherein $R^{1A}$ is an optionally substituted $C_{1-6}$ alkyl group;

$R^{2A}$ and $R^{3A}$ are each independently a hydrogen atom or an optionally substituted hydrocarbon group, or $R^{2A}$ and $R^{3A}$ form, together with the carbon atoms which they are bonded to, an optionally substituted arene ring or an optionally substituted cycloalkene ring;

$R^{5A}$ is a hydrogen atom or a halogen atom;

Q' is a bivalent group selected from (I'a): n is an integer of 2 to 4, and the methylene group in [$A^1$] is optionally substituted by phenyl group(s) or optionally substituted $C_{1-6}$ alkyl group(s), or the two substituents bonded to the single carbon atom are combined to each other to form a cycloalkane ring, or the methylene group is combined to the substituent on the adjacent methylene group to form an optionally substituted a cycloalkane ring;

(I'b): n is 3, the methylene group in [$A^1$] is optionally substituted by optionally substituted $C_{1-6}$ alkyl group(s), and $R^{4A}$ and $R^{4B}$ are the same or different and each is an optionally substituted $C_{1-6}$ alkyl group;

(I'c): n is 3, the methylene group in [$A^1$] is optionally substituted by optionally substituted $C_{1-6}$ alkyl group(s), and $R^{4A}$ is an optionally substituted $C_{1-6}$ alkyl group or an optionally substituted $C_{7-12}$ aralkyl group;

(I'd): n is 3, and the methylene group in [$A^1$] is optionally substituted by optionally substituted $C_{1-6}$ alkyl group(s);

(I'e): n' is 2, and the methylene group in [$A^1$] is optionally substituted by optionally substituted $C_{1-6}$ alkyl group(s);

(I'f): n is 3, and the methylene group in [$A^1$] is unsubstituted, or optionally substituted by optionally substituted $C_{1-6}$ alkyl group(s);

(I'g): n' is 2, and the methylene group in [$A^1$] is optionally substituted by optionally substituted $C_{1-6}$ alkyl group(s);

(I'h): n is 3, and the methylene group in [$A^1$] is optionally substituted by optionally substituted $C_{1-6}$ alkyl group(s);

(I'i): n is 3, and the methylene group in [$A^1$] is optionally substituted by optionally substituted $C_{1-6}$ alkyl group(s);

(I'j): n is 3, and the methylene group in [$A^1$] is optionally substituted by hydroxy group(s) or optionally substituted $C_{1-6}$ alkyl group(s);

(I'k): n is 3, the methylene group in [$A^1$] is unsubstituted, and $R^{4A}$ is an optionally substituted $C_{1-6}$ alkyl group;

(I'l): X' is a sulfur atom, or an imino group having a $C_{1-6}$ alkyl group or a hydrogen atom, the methylene in [$A^1$] or [$A^2$] is unsubstituted, and x' and y' are each 1;

(I'm): the methylene in [$A^1$] or [$A^2$] is unsubstituted, and x' and y' are each 1;

(I'n): the methylene in [$A^1$] or [$A^2$] is unsubstituted, and x' and y' are each 1;

(I'o): n" is 1, and the methylene group in [$A^1$] is optionally substituted by optionally substituted alkyl group(s); and (I'p): n' is 2, and the methylene group in [$A^1$] is optionally substituted by optionally substituted $C_{1-6}$ alkyl group(s); and Ring B' is (1) a benzene ring optionally having additional substituent(s) selected from a halogen atom, a cyano group, a $C_{1-6}$ alkoxy group and an optionally substituted hydrocarbon group, or (2) a pyridine ring optionally having optionally substituted hydrocarbon group(s).

Compound (I') is more preferably a compound wherein $R^{1A}$ is an optionally substituted $C_{1-6}$ alkyl group (e.g., methyl, ethyl, propyl, isobutyl);

$R^{2A}$ and $R^{3A}$ are each independently a hydrogen atom or an optionally substituted $C_{1-6}$ alkyl group (e.g., methyl), or $R^{2A}$ and $R^{3A}$ form, together with the carbon atoms which they are bonded to, an optionally substituted arene ring (e.g., a benzene ring) or an optionally substituted cycloalkene ring (e.g., a cyclohexene ring);

$R^{5A}$ is a hydrogen atom or a halogen atom (e.g., a chlorine atom);

Q' is a bivalent group selected from (I'a): n is an integer of 2 to 4, and the methylene group in [$A^1$] is optionally substituted by phenyl group(s) or optionally substituted $C_{1-6}$ alkyl group(s) (e.g., methyl), or the two substituents bonded to the single carbon atom are combined to each other to form a cycloalkane ring (e.g., a cyclopentane ring), or the methylene group is combined to the substituent on the adjacent methylene group to form an optionally substituted cycloalkane ring (e.g., a cyclopropane ring, a cyclobutane ring);

(I'b): n is 3, the methylene group in [$A^1$] is optionally substituted by optionally substituted $C_{1-6}$ alkyl group(s) (e.g., methyl), and $R^{4A}$ and $R^{4B}$ are the same or different and each is an optionally substituted $C_{1-6}$ alkyl group (e.g., methyl);

(I'c): n is 3, the methylene group in [$A^1$] is optionally substituted by optionally substituted $C_{1-6}$ alkyl group(s) (e.g., methyl), and $R^{4A}$ is an optionally substituted $C_{1-6}$ alkyl group (e.g., propyl), or an optionally substituted $C_{7-12}$ aralkyl group (e.g., benzyl);

(I'd): n is 3, and the methylene group in [$A^1$] is optionally substituted by optionally substituted $C_{1-6}$ alkyl group(s) (e.g., methyl);

(I'e): n' is 2, and the methylene group in [$A^1$] is optionally substituted by optionally substituted $C_{1-6}$ alkyl group(s) (e.g., methyl);

(I'f): n is 3, and the methylene group in [$A^1$] is unsubstituted, or optionally substituted by optionally substituted $C_{1-6}$ alkyl group(s) (e.g., methyl, ethyl);

(I'g): n' is 2, and the methylene group in [$A^1$] is optionally substituted by optionally substituted $C_{1-6}$ alkyl group(s) (e.g., methyl);

(I'h): n is 3, and the methylene group in [$A^1$] is optionally substituted by optionally substituted $C_{1-6}$ alkyl group(s) (e.g., methyl);

(I'i): n is 3, and the methylene group in [$A^1$] is optionally substituted by optionally substituted $C_{1-6}$ alkyl group(s) (e.g., methyl);

(I'j): n is 3, and the methylene group in [$A^1$] is optionally substituted by hydroxy group(s) or optionally substituted $C_{1-6}$ alkyl group(s) (e.g., methyl);

(I'k): n is 3, the methylene group in [$A^1$] is unsubstituted, and $R^{4A}$ is an optionally substituted $C_{1-6}$ alkyl group (e.g., ethyl, propyl);

(I'l): X' is a sulfur atom, or an imino group having a $C_{1-6}$ alkyl group (e.g., methyl) or a hydrogen atom, the methylene in [$A^1$] or [$A^2$] is unsubstituted, and x' and y' are each 1;

(I'm): the methylene in [$A^1$] or [$A^2$] is unsubstituted, and x' and y' are each 1;

(I'n): the methylene in [$A^1$] or [$A^2$] is unsubstituted, and x' and y' are each 1;

(I'o): n'' is 1, and the methylene group in [$A^1$] is optionally substituted by optionally substituted alkyl group(s); and (I'p): n' is 2, and the methylene group in [$A^1$] is optionally substituted by optionally substituted alkyl group(s) (e.g., methyl); and Ring B' is (1) a benzene ring optionally having additional substituent(s) selected from a halogen atom, a cyano group, a $C_{1-6}$ alkoxy group and an optionally substituted $C_{1-6}$ alkyl group, or (2) a pyridine ring optionally having optionally substituted $C_{1-6}$ alkyl group(s).

Compound (I') is still more preferably a compound wherein $R^{1A}$ is a $C_{1-6}$ alkyl group (e.g., methyl, ethyl, propyl, isobutyl);

$R^{2A}$ and $R^{3A}$ are each independently a hydrogen atom or a $C_{1-6}$ alkyl group (e.g., methyl), or $R^{2A}$ and $R^{3A}$ form, together with the carbon atoms which they are bonded to, an arene ring (e.g., a benzene ring) or a cycloalkene ring (e.g., a cyclohexene ring);

Q' is a bivalent group selected from (I'a): n is an integer of 2 to 4, and the methylene group in [$A^1$] is optionally substituted by phenyl group(s) or $C_{1-6}$ alkyl group(s) (e.g., methyl), or the two substituents bonded to the single carbon atom are combined to each other to form a cycloalkane ring (e.g., a cyclopentane ring), or the methylene group is combined to the substituent on the adjacent methylene group to form a cycloalkane ring (e.g., a cyclopropane ring, a cyclobutane ring);

(I'b): n is 3, the methylene group in [$A^1$] is optionally substituted by $C_{1-6}$ alkyl group(s) (e.g., methyl), and $R^{4A}$ and $R^{4B}$ are the same or different and each is a $C_{1-6}$ alkyl group (e.g., methyl);

(I'c): n is 3, the methylene group in [$A^1$] is optionally substituted by $C_{1-6}$ alkyl group(s) (e.g., methyl), and $R^{4A}$ is a $C_{1-6}$ alkyl group (e.g., propyl) optionally substituted by $C_{1-6}$ alkoxy group(s) (e.g., methoxy), or a $C_{7-12}$ aralkyl group (e.g., benzyl);

(I'd): n is 3, and the methylene group in [$A^1$] is optionally substituted by $C_{1-6}$ alkyl group(s) (e.g., methyl);

(I'e): n' is 2, and the methylene group in [$A^1$] is optionally substituted by $C_{1-6}$ alkyl group(s) (e.g., methyl);

(I'f): n is 3, and the methylene group in [$A^1$] is unsubstituted, or optionally substituted by $C_{1-6}$ alkyl group(s) (e.g., methyl, ethyl);

(I'g): n' is 2, and the methylene group in [$A^1$] is optionally substituted by $C_{1-6}$ alkyl group(s) (e.g., methyl);

(I'h): n is 3, and the methylene group in [$A^1$] is optionally substituted by $C_{1-6}$ alkyl group(s) (e.g., methyl);

(I'i): n is 3, and the methylene group in [$A^1$] is optionally substituted by $C_{1-6}$ alkyl group(s) (e.g., methyl);

(I'j): n is 3, and the methylene group in [$A^1$] is optionally substituted by hydroxy group(s) or $C_{1-6}$ alkyl group(s) (e.g., methyl);

(I'k): n is 3, the methylene group in [$A^1$] is unsubstituted, and $R^{4A}$ is a $C_{1-6}$ alkyl group (e.g., ethyl, propyl) optionally substituted by $C_{1-6}$ alkoxy group(s) (e.g., methoxy);

(I'l): X' is a sulfur atom, or an imino group having a $C_{1-6}$ alkyl group (e.g., methyl), the methylene in [$A^1$] or [$A^2$] is unsubstituted, and x' and y' are each 1;

(I'm): the methylene in [$A^1$] or [$A^2$] is unsubstituted, and x' and y' are each 1;

(I'n): the methylene in [$A^1$] or [$A^2$] is unsubstituted, and x' and y' are each 1;

(I'o): n'' is 1, and the methylene group in [$A^1$] is optionally substituted by $C_{1-6}$ alkyl group(s) (e.g., methyl); and (I'p): n' is 2, and the methylene group in [$A^1$] is optionally substituted by $C_{1-6}$ alkyl group(s) (e.g., methyl); and Ring B' is (1) a benzene ring optionally having additional substituent(s) selected from a halogen atom (e.g., a chlorine atom), a cyano group, a $C_{1-6}$ alkoxy group (e.g., methoxy), and a $C_{1-6}$ alkyl group (e.g., methyl) optionally substituted by 1 to 3 halogen atoms (e.g., a fluorine atom), or (2) a pyridine ring optionally having $C_{1-6}$ alkyl group(s) (e.g., methyl).

Compound (I') is particularly preferably a compound wherein $R^{1A}$ is methyl, ethyl, propyl or isobutyl;

$R^{2A}$ and $R^{3A}$ are each a hydrogen atom or methyl, or $R^{2A}$ and $R^{3A}$ form, together with the carbon atoms which they are bonded to, a benzene ring or a cyclohexene ring;

Q' is a bivalent group selected from (I'a): n is an integer of 2 to 4, and the methylene group in [$A^1$] is optionally substituted by phenyl or methyl, or the two substituents bonded to the single carbon atom are combined to each other to form a cyclopentane ring, or the methylene group is combined to the substituent on the adjacent methylene group to form a cyclopropane ring or a cyclobutane ring;

(I'b): n is 3, the methylene group in [$A^1$] is optionally substituted by methyl, and $R^{4A}$ and $R^{4B}$ are each methyl;

(I'c): n is 3, the methylene group in [$A^1$] is optionally substituted by methyl, and $R^{4A}$ is methoxypropyl or benzyl;

(I'd): n is 3, and the methylene group in [$A^1$] is optionally substituted by methyl;

(I'e): n' is 2, and the methylene group in [$A^1$] is optionally substituted by methyl;

(I'f): n is 3, and the methylene group in [$A^1$] is unsubstituted, or optionally substituted by methyl or ethyl;

(I'g): n' is 2, and the methylene group in [$A^1$] is optionally substituted by methyl;

(I'h): n is 3, and the methylene group in [$A^1$] is optionally substituted by methyl;

(I'i): n is 3, and the methylene group in [$A^1$] is optionally substituted by methyl;

(I'j): n is 3, and the methylene group in [$A^1$] is optionally substituted by hydroxy or methyl;

(I'k): n is 3, the methylene group in [$A^1$] is unsubstituted, and $R^{4A}$ is ethyl or methoxypropyl;

(I'l): X' is a sulfur atom, or an imino group having methyl, the methylene in [$A^1$] or [$A^2$] is unsubstituted, and x' and y' are each 1;

(I'm): the methylene in [$A^1$] or [$A^2$] is unsubstituted, and x' and y' are each 1;

(I'n): the methylene in [$A^1$] or [$A^2$] is unsubstituted, and x' and y' are each 1;

(I'o): n'' is 1, and the methylene group in [$A^1$] is optionally substituted by methyl; and (I'p): n' is 2, and the methylene group in [$A^1$] is optionally substituted by methyl; and Ring B' is (1) a benzene ring optionally having additional substituent(s) selected from a chlorine atom, cyano, methoxy, methyl and trifluoromethyl, or (2) a pyridine ring optionally having methyl.

Specific examples of the above-mentioned compound (I') include the compounds of Examples. Among them, N-(4-cyanophenyl)-N'-(9-ethyl-2,3,4,9-tetrahydro-1H-carbazol-6-yl)-3-methylpentanediamide or a salt thereof (Example 4), N-(3-chloro-4-cyanophenyl)-N'-(9-ethyl-9H-carbazol-3-yl)-3-methylpentanediamide or a salt thereof (Example 14), and N-{4-[(3-chloro-4-cyanophenyl)amino]-2-methyl-4-oxobutyl}-9-ethyl-9H-carbazole-3-carboxamide or a salt thereof (Example 48)

are preferable.

The definition of each symbol in the formula (I) is explained in detail in the following.

$R^1$ is an optionally substituted hydrocarbon group or an optionally substituted hydrocarbon-oxy group.

$R^1$ is preferably an optionally substituted $C_{1-6}$ alkyl group (e.g., ethyl, propyl, isobutyl), more preferably a $C_{1-6}$ alkyl group (e.g., ethyl, propyl, isobutyl), particularly preferably ethyl, propyl or isobutyl.

$R^2$ and $R^3$ are each independently an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^2$ and $R^3$ optionally form, together with the carbon atoms which they are bonded to, an optionally substituted hydrocarbon ring.

$R^2$ and $R^3$ are preferably each independently an optionally substituted hydrocarbon group, more preferably an optionally substituted $C_{1-6}$ alkyl group (e.g., methyl), still more preferably a $C_{1-6}$ alkyl group (e.g., methyl), particularly preferably methyl.

Alternatively, $R^2$ and $R^3$ preferably form, together with the carbon atoms which they are bonded to, an optionally substituted arene ring (e.g., a benzene ring) or an optionally substituted cycloalkene ring (e.g., a cyclohexene ring), more preferably an arene ring (e.g., a benzene ring) or a cycloalkene ring (e.g., a cyclohexene ring), particularly preferably a benzene ring or a cyclohexene ring.

Q is a bivalent group selected from (Ia)

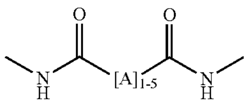

(Ib)

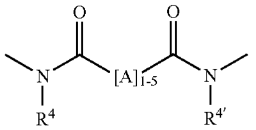

(Ic)

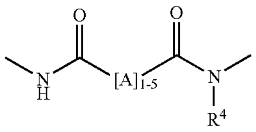

(Id)

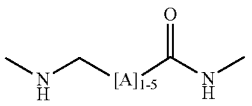

(Ie)

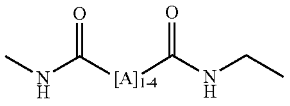

-continued (If)

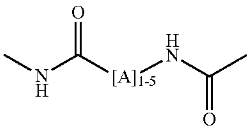

(Ig)

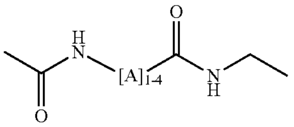

(Ih)

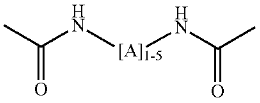

(Ii)

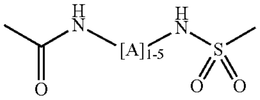

(Ij)

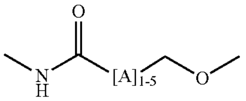

(Ik)

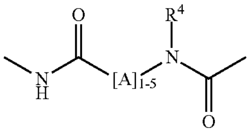

(Il)

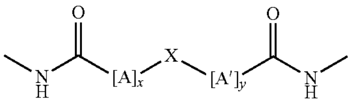

(Im)

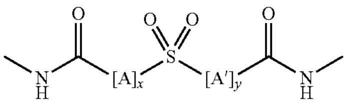

and (In)

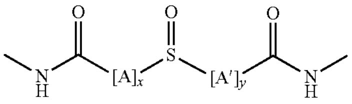

wherein

[A] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, and [A'] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [A] or [A'] is optionally combined to the substituent on the adjacent methylene group to form an optionally substituted hydrocarbon ring, $R^4$ and $R^{4'}$ are the same or different and each is an optionally substituted hydrocarbon group, X is an oxygen atom, a sulfur atom, or an imino group having an optionally substituted hydrocarbon group or a hydrogen atom, and x and y are each 0 or natural number, and the sum is 0 to 4.

Q is preferably (Ia)

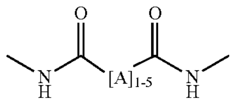

(Ij)

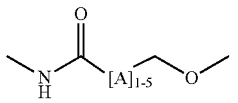

(Il')

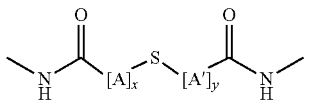

or (In)

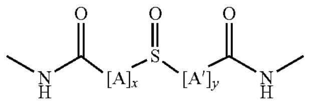

wherein each symbol is as defined above.

(a) When Q is (Ia): the number of the methylene group in [A] is preferably 2 to 4. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable. Alternatively, the two substituents bonded to the single carbon atom are preferably combined to each other to form a cycloalkane ring (e.g., a cyclopentane ring), particularly preferably a cyclopentane ring. Moreover, the methylene group is preferably combined to the substituent on the adjacent methylene group to form an optionally substituted cycloalkane ring (e.g., a cyclopropane ring), more preferably a cycloalkane ring (e.g., a cyclopropane ring), particularly preferably a cyclopropane ring.

(b) When Q is (Ib): the number of the methylene group in [A] is preferably 3. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable. $R^4$ and $R^{4'}$ are the same or different and each is preferably an optionally substituted $C_{1-6}$ alkyl group (e.g., methyl), more preferably a $C_{1-6}$ alkyl group (e.g., methyl), particularly preferably methyl.

(c) When Q is (Ic): the number of the methylene group in [A] is preferably 3. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable. $R^4$ is preferably an optionally substituted $C_{1-6}$ alkyl group (e.g., propyl), or an optionally substituted $C_{7-12}$ aralkyl group (e.g., benzyl), more preferably a $C_{1-6}$ alkyl group (e.g., propyl) optionally substituted by $C_{1-6}$ alkoxy group(s) (e.g., methoxy), or a $C_{7-12}$ aralkyl group (e.g., benzyl), particularly preferably methoxypropyl or benzyl.

(d) When Q is (Id): the number of the methylene group in [A] is preferably 3. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable.

(e) When Q is (Ie): the number of the methylene group in [A] is preferably 2. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable.

(f) When Q is (If): the number of the methylene group in [A] is preferably 3. The methylene group is preferably unsubstituted.

(g) When Q is (Ig): the number of the methylene group in [A] is preferably 2. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable.

(h) When Q is (Ih): the number of the methylene group in [A] is preferably 3. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable.

(i) When Q is (Ii): the number of the methylene group in [A] is preferably 3. As the substituent for the methylene group, an optionally substituted $C_{1-6}$ alkyl group (e.g., methyl) is preferable, a $C_{1-6}$ alkyl group (e.g., methyl) is more preferable, and methyl is particularly preferable.

(j) When Q is (Ij): the number of the methylene group in [A] is preferably 3. As the substituent for the methylene group, none, a hydroxy group and an optionally substituted $C_{1-6}$ alkyl group (e.g., methyl) are preferable, none, a hydroxy group and a $C_{1-6}$ alkyl group (e.g., methyl) are more preferable, none, and hydroxy and methyl are particularly preferable.

(k) When Q is (Ik): the number of the methylene group in [A] is preferably 3. The methylene group is preferably unsubstituted. $R^4$ is preferably an optionally substituted $C_{1-6}$ alkyl group (e.g., ethyl, propyl), more preferably a $C_{1-6}$ alkyl group (e.g., ethyl, propyl) optionally substituted by $C_{1-6}$ alkoxy group(s) (e.g., methoxy), particularly preferably ethyl or methoxypropyl.

(l) When Q is (Il): X is preferably a sulfur atom (i.e., Q is (Il')), or an imino group having a $C_{1-6}$ alkyl group (e.g., methyl) or a hydrogen atom, particularly preferably a sulfur atom, or an imino group having a $C_{1-6}$ alkyl group (e.g., methyl).

The methylene group in [A] or [A'] is preferably unsubstituted. x and y are preferably each 1.

(m) When Q is (Im): the methylene group in [A] or [A'] is preferably unsubstituted. x and y are preferably each 1.

(n) When Q is (In): the methylene group in [A] or [A'] is preferably unsubstituted. x and y are preferably each 1.

Ring B is a benzene ring optionally further substituted by substituent(s) excluding cyano.

As the "substituent" of the "benzene ring optionally further substituted by substituent(s) excluding cyano" for Ring B, a halogen atom and an optionally substituted hydrocarbon group are preferable, a halogen atom and an optionally substituted $C_{1-6}$ alkyl group are more preferable, a halogen atom (e.g., a chlorine atom), and a $C_{1-6}$ alkyl group (e.g., methyl) optionally substituted by 1 to 3 halogen atoms (e.g., a fluorine atom) are still more preferable, and a chlorine atom and trifluoromethyl are particularly preferable.

Preferable examples of the ring, group, substituent and the like explained in the present specification are more preferably used in combination.

Compound (I) is preferably a compound wherein $R^1$ is an optionally substituted $C_{1-6}$ alkyl group;

$R^2$ and $R^3$ are each independently an optionally substituted hydrocarbon group, or $R^2$ and $R^3$ form, together with the carbon atoms which they are bonded to, an optionally substituted arene ring or an optionally substituted cycloalkene ring;

Q is a bivalent group selected from (Ia): the number of the methylene group in [A] is 2 to 4, and the methylene group is optionally substituted by optionally substituted $C_{1-6}$ alkyl group(s), or the two substituents bonded to the single carbon atom are combined to each other to form a cycloalkane ring, or the methylene group is combined to the substituent on the adjacent methylene group to form an optionally substituted a cycloalkane ring;

(Ib): the number of the methylene group in [A] is 3, the methylene group is optionally substituted by optionally substituted $C_{1-6}$ alkyl group(s), and $R^4$ and $R^{4'}$ are the same or different and each is an optionally substituted $C_{1-6}$ alkyl group;

(Ic): the number of the methylene group in [A] is 3, the methylene group is optionally substituted by optionally substituted $C_{1-6}$ alkyl group(s), and $R^4$ is an optionally substituted $C_{1-6}$ alkyl group or an optionally substituted $C_{7-12}$ aralkyl group;

(Id): the number of the methylene group in [A] is 3, and the methylene group is optionally substituted by optionally substituted $C_{1-6}$ alkyl group(s);

(Ie): the number of the methylene group in [A] is 2, and the methylene group is optionally substituted by optionally substituted $C_{1-6}$ alkyl group(s);

(If): the number of the methylene group in [A] is 3, and the methylene group is unsubstituted;

(Ig): the number of the methylene group in [A] is 2, and the methylene group is optionally substituted by optionally substituted $C_{1-6}$ alkyl group(s);

(Ih): the number of the methylene group in [A] is 3, and the methylene group is optionally substituted by optionally substituted $C_{1-6}$ alkyl group(s);

(Ii): the number of the methylene group in [A] is 3, and the methylene group is optionally substituted by optionally substituted $C_{1-6}$ alkyl group(s);

(Ij): the number of the methylene group in [A] is 3, and the methylene group is optionally substituted by hydroxy group(s) or optionally substituted $C_{1-6}$ alkyl group(s);

(Ik): the number of the methylene group in [A] is 3, the methylene group is unsubstituted, and $R^4$ is an optionally substituted $C_{1-6}$ alkyl group;

(Il): X is a sulfur atom, or an imino group having a $C_{1-6}$ alkyl group or a hydrogen atom, the methylene group in [A] or [A'] is unsubstituted, and x and y are each 1;

(Im): the methylene group in [A] or [A'] is unsubstituted, and x and y are each 1; and (In): the methylene group in [A] or [A'] is unsubstituted, and x and y are each 1; and Ring B is a benzene ring optionally further substituted by halogen atom(s) or optionally substituted hydrocarbon group(s).

Compound (I) is more preferably a compound wherein $R^1$ is an optionally substituted $C_{1-6}$ alkyl group (e.g., ethyl, propyl, isobutyl);

$R^2$ and $R^3$ are each independently an optionally substituted $C_1$ alkyl group (e.g., methyl), or $R^2$ and $R^3$ form, together with the carbon atoms which they are bonded to, an optionally substituted arene ring (e.g., a benzene ring) or an optionally substituted cycloalkene ring (e.g., a cyclohexene ring);

Q is a bivalent group selected from (Ia): the number of the methylene group in [A] is 2 to 4, and the methylene group is optionally substituted by $C_{1-6}$ alkyl group(s) (e.g., methyl), or the two substituents bonded to the single carbon atom are combined to each other to form a cycloalkane ring (e.g., a cyclopentane ring), or the methylene group is combined to the substituent on the adjacent methylene group to form an optionally substituted cycloalkane ring (e.g., a cyclopropane ring);

(Ib): the number of the methylene group in [A] is 3, the methylene group is optionally substituted by $C_{1-6}$ alkyl group(s) (e.g., methyl), and $R^4$ and $R^{4'}$ are the same or different and each is an optionally substituted $C_{1-6}$ alkyl group (e.g., methyl);

(Ic): the number of the methylene group in [A] is 3, the methylene group is optionally substituted by $C_{1-6}$ alkyl group(s) (e.g., methyl), and $R^4$ is an optionally substituted $C_{1-6}$ alkyl group (e.g., propyl), or an optionally substituted $C_{7-12}$ aralkyl group (e.g., benzyl);

(Id): the number of the methylene group in [A] is 3, and the methylene group is optionally substituted by optionally substituted $C_{1-6}$ alkyl group(s) (e.g., methyl);

(Ie): the number of the methylene group in [A] is 2, and the methylene group is optionally substituted by optionally substituted $C_{1-6}$ alkyl group(s) (e.g., methyl);

(If): the number of the methylene group in [A] is 3, and the methylene group is unsubstituted;

(Ig): the number of the methylene group in [A] is 2, and the methylene group is optionally substituted by optionally substituted $C_{1-6}$ alkyl group(s) (e.g., methyl);

(Ih): the number of the methylene group in [A] is 3, and the methylene group is optionally substituted by optionally substituted $C_{1-6}$ alkyl group(s) (e.g., methyl);

(Ii): the number of the methylene group in [A] is 3, and the methylene group is optionally substituted by optionally substituted $C_{1-6}$ alkyl group(s) (e.g., methyl);

(Ij): the number of the methylene group in [A] is 3, and the methylene group is optionally substituted by hydroxy group(s) or optionally substituted $C_{1-6}$ alkyl group(s) (e.g., methyl);

(Ik): the number of the methylene group in [A] is 3, the methylene group is unsubstituted, and $R^4$ is an optionally substituted $C_{1-6}$ alkyl group (e.g., ethyl, propyl);

(Il): X is a sulfur atom, or an imino group having a $C_{1-6}$ alkyl group (e.g., methyl) or a hydrogen atom, the methylene group in [A] or [A'] is unsubstituted, and x and y are each 1;

(Im): the methylene group in [A] or [A'] is unsubstituted, and x and y are each 1; and (In): the methylene group in [A] or [A'] is unsubstituted, and x and y are each 1; and Ring B is a benzene ring optionally further substituted by halogen atom(s) or optionally substituted $C_{1-6}$ alkyl group(s).

Compound (I) is still more preferably a compound wherein $R^1$ is a $C_{1-6}$ alkyl group (e.g., ethyl, propyl, isobutyl);

$R^2$ and $R^3$ are each independently a $C_{1-6}$ alkyl group (e.g., methyl), or $R^2$ and $R^3$ form, together with the carbon atoms which they are bonded to, an arene ring (e.g., a benzene ring) or a cycloalkene ring (e.g., a cyclohexene ring);

Q is a bivalent group selected from (Ia): the number of the methylene group in [A] is 2 to 4, and the methylene group is optionally substituted by $C_{1-6}$ alkyl group(s) (e.g., methyl), or the two substituents bonded to the single carbon atom are combined to each other to form a cycloalkane ring (e.g., a cyclopentane ring), or the methylene group is combined to the substituent on the adjacent methylene group to form a cycloalkane ring (e.g., a cyclopropane ring);

(Ib): the number of the methylene group in [A] is 3, the methylene group is optionally substituted by $C_{1-6}$ alkyl group(s) (e.g., methyl), and $R^4$ and $R^{4'}$ are the same or different and each is a $C_{1-6}$ alkyl group (e.g., methyl);

(Ic): the number of the methylene group in [A] is 3, the methylene group is optionally substituted by $C_{1-6}$ alkyl group(s) (e.g., methyl), and $R^4$ is a $C_{1-6}$ alkyl group (e.g., propyl) optionally substituted by $C_{1-6}$ alkoxy group(s) (e.g., methoxy), or a $C_{7-12}$ aralkyl group (e.g., benzyl);

(Id): the number of the methylene group in [A] is 3, and the methylene group is optionally substituted by $C_{1-6}$ alkyl group(s) (e.g., methyl);

(Ie): the number of the methylene group in [A] is 2, and the methylene group is optionally substituted by $C_{1-6}$ alkyl group(s) (e.g., methyl);

(If): the number of the methylene group in [A] is 3, and the methylene group is unsubstituted;

(Ig): the number of the methylene group in [A] is 2, and the methylene group is optionally substituted by $C_{1-6}$ alkyl group(s) (e.g., methyl);

(Ih): the number of the methylene group in [A] is 3, and the methylene group is optionally substituted by $C_{1-6}$ alkyl group(s) (e.g., methyl);

(Ii): the number of the methylene group in [A] is 3, and the methylene group is optionally substituted by $C_{1-6}$ alkyl group(s) (e.g., methyl);

(Ij): the number of the methylene group in [A] is 3, and the methylene group is optionally substituted by hydroxy group(s) or $C_{1-6}$ alkyl group(s) (e.g., methyl);

(Ik): the number of the methylene group in [A] is 3, the methylene group is unsubstituted, and $R^4$ is a $C_{1-6}$ alkyl group (e.g., ethyl, propyl) optionally substituted by $C_{1-6}$ alkoxy group(s) (e.g., methoxy);

(Il): X is a sulfur atom, or an imino group having a $C_{1-6}$ alkyl group (e.g., methyl), the methylene group in [A] or [A'] is unsubstituted, and x and y are each 1;

(Im): the methylene group in [A] or [A'] is unsubstituted, and x and y are each 1; and (In): the methylene group in [A] or [A'] is unsubstituted, and x and y are each 1; and Ring B is a benzene ring optionally further substituted by halogen atom(s) (e.g., a chlorine atom) or $C_{1-6}$ alkyl group(s) (e.g., methyl) optionally substituted by 1 to 3 halogen atoms (e.g., a fluorine atom).

Compound (I) is particularly preferably a compound wherein $R^1$ is ethyl, propyl or isobutyl;

$R^2$ and $R^3$ are each methyl, or $R^2$ and $R^3$ form, together with the carbon atoms which they are bonded to, a benzene ring or a cyclohexene ring;

Q is a bivalent group selected from (Ia): the number of the methylene group in [A] is 2 to 4, and the methylene group is optionally substituted by methyl, or the two substituents bonded to the single carbon atom are combined to each other to form a cyclopentane ring, or the methylene group is combined to the substituent on the adjacent methylene group to form a cyclopropane ring;

(Ib): the number of the methylene group in [A] is 3, the methylene group is optionally substituted by methyl, and $R^4$ and $R^{4'}$ are each methyl;

(Ic): the number of the methylene group in [A] is 3, the methylene group is optionally substituted by methyl, and $R^4$ is methoxypropyl or benzyl;

(Id): the number of the methylene group in [A] is 3, and the methylene group is optionally substituted by methyl;

(Ie): the number of the methylene group in [A] is 2, and the methylene group is optionally substituted by methyl;

(If): the number of the methylene group in [A] is 3, and the methylene group is unsubstituted;

(Ig): the number of the methylene group in [A] is 2, and the methylene group is optionally substituted by methyl;

(Ih): the number of the methylene group in [A] is 3, and the methylene group is optionally substituted by methyl;

(Ii): the number of the methylene group in [A] is 3, and the methylene group is optionally substituted by methyl;

(Ij): the number of the methylene group in [A] is 3, and the methylene group is optionally substituted by hydroxy or methyl;

(Ik): the number of the methylene group in [A] is 3, the methylene group is unsubstituted, and $R^4$ is ethyl or methoxypropyl;

(Il): X is a sulfur atom, or an imino group having methyl, the methylene group in [A] or [A'] is unsubstituted, and x and y are each 1;

(Im): the methylene group in [A] or [A'] is unsubstituted, and x and y are each 1; and (In): the methylene group in [A] or [A'] is unsubstituted, and x and y are each 1; and Ring B is a benzene ring optionally further substituted by chlorine atom(s) or trifluoromethyl.

Specific examples of the above-mentioned compound (I) include the compounds of Examples 1 to 35, 37, 38, 40 to 51 and 53 to 55.

Examples of salts of compound (I) and (I') include metal salts, ammonium salts, salts with organic base, salts with inorganic acid, salts with organic acid, salts with basic or acidic amino acids, and the like. Preferable examples of the metal salt include alkaline metal salts such as sodium salt, potassium salt and the like; alkaline earth metal salts such as calcium salt, magnesium salt, barium salt and the like; aluminum salts, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salt with aspartic acid, glutamic acid and the like.

Among them, pharmaceutically acceptable salts are preferable. For example, if the compound has an acidic functional group therein, examples of the salt include inorganic salts such as alkaline metal salts (e.g., sodium salt, potassium salt and the like), alkaline earth metal salts (e.g., calcium salt, magnesium salt, barium salt and the like) and the like; ammonium salt, and the like. If the compound has a basic functional group therein, examples of the salt thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The production methods of the compound (I) or (I') of the present invention or a salt thereof are explained below.

The intermediates produced in the following production methods may be isolated and purified according to methods such as column chromatography, recrystallization, distillation and the like, or may be directly used without isolation for the next step.

The compound (I'a)-compound (I'p) [i.e., compound (I'), wherein Q' in the formula (I') is each the bivalent group (I'a)-(I'p)] or a salt thereof of the present invention can be produced according to following Method A to Method L.

[Method A]

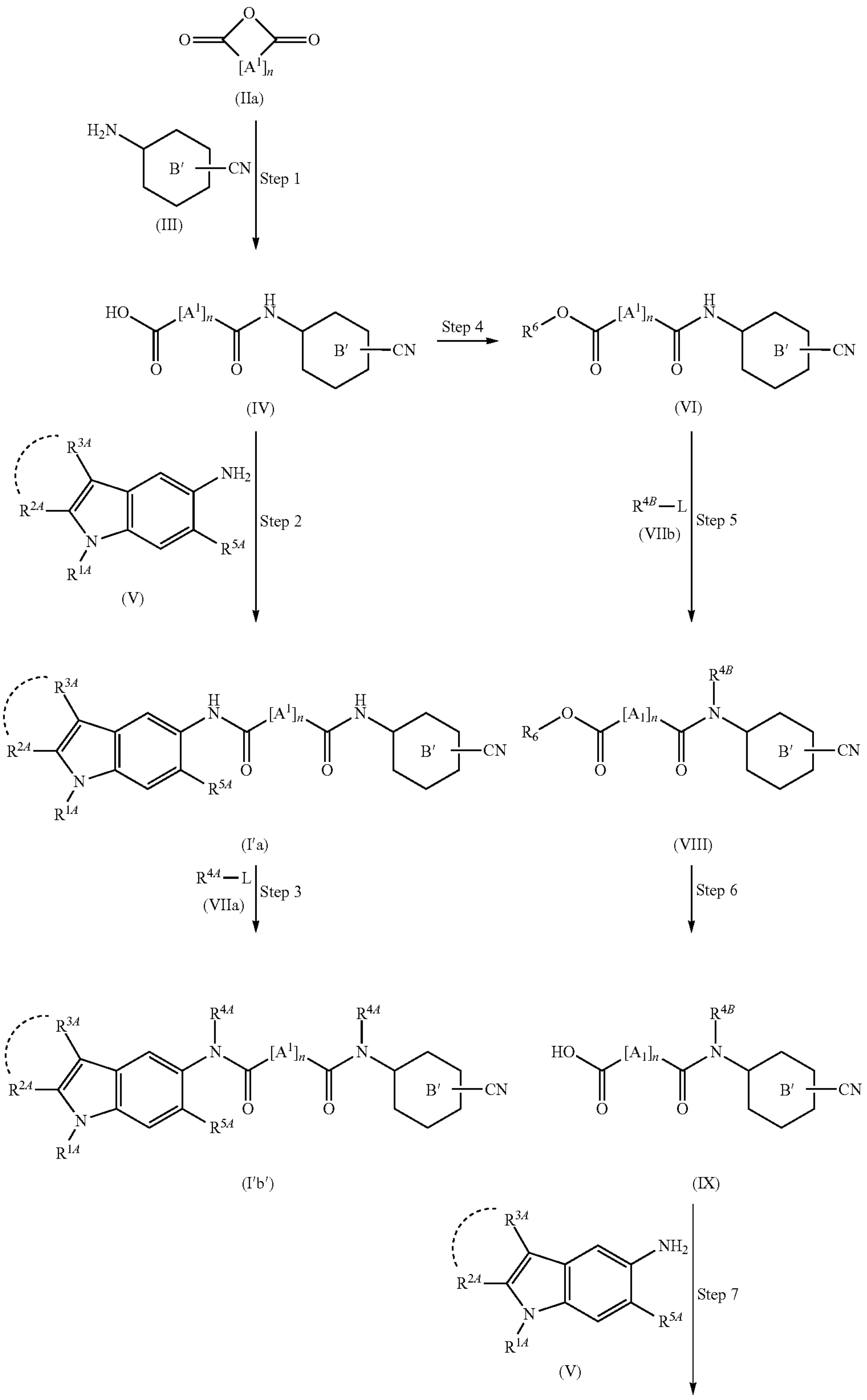

(IIa) (III) (IV) (VI) (V) (I'a) (VIII) (I'b') (IX) (V)

-continued

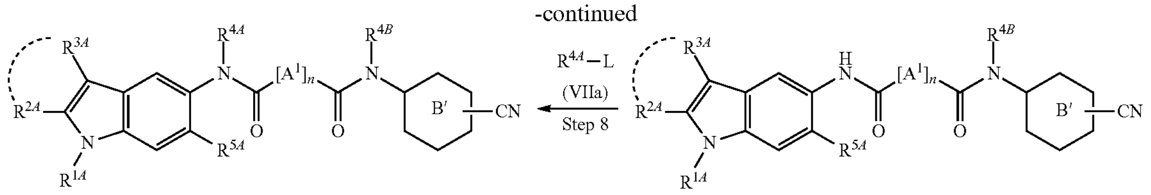

(I'b) (I'c)

wherein $R^6$ is an optionally substituted hydrocarbon group, L is a leaving group, and the other each symbols are as defined above.

Examples of the leaving group for L include halogen atoms (a chlorine atom, a bromine atom, an iodine atom etc.), substituted sulfonyloxy groups ($C_{1-6}$ alkylsulfonyloxy groups such as methanesulfonyloxy, ethanesulfonyloxy and the like; $C_{6-14}$ arylsulfonyloxy groups such as benzenesulfonyloxy, p-toluenesulfonyloxy and the like; $C_{7-16}$ aralkylsulfonyloxy groups such as benzylsulfonyloxy and the like, etc.), acyloxy groups (acetoxy, benzoyloxy etc.), oxy groups substituted by heterocycle or aryl group (succinimide, benzotriazole, quinoline, 4-nitrophenyl etc.), heterocycle (imidazole etc.) and the like.

(Step 1)

This step is a step of producing compound (IV) or a salt thereof by reacting compound (IIa) or a salt thereof with compound (III) or a salt thereof.

Compound (IIa) and compound (III) may be a commercially available product, or can also be produced according to a method known per se or a method analogous thereto.

When compound (IV) or a salt thereof is produced by reacting compound (IIa) or a salt thereof with compound (III) or a salt thereof, the reaction can be performed in a solvent that does not adversely influence the reaction. Examples of the solvent include alcohols (methanol, ethanol, propanol, 2-propanol, butanol, isobutanol, t-butanol etc.), hydrocarbons (benzene, toluene etc.), ethers (diethyl ether, dioxane, tetrahydrofuran etc.), esters (ethyl acetate etc.), halogenated hydrocarbons (chloroform, dichloromethane etc.), amides (N,N-dimethylformamide etc.) and the like, and they may be mixed as appropriate. Among these, tetrahydrofuran is preferably used.

The amount of compound (III) to be used is generally about 0.5 to 10 mol equivalent, preferably about 0.9 to 1.1 mol equivalent, per 1 mol of compound (IIa).

The reaction temperature is generally about −80 to 200° C., preferably about 25 to 150° C., and the reaction time is generally about 0.5 to 72 hr, preferably 1 to 48 hr.

(Step 2)

This step is a step of producing compound (I'a) or a salt thereof by reacting compound (IV) or a salt thereof with compound (V) or a salt thereof in the presence of a condensing agent.

Compound (V) may be a commercially available product, or can also be produced according to a method known per se or a method analogous thereto.

Examples of the condensing agent used in this step include dicyclohexylcarbodiimide, diisopropylcarbodiimide, N-ethyl-N'-3-dimethylaminopropylcarbodiimide and a hydrochloride thereof, benzotriazol-1-yloxy-tris(dimethylamino)phosphonium hexafluorophosphorate, diphenylphosphorylazide and the like. They can be used alone or in combination with an additive (e.g., N-hydroxysuccinimide, 1-hydroxybenzotriazole, 3-hydroxy-4-oxo-3,4-dihydro-1,2,3-benzotriazine etc.). The amount of the condensing agent to be used is about 1 to 10 mol equivalent, preferably about 1 to 2 mol equivalent, per 1 mol of compound (IV). The amount of the additive to be used is generally about 1 to 10 mol equivalent, preferably about 1 to 2 mol equivalent, per 1 mol of compound (IV).

The amount of compound (V) to be used is generally about 1 to 10 mol equivalent, preferably about 1 to 2 mol equivalent, per 1 mol of compound (IV).

The above-mentioned reaction is generally performed in a solvent that does not adversely influence the reaction, and a base may be added for the progress of the reaction. Examples of the solvent include hydrocarbons (benzene, toluene etc.), ethers (diethyl ether, dioxane, tetrahydrofuran etc.), esters (ethyl acetate etc.), halogenated hydrocarbons (chloroform, dichloromethane etc.), amides (N,N-dimethylformamide etc.) and the like, and they may be mixed as appropriate. Examples of the base include alkali metal hydroxides (sodium hydroxide, potassium hydroxide etc.), hydrogen carbonates (sodium hydrogen carbonate, potassium hydrogen carbonate etc.), carbonates (sodium carbonate, potassium carbonate etc.), acetates (sodium acetate etc.), tertiary amines (trimethylamine, triethylamine, N-methylmorpholine etc.), aromatic amines (pyridine, picoline, N,N-dimethylaniline etc.) and the like. The amount of the base to be used is generally about 1 to 100 mol equivalent, preferably about 1 to 5 mol equivalent, per 1 mol of the substrate. The reaction temperature is generally about −80 to 150° C., preferably about 0 to 50° C., and the reaction time is generally about 0.5 to 100 hr, preferably 0.5 to 60 hr.

(Step 3)

This step is a step of producing compound (I'b') or a salt thereof by reacting compound (I'a) or a salt thereof with compound (VIIa) or a salt thereof in the presence of a base.

Compound (VIIa) may be a commercially available product, or can also be produced according to a method known per se or a method analogous thereto.

Examples of the base used in this step include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide and the like, and the like), organic bases (amines such as trimethylamine, triethylamine, diisopropylethylamine and the like, cyclic amines such as pyridine, 4-dimethylaminopyridine and the like, and the like) and the like. Among these, sodium hydride is preferable. While the amount of the base to be used varies depending on the kind of the solvent and the other reaction conditions, it is generally about 1 to 10 mol equivalent, preferably about 1 to 5 mol equivalent, per 1 mol of compound (I'a).

The amount of compound (VIIa) to be used is generally about 1 to 10 mol equivalent, preferably about 1 to 3 mol equivalent, per 1 mol of compound (I'a).

This step is performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.) and the like. Among these, N,N-dimethylformamide is preferable. These solvent may be used in a mixture of two or more kinds thereof in an appropriate ratio.

The reaction temperature is, for example, within about 0 to 200° C., preferably about 25 to 100° C. While the reaction time varies depending on the kind of compound (I'a) or a salt thereof, the reaction temperature and the like, it is, for example, about 0.5 to 100 hr, preferably about 0.5 to 24 hr.

(Step 4)

This step is a step of producing compound (VI) or a salt thereof by subjecting compound (IV) or a salt thereof to esterification.

This reaction is a step of producing compound (VI) or a salt thereof by subjecting compound (IV) or a salt thereof to a dehydration reaction with the compound represented by the formula $R^6$—OH (XXXVI)

wherein each symbol is as defined above (hereinafter sometimes to be referred to as compound (XXXVI)) or a salt thereof in the presence of an acid catalyst, or to an alkylation reaction with the compound represented by the formula $R^6$-L (XXXVII)

wherein each symbol is as defined above (hereinafter sometimes to be referred to as compound (XXXVII)) in the presence of a base.

Compound (XXXVI) and compound (XXXVII) may be a commercially available product, or can also be produced according to a method known per se or a method analogous thereto.

Examples of the acid catalyst used for the reaction of compound (IV) or a salt thereof with compound (XXXVI) or a salt thereof include mineral acids (hydrochloric acid, sulfuric acid etc.), organic sulfonic acids (methanesulfonic acid, p-toluenesulfonic acid etc.), Lewis acids (boron fluoride etherate etc.) and the like. While the amount of the acid catalyst to be used varies depending on the kind of the solvent and the other reaction condition, it is generally about 0.0001 to 10 mol equivalent, preferably about 0.01 to 0.1 mol equivalent, per 1 mol of compound (IV).

The amount of compound (XXXVI) to be used is generally about 1 to 1000 mol equivalent, preferably about 10 to 100 mol equivalent, per 1 mol of compound (IV).

Examples of the solvent used for the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.) and the like. Compound (XXXVI) may be used as a solvent.

The reaction temperature is, for example, within about 0 to 200° C., preferably about 25 to 100° C. While the reaction time varies depending on the kind of compound (IV) or a salt thereof, the reaction temperature and the like, it is, for example, about 0.5 to 100 hr, preferably about 0.5 to 24 hr.

Examples of the base used for the reaction of compound (IV) or a salt thereof with compound (XXXVII) or a salt thereof include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, etc.). While the amount of the base to be used varies depending on the kind of the solvent and the other reaction condition, it is generally about 1 to mol equivalent, preferably about 1 to 5 mol equivalent, per 1 mol of compound (IV).

The amount of compound (XXXVII) to be used is generally about 1 to 10 mol equivalent, preferably about 1 to 3 mol equivalent, per 1 mol of compound (IV).

This step is performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.) and the like. These solvent may be used in a mixture of two or more kinds thereof in an appropriate ratio.

The reaction temperature is, for example, within about 0 to 200° C., preferably about 25 to 100° C. While the reaction time varies depending on the kind of compound (IV) or a salt thereof, the reaction temperature and the like, it is, for example, about 0.5 to 100 hr, preferably about 0.5 to 24 hr.

(Step 5)

This step is a step of producing compound (VIII) or a salt thereof by reacting compound (VI) or a salt thereof with compound (VIIb) or a salt thereof in the presence of a base. This step can be performed in the same manner as in the method described in Step 3 of Method A.

Compound (VIIb) may be a commercially available product, or can also be produced according to a method known per se or a method analogous thereto.

(Step 6)

This step is a step of converting compound (VIII) or a salt thereof to compound (IX) or a salt thereof by hydrolysis. This reaction can be performed according to a method known per se, generally in the presence of an acid or a base, where necessary, in a solvent that does not adversely influence the reaction.

Examples of the acid include mineral acids (hydrochloric acid, hydrobromic acid, sulfuric acid etc.), carboxylic acids (acetic acid, trifluoroacetic acid, trichloroacetic acid etc.), sulfonic acids (methanesulfonic acid, toluenesulfonic acid etc.), Lewis acids (aluminium chloride, tin chloride, zinc bromide etc.) and the like. Where necessary, they may be used in a mixture of two or more kinds thereof. While the amount of the acid to be used varies depending on the kind of the solvent and the other reaction condition, it is generally about 0.1 mol equivalent or more per 1 mol of compound (VIII). The acid may be used as a solvent.

Examples of the base include inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among these, sodium hydroxide is preferable. While the amount of the base to be used varies depending on the kind of the solvent and the other reaction condition, it is generally about 0.1 to 10 mol equivalent, preferably about 1 to 5 mol equivalent, per 1 mol of compound (VIII).

Examples of the solvent that does not adversely influence the reaction include alcohols (methanol, ethanol, propanol, 2-propanol, butanol, isobutanol, t-butanol etc.), hydrocarbons (benzene, toluene, xylene, hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), carboxylic acids (acetic acid etc.), amides (N,N-dimethylformamide, dimethylacetamide etc.), sulfoxides (dimethylsulfoxide etc.), water and the like. Among these, ethanol, tetrahydrofuran and water are preferable. These solvent may be used in a mixture of two or more kinds thereof in an appropriate ratio.

The reaction temperature is, for example, within about −50 to 200° C., preferably about 0 to 100° C. While the reaction time varies depending on the kind of compound (VIII) or a salt thereof, the reaction temperature and the like, it is, for example, about 0.5 to 100 hr, preferably about 0.5 to 24 hr.

(Step 7)

This step is a step of producing compound (I'c) or a salt thereof by reacting compound (IX) or a salt thereof with compound (V) or a salt thereof in the presence of a condensing agent. This step can be performed in the same manner as in the method described in Step 2 of Method A.

(Step 8)

This step is a step of producing compound (I'b) or a salt thereof by reacting compound (I'c) or a salt thereof with compound (VIIa) or a salt thereof in the presence of a base. This step can be performed in the same manner as in the method described in Step 3 of Method A.

[Method B]

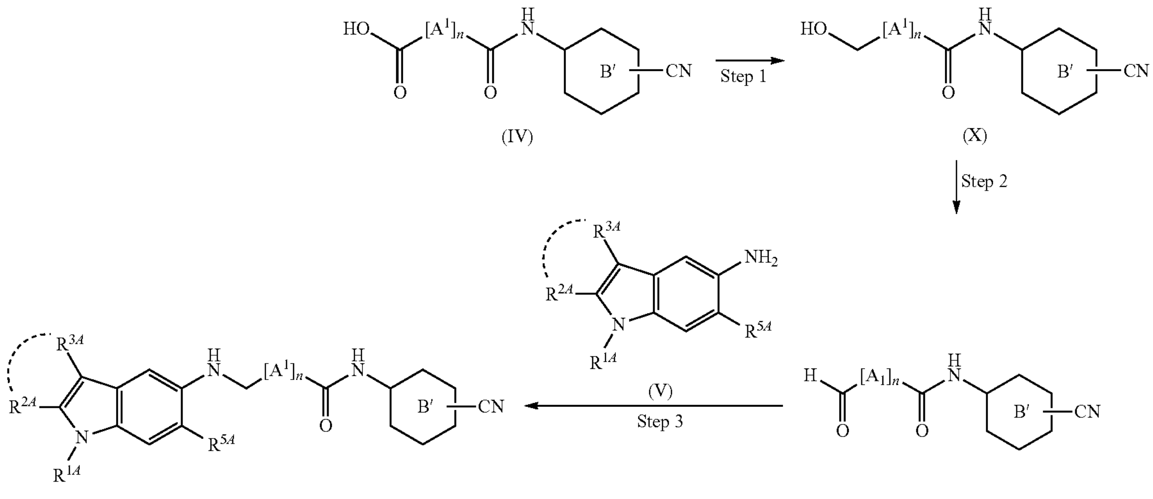

(IV) (X) (V) (I'd) (XI)

wherein each symbol is as defined above.

(Step 1)

This step is a step of producing compound (X) or a salt thereof by treating compound (IV) or a salt thereof with a reducing agent.

Examples of the reducing agent used in this step include metal hydrides (sodium borohydride, lithium borohydride, zinc borohydride, sodium cyanoborohydride, sodium triacetoxyborohydride, lithium cyanoborohydride, dibutylaluminum hydride, aluminium hydride, lithium aluminium hydride etc.), borane complexs (borane-tetrahydrofuran complex, catecholborane etc.) and the like. Among these, borane-tetrahydrofuran complex is preferable. The amount of the reducing agent to be used is, for example, about 1 to 50 mol equivalent, preferably about 1 to 10 mol equivalent, per 1 mol of compound (IV). Examples of the reaction solvent include aromatic hydrocarbons (toluene, xylene etc.), aliphatic hydrocarbons (heptane, hexane etc.), halogenated hydrocarbons (chloroform, dichloromethane etc.), ethers (diethyl ether, tetrahydrofuran, dioxane etc.), alcohols (methanol, ethanol, 2-propanol, butanol, benzyl alcohol etc.), nitriles (acetonitrile etc.), amides (N,N-dimethylformamide etc.), sulfoxides (dimethylsulfoxide etc.) and the like. Among these, tetrahydrofuran is preferable. These solvent may be used in a mixture thereof in an appropriate ratio. The reaction temperature is generally about −80° C. to 100° C., preferably about 0° C. to 40° C., and the reaction time is generally 5 min to 48 hr, preferably 1 to 24 hr.

(Step 2)

This step is a step of producing compound (XI) or a salt thereof by treating compound (X) or a salt thereof with an oxidizing agent.

Examples of the oxidizing agent used in this step include chromic acids (pyridinium chlorochromate (PCC), pyridinium dichromate (PDC) etc.), active manganese dioxides, dimethylsulfoxide-electrophiles (examples of the electrophile include oxalyl chloride, dicyclohexylcarbodiimide (DCC), acetic anhydride, trifluoroacetic anhydride, thionyl chloride, chlorine, N-chlorosuccinimide (NCS) etc.), oxoammonium salts (4-(benzoyloxy)-2,2,6,6-tetramethylpiperidin-1-oxyl etc.), tetrapropylammonium perruthenates (TPAP)-4-methylmorpholine N-oxide, hypervalent iodines (1,1,1-triacetoxy-1,1-dihydro-1,2-benziodoxol-3(1H)-one (Dess-Martin Periodinane)) and the like. The amount of the oxidizing agent to be used is generally about 1 to about 50 mol, preferably about 1 to about 10 mol, per 1 mol of compound (X).

Examples of the reaction solvent include aromatic hydrocarbons (toluene, xylene etc.), aliphatic hydrocarbons (heptane, hexane etc.), halogenated hydrocarbons (chloroform, dichloromethane etc.), ethers (diethyl ether, tetrahydrofuran, dioxane etc.), alcohols (methanol, ethanol, 2-propanol, butanol, benzyl alcohol etc.), nitriles (acetonitrile etc.), amides (N,N-dimethylformamide etc.), sulfoxides (dimethylsulfoxide etc.) and the like. These solvent may be used in a mixture thereof in an appropriate ratio.

While the reaction temperature varies depending on the kind of the oxidizing agent, it is generally about −78° C. to about 200° C., preferably about 0° C. to about 100° C., and the reaction time is generally about 0.5 hr to about 48 hr, preferably about 0.5 hr to about 24 hr.

(Step 3)

This step is a step of producing compound (I'd) or a salt thereof by subjecting compound (XI) or a salt thereof to a reductive alkylation reaction with compound (V) or a salt thereof.

The reductive alkylation reaction in this step can be performed according to a method known per se, for example, by reacting compound (XI) or a salt thereof with compound (V) or a salt thereof, and subjecting the resulting imine or iminium ion to a reduction reaction.

The amount of compound (V) to be used is generally about 1 to 10 mol equivalent, preferably about 1 to 3 mol equivalent, per 1 mol of compound (XI).

The solvent used for the reaction for producing imine or iminium ion is not particularly limited as long as the reaction proceeds. Examples thereof include hydrocarbons (heptane, hexane, toluene, xylene etc.), halogenated hydrocarbons (chloroform, dichloromethane, 1,2-dichloroethane etc.), ethers (diethyl ether, tetrahydrofuran, dioxane etc.), esters (ethyl acetate, t-butyl acetate etc.), alcohols (methanol, ethanol, 2-propanol etc.), nitriles (acetonitrile, butyronitrile etc.), amides (N,N-dimethylformamide, dimethylacetamide etc.), sulfoxides (dimethylsulfoxide etc.) and the like, and mixed solvents thereof.

In this step, the reaction can advantageously proceeds by the addition of a catalyst. Examples of the catalyst include mineral acids (hydrochloric acid, hydrobromic acid, sulfuric acid etc.), carboxylic acids (formic acid, acetic acid, propionic acid, trifluoroacetic acid etc.), sulfonic acids (methanesulfonic acid, p-toluenesulfonic acid etc.), Lewis acids (aluminium chloride, zinc chloride, zinc bromide, boron trifluoride, titanium chloride etc.), acetates (sodium acetate, potassium acetate etc.), molecular sieves (molecular sieve 3A, 4A, 5A etc.), dehydrating agents (magnesium sulfate etc.) and the like. The amount of the catalyst to be used is generally 0.01 to 50 mol equivalent, preferably about 0.1 to about 10 mol, per 1 mol of compound (XI).

The reaction temperature is generally about 0° C. to about 200° C., preferably about 20° C. to about 150° C., and the reaction time is generally about 0.5 hr to about 48 hr, preferably about 0.5 hr to about 24 hr.

The conversion of the imine or iminium ion to compound (I'd) can be performed according to various reduction reaction in a solvent inert to the reaction. The reduction reaction can be performed according to a method known per se, and examples thereof include a method using a metal hydride, and method employing hydrogenation reaction.

Examples of the metal hydride include sodium borohydride, lithium borohydride, zinc borohydride, sodium cyanoborohydride, sodium triacetoxyborohydride, lithium cyanoborohydride, dibutylaluminium hydride, aluminium hydride, lithium aluminium hydride, borane complexs (borane-THF complex, catecholborane etc.) and the like, and sodium borohydride, sodium cyanoborohydride, sodium triacetoxyborohydride and the like are preferable. The amount of the metal hydride to be used is, for example, about 1 to about 50 mol, preferably about 1 to about 10 mol, per 1 mol of the imine.

The reduction reaction using a metal hydride is performed generally in a solvent inert to the reaction. Examples of the solvent include aromatic hydrocarbons (toluene, xylene etc.), aliphatic hydrocarbons (heptane, hexane etc.), halogenated hydrocarbons (chloroform, dichloromethane etc.), ethers (diethyl ether, tetrahydrofuran, dioxane etc.), alcohols (methanol, ethanol, 2-propanol, butanol, benzyl alcohol etc.), nitriles (acetonitrile etc.), N,N-dimethylformamide, dimethylsulfoxide and the like. These solvent may be used in a mixture thereof in an appropriate ratio.

The reaction temperature is generally about −80° C. to about 80° C., preferably about −40° C. to about 40° C., and the reaction time is generally about 5 min to about 48 hr, preferably about 1 hr to about 24 hr.

The catalytic hydrogenation reaction can be performed in the presence of a catalyst under hydrogen atmosphere. Examples of the catalyst include palladiums such as palladium on carbon, palladium hydroxide on carbon, palladium oxide and the like; nickels such as Raney-nickel catalyst and the like; platinums such as platinum oxide, platinum on carbon and the like; rhodiums such as rhodium on carbon and the like, and the like. The amount thereof to be used is generally about 0.001 to about 1 mol, preferably about 0.01 to about 0.5 mol, per 1 mol of the imine or oxime.

The catalytic hydrogenation reaction is performed generally in a solvent inert to the reaction. Examples of the solvent include alcohols (methanol, ethanol, propanol, butanol etc.), hydrocarbons (benzene, toluene, xylene etc.), halogenated hydrocarbons (dichloromethane, chloroform etc.), ethers (diethyl ether, dioxane, tetrahydrofuran etc.), esters (ethyl acetate etc.), amides (N,N-dimethylformamide etc.), carboxylic acids (acetic acid etc.), water and mixtures thereof.

The hydrogen pressure for the reaction is generally about 1 to about 50 atm, preferably about 1 to about 10 atm. The reaction temperature is generally about 0° C. to about 150° C., preferably about 20° C. to about 100° C., and the reaction time is generally about 5 min to about 72 hr, preferably about 0.5 hr to about 40 hr.

In this step, by subjecting the intermediate imine or oxime without isolation to the next reduction reaction, compound (I'd) can also be obtained directly from compound (XI). In this case, the pH of the reaction mixture is preferably adjusted to about 4 to about 5.

[Method C]

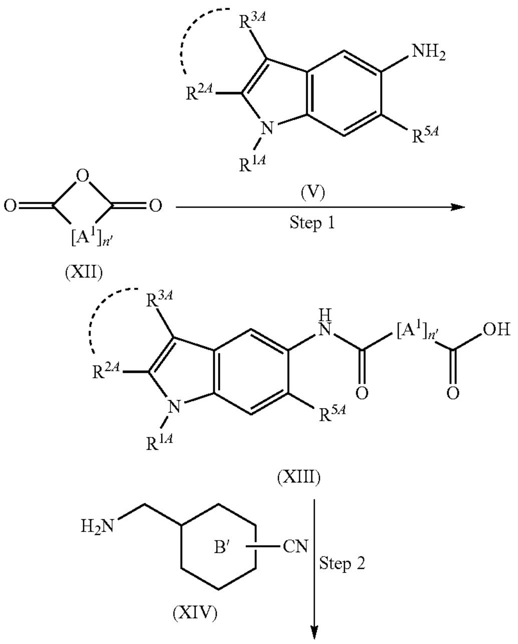

-continued

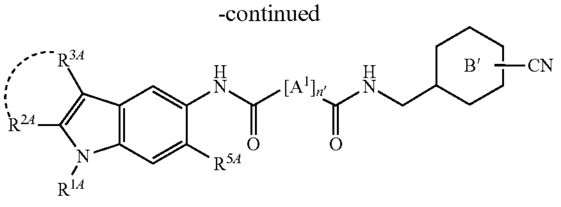

(I'e)

wherein each symbol is as defined above.

(Step 1)

This step is a step of producing compound (XIII) or a salt thereof by reacting compound (XII) or a salt thereof with compound (V) or a salt thereof.

This step can be performed in the same manner as in the method described in Step 1 of Method A.

Compound (XII) may be a commercially available product, or can also be produced according to a method known per se or a method analogous thereto.

(Step 2)

This step is a step of producing compound (I'e) or a salt thereof by reacting compound (XIII) or a salt thereof with compound (XIV) or a salt thereof in the presence of a condensing agent.

This step can be performed in the same manner as in the method described in Step 2 of Method A.

Compound (XIV) may be a commercially available product, or can also be produced according to a method known per se or a method analogous thereto.

[Method D]

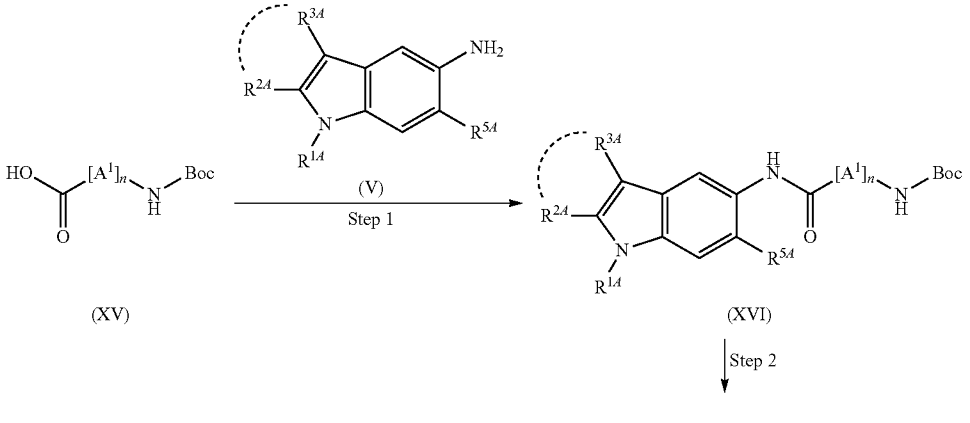

-continued

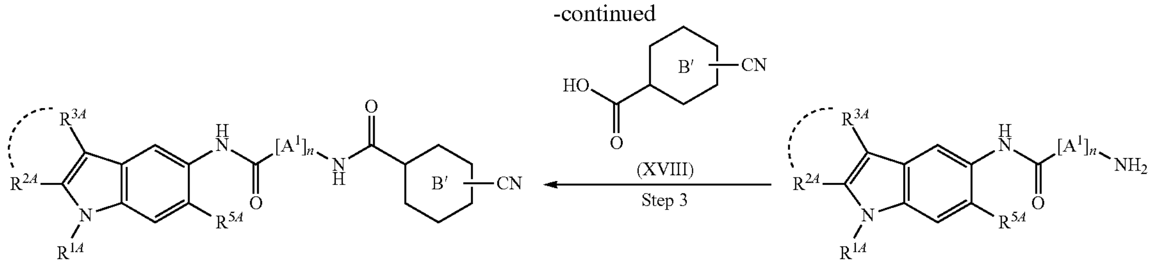

(I'f) (XVII)

wherein each symbol is as defined above.

(Step 1)

This step is a step of producing compound (XVI) or a salt thereof by reacting compound (XV) or a salt thereof with compound (V) or a salt thereof in the presence of a condensing agent.

This step can be performed in the same manner as in the method described in Step 2 of Method A.

Compound (XV) may be a commercially available product, or can also be produced according to a method known per se or a method analogous thereto.

(Step 2)

This step is a step of producing compound (XVII) or a salt thereof by subjecting compound (XVI) or a salt thereof to a deprotection reaction.

The deprotection reaction can be performed according to a known method (e.g., Wiley-Interscience, 1999, “Protective Groups in Organic Synthesis, 3rd Ed.” (Theodora W. Greene, Peter G. m. Wuts)). For example, while the reaction is performed depending on the kind of compound (XVI), it is generally performed in the presence of an acid, where necessary, in a solvent that does not adversely influence the reaction.

Examples of the acid include mineral acids (hydrochloric acid, hydrobromic acid, sulfuric acid, hydrogen chloride etc.), carboxylic acids (acetic acid, trifluoroacetic acid, trichloroacetic acid etc.), sulfonic acids (methanesulfonic acid, p-toluenesulfonic acid etc.), Lewis acids (aluminium chloride, tin chloride, zinc bromide etc.) and the like. The acid may be used in a mixture of two or more kinds thereof. While the amount of the acid to be used varies depending on the kind of the solvent and the other reaction condition, it is generally about 0.1 mol equivalent or more per 1 mol of compound (XVI). The acid may be used as a solvent.

Examples of the solvent that does not adversely influence the reaction include alcohols (methanol, ethanol, propanol, 2-propanol, butanol, isobutanol, t-butanol etc.), aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), carboxylic acids (acetic acid etc.), amides (N,N-dimethylformamide etc.), sulfoxides (dimethylsulfoxide etc.), water and the like, and mixed solvents thereof.

The reaction temperature is, for example, within about −50 to 200° C., preferably about 0 to 100° C. While the reaction time varies depending on the kind of compound (XVI), the reaction temperature and the like, it is, for example, about 0.5 to 100 hr, preferably about 0.5 to 24 hr.

(Step 3)

This step is a step of producing compound (I'f) or a salt thereof by reacting compound (XVII) or a salt thereof with compound (XVIII) or a salt thereof in the presence of a condensing agent.

This step can be performed in the same manner as in the method described in Step 2 of Method A.

Compound (XVIII) may be a commercially available product, or can also be produced according to a method known per se or a method analogous thereto.

[Method E]

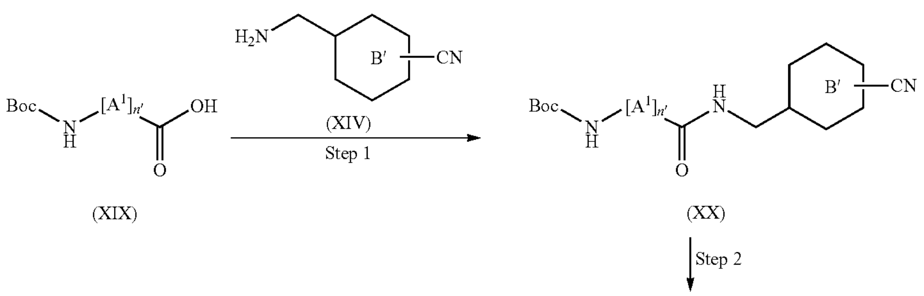

-continued

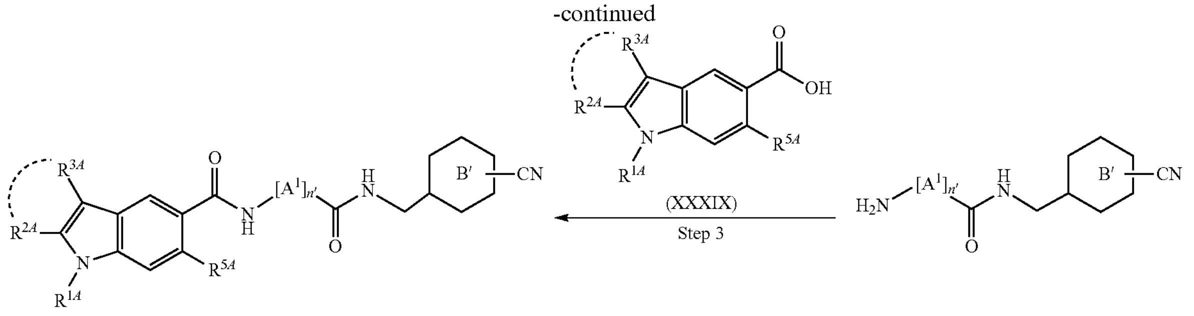

(I'g) (XXI)

wherein each symbol is as defined above.

(Step 1)

This step is a step of producing compound (XX) or a salt thereof by reacting compound (XIX) or a salt thereof with compound (XIV) or a salt thereof in the presence of a condensing agent.

This step can be performed in the same manner as in the method described in Step 2 of Method A.

(Step 3)

This step is a step of producing compound (I'g) or a salt thereof by reacting compound (XXI) or a salt thereof with compound (V) or a salt thereof in the presence of a condensing agent.

This step can be performed in the same manner as in the method described in Step 2 of Method A.

[Method F]

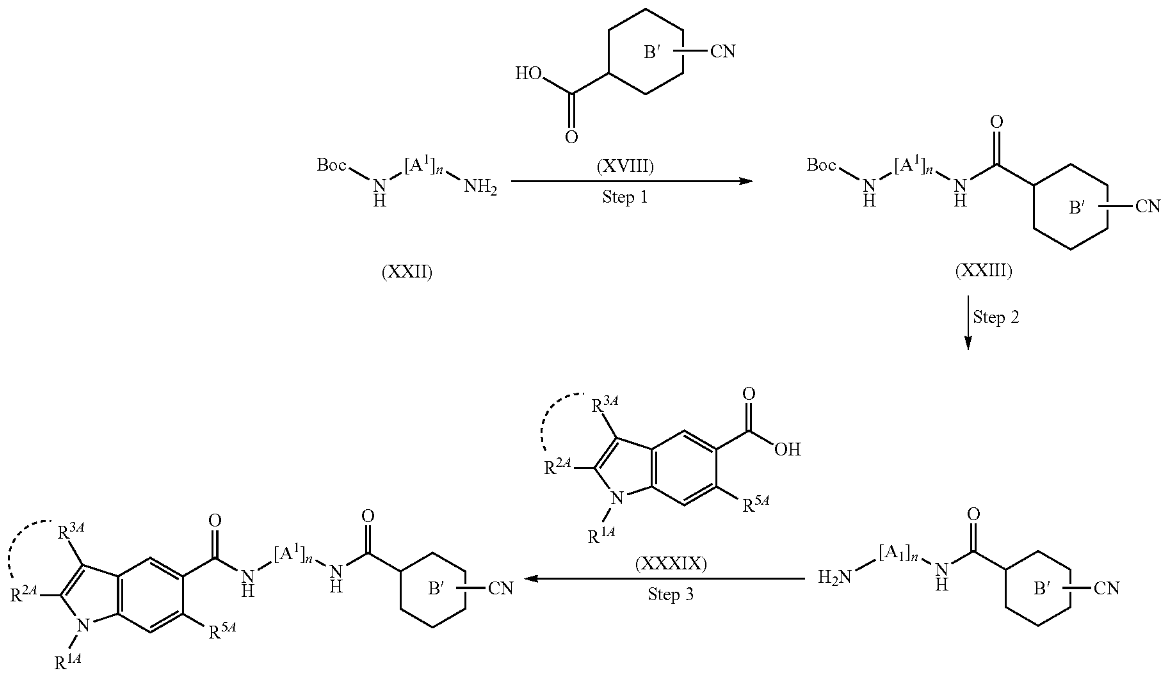

(XXII) (XXIII) (I'h) (XXIV)

Compound (XIX) may be a commercially available product, or can also be produced according to a method known per se or a method analogous thereto.

(Step 2)

This step is a step of producing compound (XXI) or a salt thereof by subjecting compound (XX) or a salt thereof to a deprotection reaction.

This step can be performed in the same manner as in the method described in Step 2 of Method D.

wherein each symbol is as defined above.

(Step 1)

This step is a step of producing compound (XXIII) or a salt thereof by reacting compound (XXII) or a salt thereof with compound (XVIII) or a salt thereof in the presence of a condensing agent.

This step can be performed in the same manner as in the method described in Step 2 of Method A.

Compound (XXII) may be a commercially available product, or can also be produced according to a method known per se or a method analogous thereto.

(Step 2)

This step is a step of producing compound (XXIV) or a salt thereof by subjecting compound (XXIII) or a salt thereof to a deprotection reaction.

This step can be performed in the same manner as in the method described in Step 2 of Method D.

(Step 3)

This step is a step of producing compound (I'h) or a salt thereof by reacting compound (XXIV) or a salt thereof with compound (XXXIX) or a salt thereof in the presence of a condensing agent.

This step can be performed in the same manner as in the method described in Step 2 of Method A.

[Method G]

1 to 10 mol equivalent, preferably about 1 to 5 mol equivalent, per 1 mol of compound (XXII).

The amount of compound (XXV) to be used is generally about 1 to 10 mol equivalent, preferably about 1 to 3 mol equivalent, per 1 mol of compound (XXII).

This reaction is generally performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide

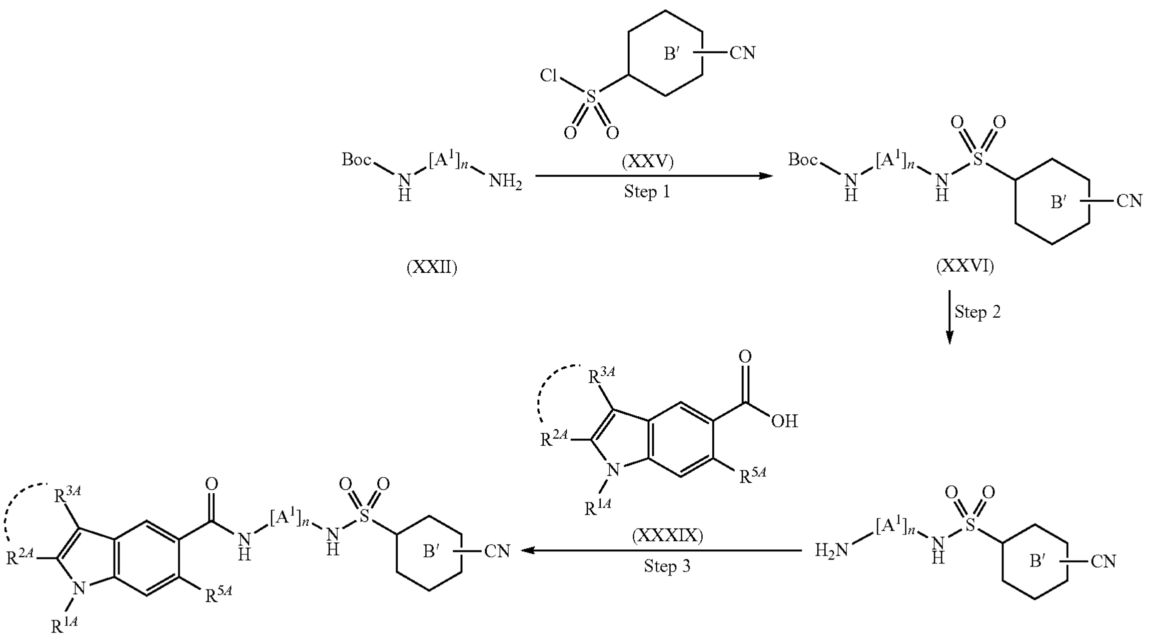

(XXII) (XXVI) (XXVII) (I'i)

wherein each symbol is as defined above.

(Step 1)

This step is a step of producing compound (XXVI) or a salt thereof by reacting compound (XXII) or a salt thereof with compound (XXV) or a salt thereof in the presence of a base.

Compound (XXV) may be a commercially available product, or can also be produced according to a method known per se or a method analogous thereto.

Examples of the base used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. While the amount of the base to be used varies depending on the kind of the solvent and other reaction condition, it is generally about etc.), sulfoxides (dimethylsulfoxide etc.) and the like. Among these, tetrahydrofuran, acetonitrile and N,N-dimethylformamide are preferable. These solvent may be used in a mixture of two or more kinds thereof in an appropriate ratio.

The reaction temperature is, for example, within about 0 to 200° C., preferably about 50 to 100° C. While the reaction time varies depending on the kind of compound (XXII) or a salt thereof, the reaction temperature and the like, it is, for example, about 0.5 to 100 hr, preferably about 0.5 to 24 hr.

(Step 2)

This step is a step of producing compound (XXVII) or a salt thereof by subjecting compound (XXVI) or a salt thereof to a deprotection reaction.

This step can be performed in the same manner as in the method described in Step 2 of Method D.

(Step 3)

This step is a step of producing compound (I'i) or a salt thereof by reacting compound (XXVII) or a salt thereof with compound (XXXIX) or a salt thereof in the presence of a condensing agent.

This step can be performed in the same manner as in the method described in Step 2 of Method A.

[Method H]

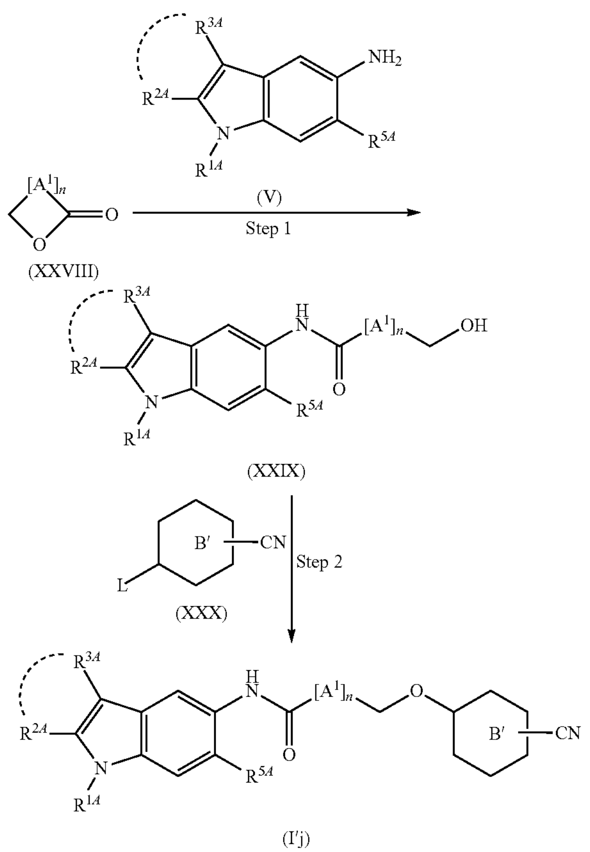

wherein each symbol is as defined above.

(Step 1)

This step is a step of producing compound (XXIX) or a salt thereof by reacting compound (XXVIII) or a salt thereof with compound (V) or a salt thereof in the presence of an additive.

Compound (XXVIII) may be a commercially available product, or can also be produced according to a method known per se or a method analogous thereto.

Examples of the additive used for this reaction include aluminium reagents (trimethylaluminum, aluminium chloride etc.), tin reagents (tetramethyltin etc.), Grignard reagents (methylmagnesium chloride, methylmagnesium bromide, methylmagnesium iodide, ethylmagnesium chloride, ethylmagnesium bromide, ethylmagnesium iodide etc.), bases (butyllithium, sodium hydride, sodium methoxide etc.) and the like. While the amount of the additive to be used varies depending on the kind of the solvent and the other reaction condition, it is generally about 1 to 10 mol equivalent, preferably about 1 to 5 mol equivalent, per 1 mol of compound (V).

The amount of compound (V) to be used is generally about 1 to 10 mol equivalent, preferably about 1 to 3 mol equivalent, per 1 mol of compound (XXVIII).

This reaction is generally performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.) and the like. These solvent may be used in a mixture of two or more kinds thereof in an appropriate ratio.

The reaction temperature is, for example, within about 0 to 200° C., preferably about 50 to 100° C. While the reaction time varies depending on the kind of compound (XXVIII) or a salt thereof, the kind of compound (V) or a salt thereof, the reaction temperature and the like, it is, for example, about 0.5 to 100 hr, preferably about 0.5 to 24 hr.

(Step 2)

This step is a step of producing compound (I'j) or a salt thereof by reacting compound (XXIX) or a salt thereof with compound (XXX) or a salt thereof in the presence of a base.

Compound (XXX) may be a commercially available product, or can also be produced according to a method known per se or a method analogous thereto.

Examples of the base used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide, potassium-t-butoxide and the like, etc.), organic bases (amines such as trimethylamine, triethylamine, diisopropylethylamine and the like, cyclic amines such as pyridine, 4-dimethylaminopyridine and the like etc.) and the like. Among these, sodium hydride and potassium-t-butoxide are preferable. While the amount of the base to be used varies depending on the kind of the solvent and other reaction condition, it is generally about 1 to 10 mol equivalent, preferably about 1 to 5 mol equivalent, per 1 mol of compound (XXIX).

The amount of compound (XXX) to be used is generally about 1 to 10 mol equivalent, preferably about 1 to 3 mol equivalent, per 1 mol of compound (XXIX).

This reaction is generally performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.) and the like. Among these, tetrahydrofuran is preferable. These solvent may be used in a mixture of two or more kinds thereof in an appropriate ratio.

The reaction temperature is, for example, within about 0 to 200° C., preferably about 50 to 100° C. While the reaction time varies depending on the kind of compound (XXIX) or a salt thereof, the reaction temperature and the like, it is, for example, about 0.5 to 100 hr, preferably about 0.5 to 24 hr.

[Method I]

This step can be performed in the same manner as in the method described in Step 2 of Method A.

Compound (XXXI) may be a commercially available product, or can also be produced according to a method known per se or a method analogous thereto.

(Step 2)

This step is a step of producing compound (XXXIII) or a salt thereof by reacting compound (XXXII) or a salt thereof with compound (VIIa) or a salt thereof in the presence of a base.

This step can be performed in the same manner as in the method described in Step 3 of Method A.

(Step 3)

This step is a step of converting compound (XXXIII) or a salt thereof to compound (XXXIV) or a salt thereof by hydrolysis.

This step can be performed in the same manner as in the method described in Step 6 of Method A.

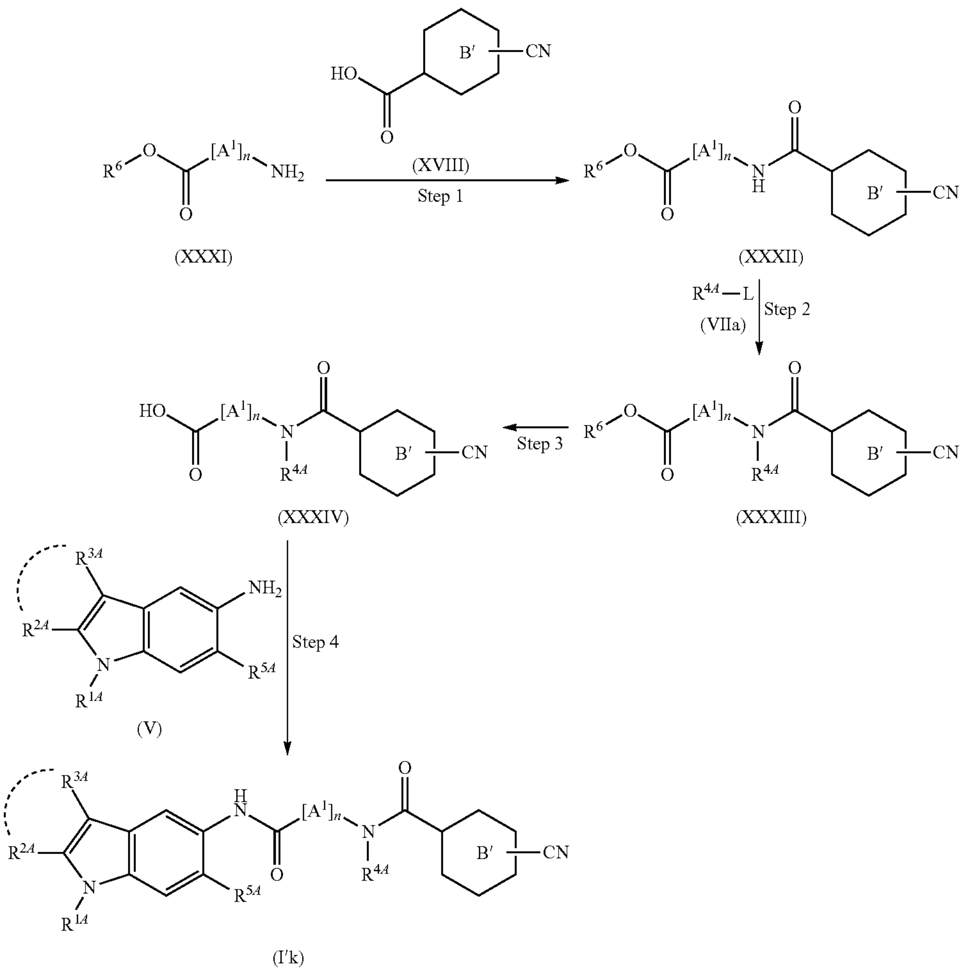

wherein each symbol is as defined above.

(Step 1)

This step is a step of producing compound (XXXII) or a salt thereof by reacting compound (XXXI) or a salt thereof with compound (XVIII) or a salt thereof in the presence of a condensing agent.

(Step 4)

This step is a step of producing compound (I'k) or a salt thereof by reacting compound (XXXIV) or a salt thereof with compound (V) or a salt thereof in the presence of a condensing agent.

This step can be performed in the same manner as in the method described in Step 2 of Method A.

[Method J]

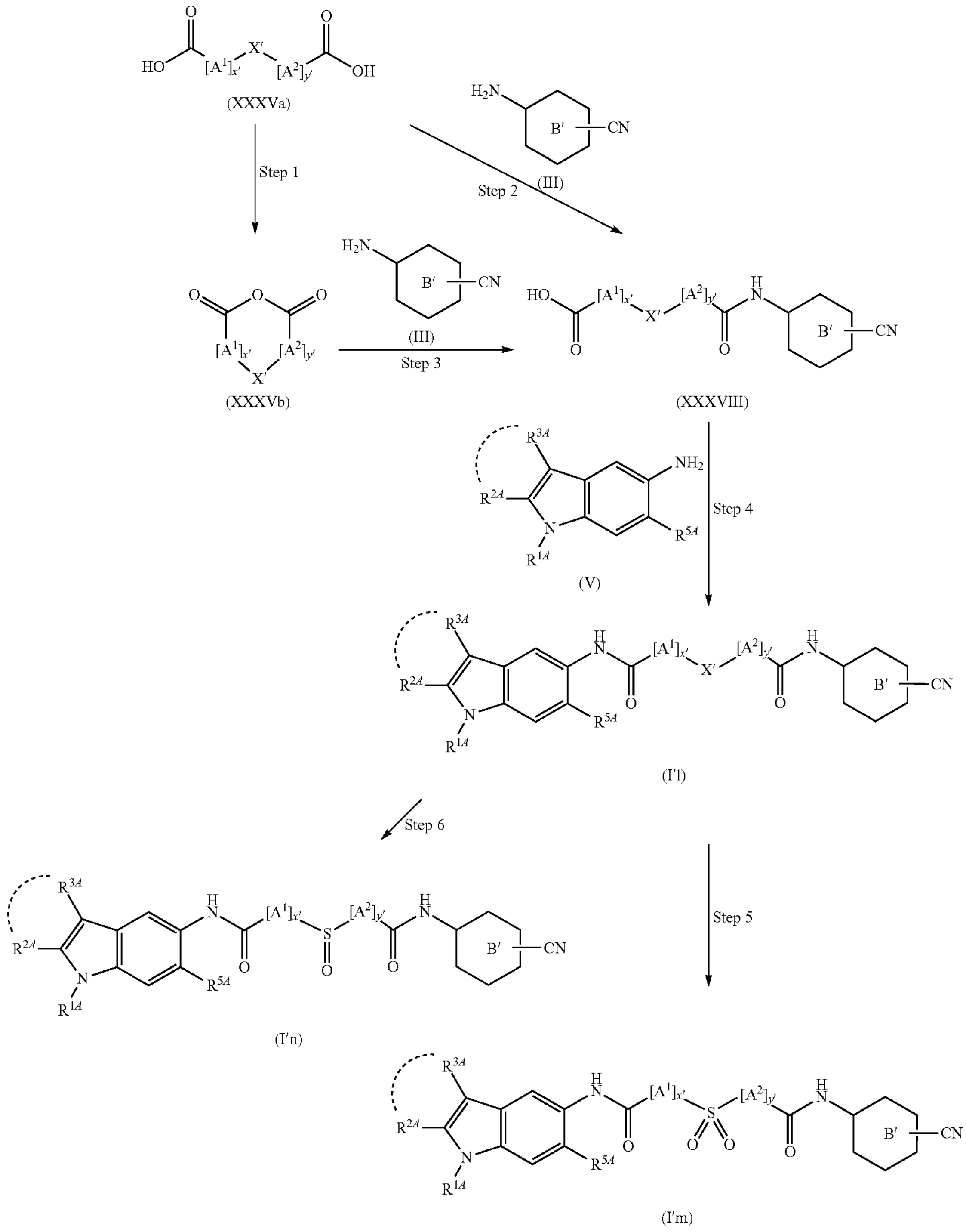

(XXXVa)
(III)
(XXXVb)
(XXXVIII)
(V)
(I'l)
(I'n)
(I'm)

wherein each symbol is as defined above.

(Step 1)

This step is a step of producing compound (XXXVb) or a salt thereof by subjecting compound (XXXVa) or a salt thereof to a dehydration reaction.

Compound (XXXVa) may be a commercially available product, or can also be produced according to a method known per se or a method analogous thereto.

Examples of the reactant used for this reaction include sulfuric acid, sulfonic acids (methanesulfonic acid, p-toluenesulfonic acid etc.), thionyl chloride, phosphoryl chloride, diphosphorus pentaoxide, phosgene, triphosgene, anhydrides (acetic anhydride, trifluoroacetic anhydride etc.) and the like. While the amount of the reactant to be used varies depending on the kind of the solvent and other reaction condition, it is generally about 1 to 100 mol equivalent, preferably about 1 to 10 mol equivalent, per 1 mol of compound (XXXVa).

This reaction is generally performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform, carbon tetrachloride etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.) and the like. These solvent may be used in a mixture of two or more kinds thereof in an appropriate ratio. The reactant may be used as a solvent.

The reaction temperature is, for example, within about 0 to 200° C., preferably about 50 to 100° C. While the reaction time varies depending on the kind of compound (XXXVa) or a salt thereof, the reaction temperature and the like, it is, for example, about 0.5 to 100 hr, preferably about 0.5 to 24 hr.

(Step 2)

This step is a step of producing compound (XXVIII) or a salt thereof by reacting compound (XXXVa) or a salt thereof with compound (III) or a salt thereof in the presence of a condensing agent.

This step can be performed in the same manner as in the method described in Step 2 of Method A.

(Step 3)

This step is a step of producing compound (XXXVIII) or a salt thereof by reacting compound (XXXVb) or a salt thereof with compound (III) or a salt thereof.

This step can be performed in the same manner as in the method described in Step 1 of Method A.

(Step 4)

This step is a step of producing compound (I' l) or a salt thereof by reacting compound (XXXVIII) or a salt thereof with compound (V) or a salt thereof in the presence of a condensing agent.

This step can be performed in the same manner as in the method described in Step 2 of Method A.

This step can be performed in the same manner as in the method described in Step 2 of Method A.

(Step 5)

This step is a step of producing compound (I'm) or a salt thereof by treating compound (I'l) or a salt thereof with an oxidizing agent.

Examples of the oxidizing agent used for this reaction include hydrogen peroxide, peracetic acid, periodates, metachloroperbenzoic acid, acyl nitrates, dinitrogen tetraoxide, halogen, N-halogen compounds (N-bromosuccinimide, N-chlorosuccinimide etc.) and the like. While the amount of the oxidizing agent to be used varies depending on the kind of the solvent and other reaction condition, it is generally about 1 to 10 mol equivalent, preferably about 1 to 10 mol equivalent, per 1 mol of compound (I'l).

This reaction is generally performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform, carbon tetrachloride etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.), water and the like. These solvent may be used in a mixture of two or more kinds thereof in an appropriate ratio. The oxidizing agent may be used as a solvent.

The reaction temperature is, for example, within about −78 to 200° C., preferably about 0 to 50° C. While the reaction time varies depending on the kind of compound (I'l) or a salt thereof, the reaction temperature and the like, it is, for example, about 0.5 to 500 hr, preferably about 0.5 to 24 hr.

(Step 6)

This step is a step of producing compound (I'n) or a salt thereof by treating compound (I'l) or a salt thereof with an oxidizing agent.

Examples of the oxidizing agent used for this reaction include hydrogen peroxide, peracetic acid, hydroperoxides, potassium peroxydisulfate, permanganates, sodium perborate, periodates, metachloroperbenzoic acid, osmium(VII) oxide, ruthenium(VII) oxide, nitric acid, chromic acid, sodium dichromate, halogens, sodium hypochlorite, iodobenzene dichloride, iodobenzene diacetate, ozone, singlet oxygen and the like. While the amount of the oxidizing agent to be used varies depending on the kind of the solvent and other reaction condition, it is generally about 1 to 10 mol equivalent, preferably about 1 to 10 mol equivalent, per 1 mol of compound (I'l).

This reaction is generally performed in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform, carbon tetrachloride etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (N,N-dimethylformamide etc.), sulfoxides (dimethylsulfoxide etc.), water and the like. These solvent may be used in a mixture of two or more kinds thereof in an appropriate ratio. The oxidizing agent may be used as a solvent.

The reaction temperature is, for example, within about −78 to 200° C., preferably about 0 to 50° C. While the reaction time varies depending on the kind of compound (I'l) or a salt thereof, the reaction temperature and the like, it is, for example, about 0.5 to 100 hr, preferably about 0.5 to 24 hr.

[Method K]

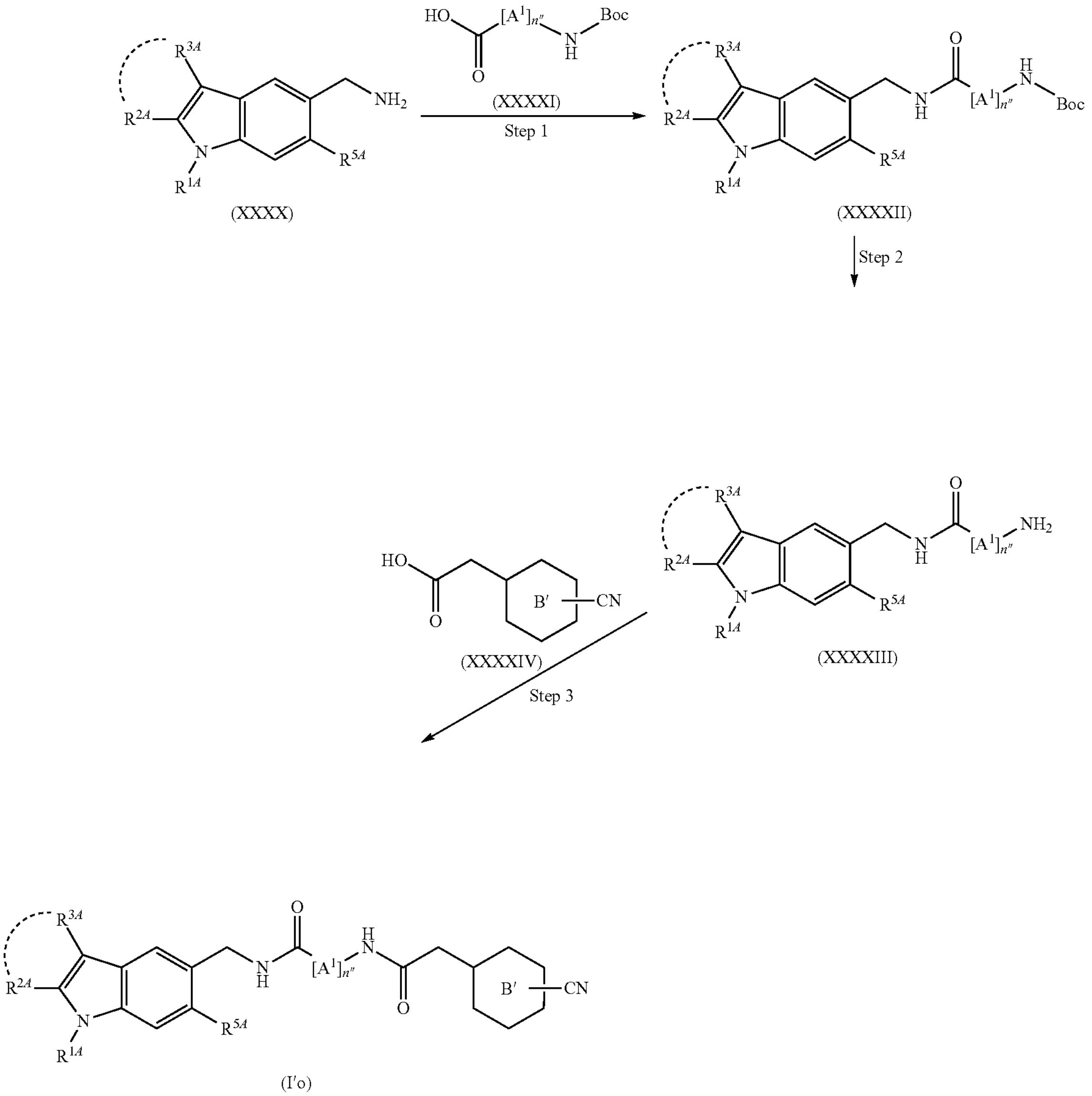

(XXXX) (XXXXI) (XXXXII) (XXXXIII) (XXXXIV) (I'o)

wherein each symbol is as defined above.

(Step 1)

This step is a step of producing compound (XXXXII) or a salt thereof by reacting compound (XXXX) or a salt thereof with compound (XXXXI) or a salt thereof in the presence of a condensing agent.

This step can be performed in the same manner as in the method described in Step 2 of Method A.

Compound (XXXX) and compound (XXXXI) may be a commercially available product, or can also be produced according to a method known per se or a method analogous thereto.

(Step 2)

This step is a step of producing compound (XXXXIII) or a salt thereof by subjecting compound (XXXXII) or a salt thereof to a deprotection reaction.

This step can be performed in the same manner as in the method described in Step 2 of Method D.

(Step 3)

This step is a step of producing compound (I'o) or a salt thereof by reacting compound (XXXXIII) or a salt thereof with compound (XXXXIV) or a salt thereof in the presence of a condensing agent.

This step can be performed in the same manner as in the method described in Step 2 of Method A.

Compound (XXXXIV) may be a commercially available product, or can also be produced according to a method known per se or a method analogous thereto.

[Method L]

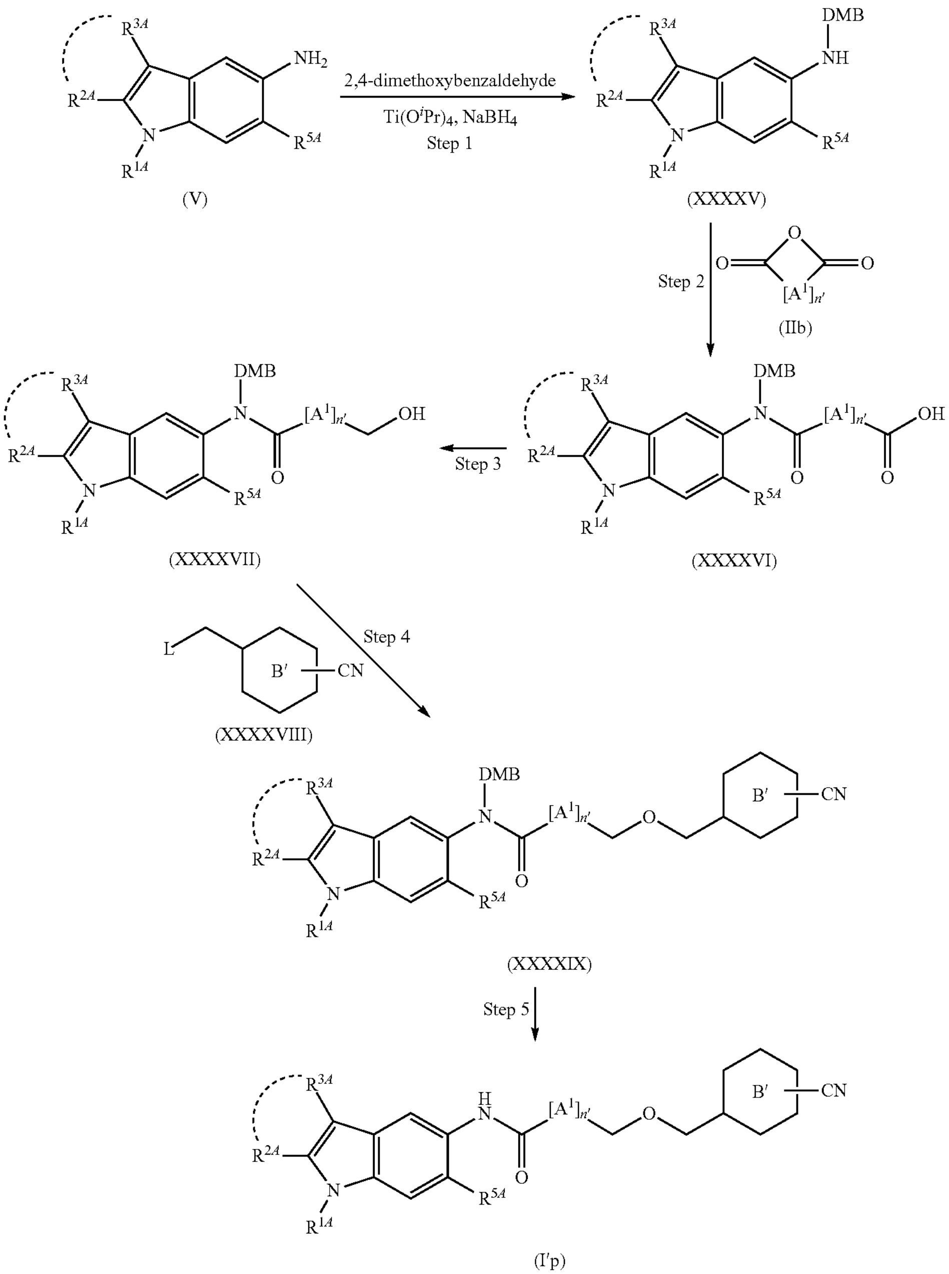

(V) (XXXXV) (IIb) (XXXXVII) (XXXXVI) (XXXXVIII) (XXXXIX) (I'p)

wherein DMB is a 2,4-dimethoxybenzyl group, and the other each symbols are as defined above.

(Step 1)

This step is a step of producing compound (XXXXV) or a salt thereof by subjecting compound (V) or a salt thereof to a reductive alkylation reaction with 2,4-dimethoxybenzaldehyde. The reductive alkylation reaction in this step can be performed according to a method known per se. For example, compound (XXXXV) or a salt thereof can be produced by reacting compound (V) or a salt thereof with 2,4-dimethoxybenzaldehyde in the presence of titanium(IV) isopropoxide, and subjecting the resulting imine to a reduction reaction with sodium borohydride.

The amount of the 2,4-dimethoxybenzaldehyde to be used is generally about 0.5 to 5 mol equivalent, preferably about 0.5 to 1 mol equivalent, per 1 mol of compound (V). The amount of the titanium(IV) isopropoxide to be used is generally about 1 to 10 mol equivalent, preferably about 1 to 3 mol equivalent, per 1 mol of compound (V).

The solvent used for the reaction for producing imine is not particularly limited as long as the reaction proceeds. Examples thereof include hydrocarbons (heptane, hexane, toluene, xylene etc.), halogenated hydrocarbons (chloroform, dichloromethane, 1,2-dichloroethane etc.), ethers (diethyl ether, tetrahydrofuran, dioxane etc.), esters (ethyl acetate, t-butyl acetate etc.), nitriles (acetonitrile, butyronitrile etc.), amides (N,N-dimethylformamide, dimethylacetamide etc.), sulfoxides (dimethylsulfoxide etc.) and the like, and mixed solvents thereof.

The reaction temperature is generally about 0° C. to about 200° C., preferably about 30° C. to about 150° C., and the reaction time is generally about 0.5 hr to about 48 hr, preferably about 0.5 hr to about 24 hr.

The amount of the sodium borohydride used for the reduction of the imine to be used is generally about 1 to 10 mol equivalent, preferably about 1 to 3 mol equivalent, per 1 mol of compound (V).

The reduction of the imine is performed generally in a solvent inert to the reaction. Examples of the solvent include aromatic hydrocarbons (toluene, xylene etc.), aliphatic hydrocarbons (heptane, hexane etc.), halogenated hydrocarbons (chloroform, dichloromethane etc.), ethers (diethyl ether, tetrahydrofuran, dioxane etc.), alcohols (methanol, ethanol, 2-propanol, butanol, benzyl alcohol etc.), nitriles (acetonitrile etc.), N,N-dimethylformamide, dimethylsulfoxide and the like. These solvent may be used in a mixture thereof in an appropriate ratio.

The reaction temperature is generally about −80° C. to about 80° C., preferably about −40° C. to about 40° C., and the reaction time is generally about 5 min to about 48 hr, preferably about 1 hr to about 24 hr.

(Step 2)

This step is a step of producing compound (XXXXVI) or a salt thereof by reacting compound (XXXXV) or a salt thereof with compound (IIb) or a salt thereof.

This step can be performed in the same manner as in the method described in Step 1 of Method A.

Compound (IIb) may be a commercially available product, or can also be produced according to a method known per se or a method analogous thereto.

(Step 3)

This step is a step of producing compound (XXXXVII) or a salt thereof by treating compound (XXXXVI) or a salt thereof with a reducing agent.

This step can be performed in the same manner as in the method described in Step 1 of Method B.

(Step 4)

This step is a step of producing compound (XXXXIX) or a salt thereof by reacting compound (XXXXVII) or a salt thereof with compound (XXXXVIII) or a salt thereof in the presence of a base.

This step can be performed in the same manner as in the method described in Step 2 of Method H.

Compound (XXXXVIII) may be a commercially available product, or can also be produced according to a method known per se or a method analogous thereto.

(Step 5)

This step is a step of producing compound (I'p) or a salt thereof by subjecting compound (XXXXIX) or a salt thereof to a deprotection reaction.

The deprotection reaction can be performed according to a known method (e.g., Wiley-Interscience, 1999, "Protective Groups in Organic Synthesis, 3rd Ed." (Theodora W. Greene, Peter G. m. Wuts)). For example, the deprotection reaction can be performed using anisole in trifluoroacetic acid as a solvent.

The amount of the trifluoroacetic acid to be used is generally 1 to 100 mL per 1 g of compound (XXXXIX). The amount of the anisole to be used is generally 1 to 10 mL per 1 g of compound (XXXXIX).

The reaction temperature is, for example, within about −50 to 100° C., preferably about 0 to 30° C. While the reaction time varies depending on the kind of compound (XXXXIX), the reaction temperature and the like, it is, for example, about 0.5 to 100 hr, preferably about 0.5 to 48 hr.

The production of compound (I') wherein the right bond of the bivalent group for Q' is bonded to the indole ring and the left bond thereof is bonded to Ring B', can be performed according to the method described in [Method A]-[Method L] mentioned above.

Compound (Ia)-compound (In) [compound (I) wherein Q in the formula (I) is each the bivalent group (Ia)-(In)] or a salt thereof of the present invention can be produced according to the above-mentioned Method A-Method J or a method analogous thereto.

When the object product is obtained in a free form by the above-mentioned reaction, it may be converted to a salt by a conventional method. When it is obtained as a salt, it can also be converted to a free form or other salt by a conventional method. The thus-obtained compound (I) or (I') can be isolated and purified from the reaction solution by a known means, for example, phase transfer, concentration, solvent extraction, fractionation, crystallization, recrystallization, chromatography and the like.

When compound (I) or (I') contains an isomer such as a tautomer, an optical isomer, a stereoisomer, a regioisomer, a rotamer and the like, any isomer and a mixture thereof are also encompassed in the compound of the present invention. Furthermore, when compound (I) or (I') has an optical isomer, an optical isomer resolved from this compound is also encompassed in compound (I) or (I').

The compound (I) or (I') may be a crystal. Even if compound (I) or (I') is in a single crystal form or mixed crystal form, it can be provided as compound (I) or (I') of the present invention.

Compound (I) or (I') may be a pharmaceutically acceptable co-crystal or co-crystal salt. Here, the co-crystal or co-crystal salt means a crystalline substance consisting of two or more particular substances which are solids at room temperature, each having different physical properties (e.g., structure, melting point, heat of melting, hygroscopicity, solubility, stability etc.). The co-crystal and co-crystal salt can be produced by co-crystallization known per se.

The compound (I) or (I') may be a solvate (e.g., a hydrate) or a non-solvate. Any of them can be provided as compound (I) or (I') of the present invention.

Any of the above compounds may be labeled or substituted with an isotope (e.g., $^{2}H$, $^{3}H$, $^{11}C$, $^{14}C$, $^{18}F$, $^{35}S$, $^{125}I$ etc.) and the like, and provided as compound (I) or (I') of the present invention. Compound (I) or (I') labeled or substituted with an isotope can be used, for example, as a tracer (PET tracer) used for positron emission tomography (PET), and is useful in the field such as medical diagnosis and the like.

The prodrug of compound (I) or (I') means a compound which can be converted into compound (I) or (I') by reaction with an enzyme, gastric acid, or the like under physiological conditions in the living body. In other words, it means a compound which can be converted into compound (I) or (I') by enzymatic oxidation, reduction, hydrolysis or the like, or a compound which can be converted into compound (I) or (I') by hydrolysis with gastric acid or the like. Examples of the prodrug of compound (I) or (I') include a compound in which amino of compound (I) or (I') is acylated, alkylated, or phosphorylated (e.g., the amino of compound (I) or (I') is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated etc.); a compound in which hydroxyl of compound (I) or (I') is acylated, alkylated, phosphorylated, or borated (e.g., hydroxyl of compound (I) or (I') is acetylated, palmitoylated, propanoylated, pivaloylated, succinylated, fumarylated, alanylated, dimethylaminomethylcarbonylated etc.); a compound in which carboxy of compound (I) or (I') is esterified or amidated (e.g., a compound in which carboxy of compound (I) or (I') is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated etc.). These compounds can be produced from compound (I) or (I') by a method known per se. The prodrug of compound (I) or (I') may be a compound that converts to compound (I) or (I') under physiological conditions as described in Development of Pharmaceutical Products, vol. 7, Molecule Design, 163-198, Hirokawa Shoten (1990).

Since compound (I) or (I') and a prodrug thereof [hereinafter sometimes to be abbreviated as the compound of the present invention] show superior RORγt inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt associated diseases, Th17 cell associated diseases and IL-17A or IL-17F associated diseases, more specifically, the diseases described in (1)-(4) below.

(1) inflammatory diseases (e.g., rheumatoid arthritis, acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis etc.), (2) autoimmune diseases (e.g., rheumatoid arthritis, ankylosing spondylitis, psoriasis, multiple sclerosis (MS), polymyositis, dermatomyositis (DM), polyarteritis nodosa (PN), mixed connective tissue disease (MCTD), Sjogren's syndrome nephritis, systemic lupus erythematosus, scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis (UC), Crohn's disease (CD), graft versus host disease, Addison's disease, abnormal immunoresponse, arthritis, dermatitis, radiodermatitis etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, non-hormone dependent prostate cancer and the like), liver cancer (e.g., primary liver cancer, extrahepatic bile duct cancer and the like), thyroid cancer (e.g., medullary thyroid carcinoma and the like), kidney cancer (e.g., renal cell carcinoma, transitional cell carcinoma in kidney and urinary duct and the like), uterine cancer, brain tumor (e.g., pineal astrocytoma, pilocytic astrocytoma, diffuse astrocytoma, anaplastic astrocytoma and the like), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary).

The medicament of the present invention can be used as a prophylactic or therapeutic agent for preferably autoimmune disease, inflammatory disease, bone or articular disease or neoplastic disease, particularly preferably, rheumatoid arthritis, inflammatory bowel disease, psoriasis, ankylosing spondylitis, bronchial asthma, chronic obstructive pulmonary diseases, ovarian cancer, non-small cell lung cancer, breast cancer, gastric cancer, cervical cancer, prostate cancer or uterine body cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation; sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I) or (I')) for one day, which is administered once to several times (e.g., once to 3 times).

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.

(1) Non-Steroidal Anti-Inflammatory Drug (NSAIDs)

(i) Classical NSAIDs alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

(ii) cyclooxygenase inhibitor (COX-1 selective inhibitor, COX-2 selective inhibitor and the like)

salicylic acid derivatives (e.g., celecoxib, aspirin), etoricoxib, valdecoxib, diclofenac, indomethacin, loxoprofen and the like.

(iii) nitric oxide-releasing NSAIDs (2) Disease-Modifying Anti-Rheumatic Drugs (DMARDs)

(i) Gold preparation auranofin and the like.

(ii) penicillamine

D-penicillamine.

(iii) aminosalicylic acid preparation sulfasalazine, mesalazine, olsalazine, balsalazide.

(iv) antimalarial drug chloroquine and the like.

(v) pyrimidine synthesis inhibitor leflunomide and the like.

(vi) prograf (3) Anti-Cytokine Drug (I) protein drug (i) TNF inhibitor etanercept, infliximab, adalimumab, certolizumab pegol, golimumab, PASSTNF-α, soluble TNF-α receptor, TNF-α binding protein, anti-TNF-α antibody and the like.

(ii) interleukin-1 inhibitor anakinra (interleukin-1 receptor antagonist), soluble interleukin-1 receptor and the like.

(iii) interleukin-6 inhibitor tocilizumab (anti-interleukin-6 receptor antibody), anti-interleukin-6 antibody and the like.

(iv) interleukin-10 drug interleukin-10 and the like.

(v) interleukin-12/23 inhibitor ustekinumab, briakinumab (anti-interleukin-12/23 antibody) and the like.

(II) non-protein drug (i) MAPK inhibitor

BMS-582949 and the like.

(ii) gene modulator inhibitor of molecule involved in signal transduction, such as NF-κ, NF-κB, IKK-1, IKK-2, AP-1 and the like, and the like.

(iii) cytokine production inhibitor iguratimod, tetomilast and the like.

(iv) TNF-α converting enzyme inhibitor (v) interleukin-1β converting enzyme inhibitor VX-765 and the like.

(vi) interleukin-6 antagonist

HMPL-004 and the like.

(vii) interleukin-8 inhibitor

IL-8 antagonist, CXCR1 & CXCR2 antagonist, reparixin and the like.

(viii) chemokine antagonist

CCR9 antagonist (CCX-282, CCX-025), MCP-1 antagonist and the like.

(ix) interleukin-2 receptor antagonist denileukin, diftitox and the like.

(x) therapeutic vaccines

TNF-α vaccine and the like.

(xi) gene therapy drug gene therapy drugs aiming at promoting the expression of gene having an anti-inflammatory action such as interleukin-4, interleukin-10, soluble interleukin-1 receptor, soluble TNF-α receptor and the like.

(xii) antisense compound

ISIS 104838 and the like.

(4) Integrin Inhibitor natalizumab, vedolizumab, AJM300, TRK-170, E-6007 and the like.

(5) Immunomodulator (Immunosuppressant)

methotrexate, cyclophosphamide, MX-68, atiprimod dihydrochloride, BMS-188667, CKD-461, rimexolone, cyclosporine, tacrolimus, gusperimus, azathiopurine, antilymphocyte serum, freeze-dried sulfonated normal immunoglobulin, erythropoietin, colony stimulating factor, interleukin, interferon and the like.

(6) Steroid dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.

(7) Angiotensin Converting Enzyme Inhibitor enalapril, captopril, ramipril, lisinopril, cilazapril, perindopril and the like.

(8) Angiotensin II Receptor Antagonist candesartan, cilexetil (TCV-116), valsartan, irbesartan, olmesartan, eprosartan and the like.

(9) Diuretic Drug hydrochlorothiazide, spironolactone, furosemide, indapamide, bendrofluazide, cyclopenthiazide and the like.

(10) Cardiotonic Drug digoxin, dobutamine and the like.

(11) β Receptor Antagonist carvedilol, metoprolol, atenolol and the like.

(12) Ca Sensitizer

MCC-135 and the like.

(13) Ca Channel Antagonist nifedipine, diltiazem, verapamil and the like.

(14) Anti-Platelet Drug, Anticoagulator heparin, aspirin, warfarin and the like.

(15) HMG-CoA Reductase Inhibitor atorvastatin, simvastatin and the like.

(16) Contraceptive (i) sex hormone or derivatives thereof gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.

(ii) antiestrogen ormeloxifene, mifepristone, Org-33628 and the like.

(iii) spermatocide ushercell and the like.

(17) Others (i) T cell inhibitors (ii) inosine monophosphate dehydrogenase (IMPDH) inhibitor mycophenolate mofetil and the like.

(iii) adhesion molecule inhibitor

ISIS-2302, selectin inhibitor, ELAM-1, VCAM-1, ICAM-1 and the like.

(iv) thalidomide (v) cathepsin inhibitor (vi) matrix metalloprotease (MMPs) inhibitor V-85546 and the like.

(vii) glucose-6-phosphate dehydrogenase inhibitor (viii) Dihydroorotate dehydrogenase (DHODH) inhibitor (ix)phosphodiesterase IV(PDE IV) inhibitor roflumilast, CG-1088 and the like.

(x) phospholipase $A_2$ inhibitor (xi) iNOS inhibitor

VAS-203 and the like.

(xii) microtubule stimulating drug paclitaxel and the like.

(xiii) microtuble inhibitor reumacon and the like.

(xiv) MHC class II antagonist (xv) prostacyclin agonist iloprost and the like.

(xvi) CD4 antagonist zanolimumab and the like.

(xvii) CD23 antagonist (xviii) LTB4 receptor antagonist

DW-1305 and the like.

(xix) 5-lipoxygenase inhibitor zileuton and the like.

(xx) cholinesterase inhibitor galanthamine and the like.

(xxi) tyrosine kinase inhibitor

Tyk2 inhibitor (WO2010142752) and the like.

(xxii) cathepsin B inhibitor (xxiii) adenosine deaminase inhibitor pentostatin and the like.

(xxiv) osteogenesis stimulator (xxv) dipeptidylpeptidase inhibitor (xxvi) collagen agonist (xxvii) capsaicin cream (xxviii) hyaluronic acid derivative synvisc (hylan G-F 20), orthovisc and the like.

(xxix) glucosamine sulfate (xxx) amiprilose (xxxi) CD-20 inhibitor rituximab, ibritumomab, tositumomab, ofatumumab and the like.

(xxxii) BAFF inhibitor belimumab, tabalumab, atacicept, A-623 and the like.

(xxxiii) CD52 inhibitor alemtuzumab and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent (i) sulfa drug sulfamethizole, sulfisoxazole, sulfamonomethoxine, sulfamethizole, salazosulfapyridine, silver sulfadiazine and the like.

(ii) quinolone antibacterial agent nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.

(iii) antiphthisic isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.

(iv) antiacidfast bacterium drug diaphenylsulfone, rifampicin and the like.

(v) antiviral drug idoxuridine, acyclovir, vidarabine, gancyclovir and the like.

(vi) anti-HIV agent zidovudine, didanosine, zalcitabine, indinavir sulfate ethanolate, ritonavir and the like.

(vii) antispirochetele (viii) antibiotic tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) Antifungal Agent (i) polyethylene antibiotic (e.g., amphotericin B, nystatin, trichomycin)

(ii) griseofulvin, pyrrolnitrin and the like (iii) cytosine metabolism antagonist (e.g., flucytosine)

(iv) imidazole derivative (e.g., econazole, clotrimazole, miconazole nitrate, bifonazole, croconazole)

(v) triazole derivative (e.g., fluconazole, itraconazole)

(vi) thiocarbamic acid derivative (e.g., trinaphthol) and the like.

(3) Antiprotozoal Agent metronidazole, tinidazole, diethylcarbamazine citrate, quinine hydrochloride, quinine sulfate and the like.

(4) Antitussive and Expectorant Drug ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic (6-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) General Anesthetic (i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) Antiulcer Drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) Antiarrhythmic Agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone),
(iv) calcium channel blocker (e.g., verapamil, diltiazem) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug

6-O-(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Antiepileptic Drug phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac Stimulants trans-π-oxocamphor, terephyllol, aminophylline, etilefrine, dopamine, dobutamine, denopamine, aminophylline, vesnarinone, amrinone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine denopamine and the like.

(22) Hypotensive Diuretic hexamethonium bromide, pentolinium, mecamylamine, ecarazine, clonidine, diltiazem, nifedipine and the like.

(23) Therapeutic Drug for Diabetes tolbutamide, chlorpropamide, acetohexamide, glibenclamide, tolazamide, acarbose, epalrestat, troglitazone, glucagon, glymidine, glipizide, phenformin, buformin, metformin and the like.

(24) Antinarcotic levallorphan, nalorphine, naloxone or a salt thereof and the like.

(25) Liposoluble Vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) Vitamin Derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.

(28) Therapeutic Agent for Pollakisuria/Anischuria flavoxate hydrochloride and the like.

(29) Therapeutic Agent for Atopic Dermatitis sodium cromoglicate and the like.

(30) Therapeutic Agent for Allergic Rhinitis sodium cromoglicate, chlorpheniramine maleate, alimemazine tartrate, clemastine fumarate, homochlorcyclizine hydrochloride, fexofenadine, mequitazine and the like.

(31) Hypertensor dopamine, dobutamine, denopamine, digitoxin, digoxin, methyldigoxin, lanatoside C, G-strophanthin and the like.

(32) Others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with inflammatory bowel disease (IBD), about 0.1 mg/kg body weight—about 30 mg/kg body weight, preferably about 1 mg/kg body weight-20 mg/kg body weight, of compound (I) or (I') can be administered once to several portions (e.g., once to 3 times) per day.

The dose of the pharmaceutical composition of the present invention as a sustained-release preparation varies depending on the kind and content of compound (I) or (I'), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I) or (I') needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times (preferably, once to 3-times) divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in more detail in the following by referring to Examples, Preparation Examples and Experimental Examples, which are not to be construed as limitative and may be modified without departing from the scope of the invention.

Unless particularly indicated, the elution in column chromatography in the Examples was performed under observation by TLC (Thin Layer Chromatography). For TLC observation, 60F254 manufactured by Merck was used as a TLC plate, and the solvent used as an elution solvent for column chromatography was used. For detection, moreover, a UV detector was adopted. As silica gel for column chromatography, silica gel 60 (70-230 mesh) manufactured by Merck was used. The room temperature generally means a temperature about 10° C. to 35° C. For drying extracts, sodium sulfate or magnesium sulfate was used.

The abbreviations in the Examples mean as follows.

LC: liquid chromatography
MS: mass analysis spectrum
API: atmospheric pressure ionization method
M: molecular weight of the compound NMR: nuclear magnetic resonance spectrum
Hz: hertz
J: coupling constant
m: multiplet
q: quartet
t: triplet
d: doublet
s: singlet
br: broad
dt: double triplet
ddd: double double doublet
brs: broad singlet
$^t$Bu: tert-butyl group
Boc: tert-butyloxycatbonyl group
N: normal concentration
THF: tetrahydrofuran
HOBt: 1H-benzo[d][1,2,3]triazol-1-ol hydrate
WSC: $N^1$-((ethylimino)methylene)-$N^3$,$N^3$-dimethylpropane-1,3-diamine hydrochloride
DMF: N,N-dimethylformamide
DMA: dimethylacetamide
DMSO: dimethylsulfoxide
DIEA: diisopropylethylamine
HATU: 2-(1H-7-azabenzotriazol-1-yl)-1,1,3,3-tetramethyluronium hexafluorophosphorate
TFA: trifluoroacetic acid
TEA: triethylamine
DMAP: dimethylaminopyridine
mCPBA: m-chloroperbenzoic acid
DBU: 1,8-diazabicyclo[5.4.0]undec-7-ene The purification by preparative HPLC in the Examples was performed under the following conditions.

equipment: Gilson Inc. High throughput purification system column: CombiPrep ODS-A S-5 μm, 50×20 mm (YMC)

solvent: SOLUTION A; 0.1% trifluoroacetic acid-containing water, SOLUTION B; 0.1% trifluoroacetic acid-containing acetonitrile gradient cycle: 0.00 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5)

flow rate: mL/min, detection method: UV 220 nm

Example 1

N-(2-cyanophenyl)-N'-(9-ethyl-9H-carbazol-3-yl)-3-methylpentanediamide (Step 1)

A solution of 2-aminobenzonitrile (1.181 g, 10 mmol) and 4-methyldihydro-2H-pyran-2,6(3H)-dione (1.281 g, 10 mmol) in THF (20 mL) was stirred at 90° C. for 46 hr. The reaction solution was concentrated to give 5-(2-cyanophenylamino)-3-methyl-5-oxopentanoic acid (2.230 g, 9.06 mmol, 91%) as a white powder.

$^1$H-NMR (300 MHz, DMSO-$d_6$): δ0.99 (3H, d, J=5.7 Hz), 2.08-2.22 (1H, m), 2.22-2.46 (4H, m), 7.30-7.41 (1H, m), 7.52 (1H, d, J=7.9 Hz), 7.63-7.73 (1H, m), 7.80 (1H, d, J=7.9 Hz), 10.16 (1H, s), 12.10 (1H, brs)

(Step 2)

A solution of 9-ethyl-9H-carbazol-3-amine (210 mg, 1.00 mmol), the compound obtained in Step 1 (239 mg, 0.97 mmol), HOBt (297 mg, 1.94 mmol) and WSC (372 mg, 1.94 mmol) in DMF (5 mL) was stirred at room temperature for 14 hr. The reaction mixture was poured into a mixed solution of aqueous sodium hydrogen carbonate solution and ethyl acetate, and the precipitate was collected by filtration, and recrystallized from methanol and THF to give the title compound (172 mg, 0.392 mmol, 40.4%) as a white powder.

$^1$H-NMR (300 MHz, DMSO-$d_6$): δ1.08 (3H, d, J=6.4 Hz), 1.30 (3H, d, J=7.2 Hz), 2.23-2.47 (5H, m), 4.41 (2H, d, J=7.2 Hz), 7.13-7.22 (1H, m), 7.32-7.40 (1H, m), 7.40-7.49 (1H, m), 7.51-7.62 (4H, m), 7.64-7.73 (1H, m), 7.77-7.87 (1H, m), 8.05 (1H, d, J=7.5 Hz), 8.43 (1H, s), 9.85-10.35 (2H, m)

Example 2

N-(3-cyanophenyl)-N'-(9-ethyl-9H-carbazol-3-yl)-3-methylpentanediamide (Step 1)

Using 3-aminobenzonitrile, and by the reaction and purification in the same manner as in the method described in Step 1 of Example 1, 5-(3-cyanophenylamino)-3-methyl-5-oxopentanoic acid was obtained.

$^1$H-NMR (300 MHz, DMSO-$d_6$): δ0.96 (3H, d, J=6.0 Hz), 2.05-2.45 (5H, m), 7.43-7.62 (2H, m), 7.78 (1H, dt, J=6.7, 2.3 Hz), 8.10 (1H, s), 10.25 (1H, s), 12.10 (1H, brs)

(Step 2)

A solution of 9-ethyl-9H-carbazol-3-amine (210 mg, 1.00 mmol), the compound obtained in Step 1 (246 mg, 1 mmol), HOBt (306 mg, 2.00 mmol) and WSC (383 mg, 2.00 mmol) in DMF (5 mL) was stirred at room temperature for 14 hr. The reaction mixture was poured into a mixed solution of aqueous sodium hydrogen carbonate solution and ethyl acetate, and the organic layer was separated. The organic layer was washed with water and saturated brine, and dried, and the solvent was evaporated under reduced pressure. The obtained residue was purified by silica gel column chromatography (solvent gradient; 66 to 80% ethyl acetate/hexane) to give the title compound (283 mg, 0.645 mmol, 64.5%) as a white powder.

$^1$H-NMR (300 MHz, DMSO-$d_6$): δ1.03 (3H, d, J=6.0 Hz), 1.23-1.34 (3H, m), 2.23-2.50 (5H, m), 2.72-2.83 (1H, m), 4.41 (1H, d, J=7.2 Hz), 7.13-7.23 (1H, m), 7.52 (7 Hd, J=12.1 Hz), 8.04 (1H, d, J=7.5 Hz), 8.13 (1H, s), 8.41 (1H, s), 9.93 (1H, s), 10.25-10.34 (1H, m)

Example 3

N-(4-cyanophenyl)-N'-(1-ethyl-2,3-dimethyl-1H-indol-5-yl)-3-methylpentanediamide (Step 1)

A solution of 4-aminobenzonitrile (4.61 g, 39.02 mmol) and 4-methyldihydro-2H-pyran-2,6(3H)-dione (5.0 g, 39.02 mmol) in THF (50 mL) was stirred at 90° C. for 14 hr. The reaction solution was concentrated, and the precipitate was washed with ethyl acetate to give 5-(4-cyanophenylamino)-3-methyl-5-oxopentanoic acid (6.23 g, 25.3 mmol, 64.8%).

$^1$H-NMR (300 MHz, DMSO-$d_6$): δ0.96 (3H, d, J=6.0 Hz), 2.01-2.21 (1H, m), 2.21-2.47 (4H, m), 7.62-7.90 (4H, m), 10.34 (1H, s), 12.11 (1H, brs)

(Step 2)

To a solution of the compound obtained in Step 1 (510 mg, 2.07 mmol), 1-ethyl-2,3-dimethyl-1H-indol-5-amine (390 mg, 2.07 mmol) and DIEA (1.085 mL, 6.21 mmol) in DMF (8 mL) was added HATU (1181 mg, 3.11 mmol), and the mixture was stirred at room temperature for 14 hr. The reaction mixture was poured into water, and extracted with ethyl acetate. The organic layer was separated, washed with water and saturated brine, and dried, and the solvent was evaporated under reduced pressure. The obtained residue was purified by silica gel column chromatography (solvent gradient; 10 to 100% ethyl acetate/hexane) to give the title compound (533 mg, 1.280 mmol, 61.8%) as a white powder.

$^1$H-NMR (300 MHz, DMSO-$d_6$): δ1.00 (3H, d, J=6.4 Hz) 1.18 (3H, t, J=7.2 Hz), 2.13 (3H, s), 2.17-2.43 (5H, m), 2.43-2.61 (3H, m), 4.09 (2H, q, J=6.9 Hz), 7.05-7.35 (2H, m), 7.64-7.89 (5H, m), 9.68 (1H, s), 10.37 (1H, s)

MS (API): 417 (M+H)

Example 4

N-(4-cyanophenyl)-N'-(9-ethyl-2,3,4,9-tetrahydro-1H-carbazol-6-yl)-3-methylpentanediamide To a solution of 5-(4-cyanophenylamino)-3-methyl-5-oxopentanoic acid (172 mg, 0.70 mmol), 9-ethyl-2,3,4,9-tetrahydro-1H-carbazol-6-amine (150 mg, 0.70 mmol) and DIEA (0.367 mL, 2.10 mmol) in DMF (8 mL) was added HATU (399 mg, 1.05 mmol), and the mixture was stirred at room temperature for 14 hr. The reaction mixture was poured into water, and extracted with ethyl acetate. The organic layer was separated, washed with water and saturated brine, and dried, and the solvent was evaporated under reduced pressure. The obtained residue was purified by silica gel column chromatography (solvent gradient; 10 to 100% ethyl acetate/hexane) to give the title compound (179 mg, 0.404 mmol, 57.8%) as a white powder.

$^1$H-NMR (300 MHz, DMSO-$d_6$): δ0.99 (3H, d, J=6.1 Hz), 1.19 (3H, t, J=7.2 Hz), 1.65-1.94 (4H, m), 2.16-2.41 (3H, m), 2.41-2.48 (2H, m), 2.57 (2H, t, J=5.3 Hz), 2.63-2.72 (2H, m), 4.04 (2H, q, J=7.2 Hz), 7.16 (1H, dd, J=8.7, 1.9 Hz), 7.26 (1H, d, J=8.7 Hz), 7.62-7.87 (5H, m), 9.68 (1H, s), 10.37 (1H, s)

MS (API): 443 (M+H)

Example 5

N-(4-cyanophenyl)-5-[(9-ethyl-9H-carbazol-3-yl)amino]-3-methylpentanamide (Step 1)

To a solution of 5-(4-cyanophenylamino)-3-methyl-5-oxopentanoic acid (1.00 g, 4.06 mmol) in THF (15 mL) was added borane-THF complex (1.2M, THF solution 6.77 mL, 8.12 mmol) under ice-cooling. The mixture was stirred at room temperature for 14 hr, and the reaction mixture was poured into water. The mixture was extracted with ethyl acetate, the organic layer was washed with water and saturated brine, and dried, and the solvent was evaporated under reduced pressure. The obtained residue was purified by silica gel column chromatography (solvent gradient; 10 to 100% ethyl acetate/hexane) to give N-(4-cyanophenyl)-5-hydroxy-3-methylpentanamide (0.442 g, 1.904 mmol, 46.9%) as a colorless oil.

$^1$H-NMR (300 MHz, $CDCl_3$): δ1.06 (3H, d, J=6.8 Hz), 1.52-1.72 (2H, m), 2.14-2.53 (4H, m), 3.66-3.94 (2H, m), 7.49-7.79 (4H, m), 8.46 (1H, brs)

(Step 2)

To a solution of the compound obtained in Step 1 (435 mg, 1.87 mmol) in acetonitrile (10 mL) was added Dess-Martin Periodinane (953 mg, 2.25 mmol), and the mixture was stirred at room temperature for 2 hr. The reaction mixture was poured into aqueous sodium thiosulfate solution, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 80% ethyl acetate/hexane) to give crude N-(4-cyanophenyl)-3-methyl-5-oxopentanamide (113 mg, 0.492 mmol, 26.3%) as a white powder.

MS (API): 229 (M−H)

(Step 3)

A solution of the compound obtained in Step 2 (110 mg, 0.48 mmol) and 3-amino-N-ethylcarbazole (151 mg, 0.72 mmol) in TFA (1 mL) and toluene (1 mL) was stirred at room temperature for 1 hr. To the reaction mixture was added sodium triacetoxyborohydride (304 mg, 1.43 mmol), and the mixture was stirred at room temperature for additional 14 hr. The reaction mixture was concentrated under reduced pressure, and the residue was dissolved in ethyl acetate. The solution was washed with 1N aqueous sodium hydroxide solution, water and saturated brine, and dried, and the solvent was evaporated under reduced pressure. The obtained residue was purified by silica gel column chromatography (solvent gradient; 10 to 80% ethyl acetate/hexane) to give the title compound (82 mg, 0.193 mmol, 40.5%) as a pale-yellow powder.

$^1$H-NMR (300 MHz, DMSO-$d_6$): δ0.97-1.08 (3H, m), 1.26 (3H, t, J=7.0 Hz), 1.49-1.63 (1H, m), 1.66-1.80 (1H, m), 2.13-2.34 (2H, m), 2.41-2.48 (1H, m), 3.15 (2H, brs), 4.31 (2H, q, J=6.7 Hz), 5.15 (1H, brs), 6.83-6.88 (1H, m), 7.07 (1H, t, J=7.2 Hz), 7.24 (1H, s), 7.29-7.37 (2H, m), 7.43-7.53 (1H, m), 7.71-7.84 (4H, m), 7.96 (1H, d, J=7.6 Hz), 10.34 (1H, s)

Example 6

N-(4-cyanophenyl)-N'-(9-ethyl-9H-carbazol-3-yl)-3,3-dimethylpentanediamide (Step 1)

Using 4,4-dimethyldihydro-2H-pyran-2,6(3H)-dione, and by the reaction and purification in the same manner as in the method described in Step 1 of Example 3, 5-(4-cyanophenylamino)-3,3-dimethyl-5-oxopentanoic acid was obtained.

MS (API): 259 (M−H)

(Step 2)

Using the compound obtained in Step 1, and by the reaction and purification in the same manner as in the method described in Step 2 of Example 1, the title compound was obtained.

$^1$H-NMR (300 MHz, $CDCl_3$): δ1.06-1.33 (6H, m), 1.42 (3H, t, J=7.2 Hz), 2.45 (2H, s), 2.56 (2H, s), 4.36 (2H, q, J=7.2 Hz), 7.12-7.32 (1H, m), 7.32-7.66 (6H, m), 7.76 (2H, d, J=8.7 Hz), 7.94 (1H, s), 8.08 (1H, d, J=7.9 Hz), 8.25 (1H, d, J=1.5 Hz), 10.56 (1H, s)

Example 7

2-(1-{2-[(4-cyanophenyl)amino]-2-oxoethyl}cyclopentyl)-N-(9-ethyl-9H-carbazol-3-yl)acetamide (Step 1)

Using 8-oxaspiro[4.5]decane-7,9-dione, and by the reaction and purification in the same manner as in the method described in Step 1 of Example 3, 2-(1-(2-(4-cyanophenylamino)-2-oxoethyl)cyclopentyl)acetic acid was obtained.

MS (API): 285 (M−H)

(Step 2)

Using the compound obtained in Step 1, and by the reaction and purification in the same manner as in the method described in Step 2 of Example 1, the title compound was obtained.

$^1$H-NMR (300 MHz, $CDCl_3$): δ1.43 (3H, t, J=7.2 Hz), 1.51-1.70 (3H, m), 1.70-1.95 (5H, m), 2.52 (2H, s), 2.60 (2H, s), 4.37 (2H, q, J=7.2 Hz), 7.16-7.31 (1H, m), 7.34-7.63 (6H, m), 7.67-7.89 (3H, m), 8.09 (1H, d, J=7.5 Hz), 8.24 (1H, d, J=1.9 Hz), 10.47 (1H, s)

Example 8

N-benzyl-N-(4-cyanophenyl)-N'-(9-ethyl-9H-carbazol-3-yl)-3-methylpentanediamide (Step 1)

A solution of 5-(4-cyanophenylamino)-3-methyl-5-oxopentanoic acid (940 mg, 3.82 mmol) and conc. sulfuric acid (1 drop) in methanol (25 mL) was heated with reflux for 14 hr. The reaction solution was cooled, and ethyl acetate was added thereto. The solution was washed with water and saturated brine, and dried, and the solvent was evaporated under reduced pressure. The obtained residue was purified by silica gel column chromatography (solvent gradient; 10 to 100% ethyl acetate/hexane) to give methyl 5-(4-cyanophenylamino)-3-methyl-5-oxopentanoate (557 mg, 2.139 mmol, 56.0%) as a white powder.

MS (API): 259 (M−H)

(Step 2)

To a solution of the compound obtained in Step 1 (228 mg, 0.88 mmol) in DMF (6 mL) was added sodium hydride (60% in oil, 126 mg, 2.63 mmol) at 0° C. The reaction mixture was stirred at room temperature for 30 min, and benzyl bromide (0.156 mL, 1.31 mmol) was added thereto at 0° C. The reaction mixture was stirred at room temperature for 14 hr, to the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 85% ethyl acetate/hexane) to give methyl 5-(benzyl(4-cyanophenyl)amino)-3-methyl-5-oxopentanoate (81 mg, 0.230 mmol, 26.3%) as a colorless oil.

MS (API): 351 (M+H)

(Step 3)

A solution of the compound obtained in Step 2 (80.0 mg, 0.23 mmol) and 1N aqueous sodium hydroxide solution (1 mL, 1.00 mmol) in methanol (2 mL) and THF (2 mL) was stirred at room temperature for 14 hr. The reaction solution was neutralized with 1N hydrochloric acid, and the mixture was extracted with ethyl acetate. The organic layer was washed with water and saturated brine, and dried, and the solvent was evaporated under reduced pressure to give crude 5-(benzyl(4-cyanophenyl)amino)-3-methyl-5-oxopentanoic acid (74.2 mg, 0.221 mmol, 97%) as a white powder.

MS (API): 335 (M−H)

(Step 4)

Used the compound obtained in Step 3, and by the reaction and purification in the same manner as in the method described in Step 2 of Example 1, the title compound was obtained.

$^1$H-NMR (300 MHz, DMSO-$d_6$): δ0.94 (3H, d, J=6.8 Hz), 1.30 (3H, t, J=7.2 Hz), 2.03-2.43 (4H, m), 4.41 (2H, q, J=6.8 Hz), 4.96 (2H, s), 7.09-7.33 (6H, m), 7.36-7.67 (6H, m), 7.84 (2H, d, J=8.7 Hz), 8.05 (1H, d, J=7.6 Hz), 8.38 (1H, s), 9.83 (1H, s)

Example 9

N-(4-cyanophenyl)-N'-(9-ethyl-9H-carbazol-3-yl)-N-(3-methoxypropyl)-3-methylpentanediamide (Step 1)

Using methyl 5-(4-cyanophenylamino)-3-methyl-5-oxopentanoate and 1-bromo-3-methoxypropane, and by the reaction and purification in the same manner as in the method described in Step 2 of Example 8, methyl 5-((4-cyanophenyl)(3-methoxypropyl)amino)-3-methyl-5-oxopentanoate was obtained.

MS (API): 333 (M+H)

(Step 2)

Using the compound obtained in Step 1, and by the reaction and purification in the same manner as in the method described in Step 3 of Example 8, 5-((4-cyanophenyl)(3-methoxypropyl)amino)-3-methyl-5-oxopentanoic acid was obtained as a crude product.

MS (API): 317 (M−H)

(Step 3)

Using the compound obtained in Step 2, and by the reaction and purification in the same manner as in the method described in Step 2 of Example 1, the title compound was obtained.

$^1$H-NMR (300 MHz, DMSO-$d_6$): δ0.90 (3H, d, J=6.8 Hz 1.30 (3H, t, J=7.0 Hz), 1.51-1.74 (2H, m), 1.92-2.08 (1H, m), 2.04-2.32 (3H, m), 2.36-2.48 (1H, m), 3.07-3.19 (3H, m), 3.29 (2H, t, J=6.2 Hz), 3.64-3.83 (2H, m), 4.41 (2H, q, J=7.1 Hz), 7.37-7.67 (3H, m), 7.85-8.00 (5H, m), 8.05 (1H, d, J=7.6 Hz), 8.36 (1H, s), 9.80 (1H, s)

Example 10

N-(4-cyanophenyl)-N'-(9-ethyl-9H-carbazol-3-yl)butanediamide

Using dihydrofuran-2,5-dione, and by the reaction and purification in the same manner as in the method described in Step 1 of Example 3 and Step 2 of Example 1, the title compound was obtained.

$^1$H-NMR (300 MHz, DMSO-$d_6$): δ1.30 (3H, t, J=7.0 Hz), 2.60-2.82 (4H, m), 4.41 (2H, q, J=6.8 Hz), 7.16 (1H, t, J=7.4 Hz), 7.43 (1H, t, J=7.4 Hz), 7.50-7.64 (3H, m), 7.69-7.89 (4H, m), 8.04 (1H, d, J=8.0 Hz), 8.42 (1H, s), 10.02 (1H, s), 10.48 (1H, s)

Example 11

N-(4-cyanophenyl)-N'-(9-ethyl-9H-carbazol-3-yl)cyclopropane-1,2-dicarboxamide Using 3-oxabicyclo(3.1.0)hexane-2,4-dione, and by the reaction and purification in the same manner as in the method described in Step 1 of Example 3 and Step 2 of Example 1, the title compound was obtained.

$^1$H-NMR (300 MHz, DMSO-$d_6$): δ1.20-1.39 (4H, m), 1.53-1.71 (1H, m), 2.17-2.41 (2H, m), 4.40 (2H, q, J=6.9 Hz), 7.15 (1H, t, J=7.4 Hz), 7.36-7.48 (1H, m), 7.48-7.63 (3H, m), 7.65-7.86 (4H, m), 7.99 (1H, d, J=8.0 Hz), 8.32 (1H, s), 0.10 (1H, s), 10.50 (1H, s)

Example 12

$N^4$-(4-cyanophenyl)-$N^1$-(9-ethyl-9H-carbazol-3-yl)-2-methylbutanediamide Using 3-methyldihydrofuran-2,5-dione, and by the reaction and purification in the same manner as in the method described in Step 1 of Example 3 and Step 2 of Example 1, the title compound was obtained.

$^1$H-NMR (300 MHz, DMSO-$d_6$): δ1.12-1.42 (6H, m), 2.53-2.57 (1H, m), 2.82 (1H, dt, J=15.7, 8.0 Hz), 2.98-3.16 (1H, m), 4.40 (2H, q, J=6.8 Hz), 7.16 (1H, t, J=7.4 Hz), 7.43 (1H, t, J=7.8 Hz), 7.48-7.64 (3H, m), 7.67-7.90 (4H, m), 8.03 (1H, d, J=7.6 Hz), 8.32-8.51 (1H, m), 10.00 (1H, d, J=3.0 Hz), 10.45 (1H, d, J=7.6 Hz)

Example 13

$N^4$-(4-cyanophenyl)-$N^1$-(9-ethyl-9H-carbazol-3-yl)-2,2-dimethylbutanediamide Using 3,3-dimethyldihydrofuran-2,5-dione, and by the reaction and purification in the same manner as in the method described in Step 1 of Example 3 and Step 2 of Example 1, the title compound was obtained.

$^1$H-NMR (300 MHz, DMSO-$d_6$): δ1.21-1.36 (3H, m), 1.39 (6H, s), 2.80 (2H, s), 4.42 (2H, q, J=6.9 Hz), 7.04-7.28 (1H, m), 7.37-7.68 (4H, m), 7.68-7.89 (4H, m), 8.04 (1H, d, J=7.6 Hz), 8.34 (1H, d, J=1.9 Hz), 9.36 (1H, s), 10.50 (1H, s)

Example 14

N-(3-chloro-4-cyanophenyl)-N'-(9-ethyl-9H-carbazol-3-yl)-3-methylpentanediamide (Step 1)

A solution of 4-amino-2-chlorobenzonitrile (500 mg, 3.28 mmol) and 4-methyldihydro-2H-pyran-2,6(3H)-dione (420 mg, 3.28 mmol) in THF (15 mL) was stirred at 90° C. for 14 hr. The reaction solution was concentrated to give 5-(3-chloro-4-cyanophenylamino)-3-methyl-5-oxopentanoic acid (1143 mg, 4.07 mmol, 124%) as a crude product.

$^1$H-NMR (300 MHz, DMSO-$d_6$): δ0.82-1.07 (3H, m), 2.05-2.42 (5H, m), 7.60 (1H, dd, J=8.7, 1.9 Hz), 7.88 (1H, d, J=8.7 Hz), 8.06 (1H, d, J=1.5 Hz), 10.50 (1H, s), 12.08 (1H, s)

(Step 2)

To a solution of the compound obtained in Step 1 (300 mg, 1.07 mmol), 3-amino-9-ethylcarbazole (270 mg, 1.28 mmol) and DIEA (0.560 mL, 3.21 mmol) in DMF (6 mL) was added HATU (610 mg, 1.60 mmol), and the mixture was stirred at room temperature for 14 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane) to give the title compound (225 mg, 0.476 mmol, 44.5%) as a white powder.

$^1$H-NMR (300 MHz, DMSO-$d_6$): δ1.03 (3H, d, J=6.0 Hz), 1.20-1.40 (4H, m), 2.19-2.48 (3H, m), 2.54 (1H, brs), 4.41 (2H, q, J=7.1 Hz), 7.07-7.27 (1H, m), 7.36-7.69 (5H, m), 7.87 (1H, d, J=8.7 Hz), 7.97-8.14 (2H, m), 8.39 (1H, s), 9.91 (1H, s), 10.54 (1H, s)

Example 15

$N^1$-(4-cyanophenyl)-$N^5$-(9-ethyl-9H-carbazol-3-yl)-$N^1$,$N^5$,3-trimethylpentanediamide (Step 1)

Using 5-(4-cyanophenylamino)-3-methyl-5-oxopentanoic acid, and by the reaction and purification in the same manner as in the method described in Step 2 of Example 1, $N^1$-(4-cyanophenyl)-$N^5$-(9-ethyl-9H-carbazol-3-yl)-3-methylpentanediamide was obtained.

MS (API): 439 (M+H)

$^1$H-NMR (300 MHz, DMSO-$d_6$): δ1.03 (3H, d, J=6.4 Hz) 1.30 (3H, t, J=7.0 Hz), 2.18-2.48 (4H, m), 2.54-2.59 (1H, m), 4.41 (2H, q, J=7.2 Hz), 7.17 (1H, t, J=7.2 Hz), 7.34-7.64 (4H, m), 7.67-7.88 (3H, m), 7.95 (1H, s), 8.03 (1H, d, J=7.6 Hz), 8.40 (1H, s), 9.92 (1H, s), 10.37 (1H, s)

(Step 2)

To a solution of the compound obtained in Step 1 (200 mg, 0.46 mmol) in DMF (6 mL) were added sodium hydride (60% in oil, 219 mg, 4.56 mmol) and methyl iodide (0.142 mL, 2.28 mmol), and the mixture was stirred at room temperature for 14 hr. The reaction solution was cooled to 0° C., water was added thereto, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give the title compound (30.7 mg, 0.066 mmol, 14.43%) as a pale-yellow powder.

MS (API): 467 (M+H)

Example 16

N-(4-cyanophenyl)-N'-(9-ethyl-9H-carbazol-3-yl)pentanediamide (Step 1)

A solution of dihydro-2H-pyran-2,6(3H)-dione (483 mg, 4.23 mmol) and 4-aminobenzonitrile (500 mg, 4.23 mmol) in THF (15 mL) was heated with reflux for 14 hr. The reaction solution was concentrated under reduced pressure, and the precipitate was washed with ethyl acetate to give 5-(4-cyanophenylamino)-5-oxopentanoic acid (782 mg, 3.37 mmol, 80%) as a pale-yellow powder.

$^1$H-NMR (300 MHz, DMSO-$d_6$): δ1.81 (2H, quin, J=7.4 Hz), 2.17-2.35 (2H, m), 2.41 (2H, t, J=7.4 Hz), 7.56-7.96 (4H, m), 10.33 (1H, s), 12.08 (1H, brs)

(Step 2)

To a solution of the compound obtained in Step 1 (200 mg, 0.97 mmol), 9-ethyl-9H-carbazol-3-amine (217 mg, 1.03 mmol) and DIEA (0.451 mL, 2.58 mmol) in DMF (6 mL) was added HATU (491 mg, 1.29 mmol), and the mixture was stirred at room temperature for 14 hr. The reaction mixture was poured into water, and extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane) to give the title compound (229 mg, 0.540 mmol, 62.7%) as a white powder.

$^1$H-NMR (300 MHz, DMSO-$d_6$): δ1.30 (3H, t, J=7.0 Hz), 1.85-2.11 (2H, m), 2.31-2.44 (1H, m), 2.49-2.63 (3H, m), 4.41 (2H, q, J=6.8 Hz), 7.17 (1H, t, J=7.4 Hz), 7.36-7.65 (4H, m), 7.69-7.90 (4H, m), 8.04 (1H, d, J=7.6 Hz), 8.43 (1H, s), 9.92 (1H, s), 10.37 (1H, s)

Example 17

N-(4-cyanophenyl)-N'-(9-ethyl-9H-carbazol-3-yl)hexanediamide (Step 1)

Using adipic anhydride, and by the reaction and purification in the same manner as in the method described in Step 1 of Example 3, 6-(4-cyanophenylamino)-6-oxohexanoic acid was obtained.

$^1$H-NMR (300 MHz, DMSO-$d_6$): δ1.42-1.70 (4H, m), 2.13-2.30 (2H, m), 2.36 (2H, t, J=7.0 Hz), 7.58-7.95 (4H, m), 10.32 (1H, d, J=3.0 Hz), 12.00 (1H, brs)

(Step 2)

Using the compound obtained in Step 1 and 9-ethyl-9H-carbazol-3-amine, and by the reaction and purification in the same manner as in the method described in Step 2 of Example 3, the title compound was obtained.

$^1$H-NMR (300 MHz, DMSO-$d_6$): δ1.30 (3H, t, J=7.0 Hz), 1.68 (4H, brs) 2.27-2.46 (4H, m), 4.41 (2H, q, J=7.1 Hz), 7.07-7.25 (1H, m), 7.36-7.63 (4H, m), 7.68-7.85 (4H, m), 8.04 (1H, d, J=7.6 Hz), 8.40 (1H, s), 9.89 (1H, s), 10.35 (1H, s)

Example 18

N-[4-cyano-3-(trifluoromethyl)phenyl]-N'-(9-ethyl-9H-carbazol-3-yl)-3-methylpentanediamide (Step 1)

A solution of 4-amino-2-(trifluoromethyl)benzonitrile (500 mg, 2.69 mmol) and 4-methyldihydro-2H-pyran-2,6 (3H)-dione (344 mg, 2.69 mmol) in THF (15 mL) was stirred at 90° C. for 14 hr. The reaction solution was concentrated to give 5-(4-cyano-3-(trifluoromethyl)phenylamino)-3-methyl-5-oxopentanoic acid (964 mg, 3.07 mmol, 114%) as a crude product.

$^1$H-NMR (300 MHz, DMSO-$d_6$): δ0.80-1.08 (3H, m), 2.08-2.47 (5H, m), 7.88-8.16 (2H, m), 8.28 (1H, d, J=1.9 Hz), 10.68 (1H, s), 12.09 (1H, s)

(Step 2)

To a solution of the compound obtained in Step 1 (300 mg, 0.95 mmol), 3-amino-9-ethylcarbazole (241 mg, 1.15 mmol) and DIEA (0.500 mL, 2.86 mmol) in DMF (6 mL) was added HATU (544 mg, 1.43 mmol), and the mixture was stirred at room temperature for 14 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane), and then NH-silica gel column chromatography (solvent gradient; 5 to 100% ethyl acetate/hexane) to give the title compound (189 mg, 0.372 mmol, 39.0%) as a white powder.

$^1$H-NMR (300 MHz, DMSO-$d_6$): δ1.05 (3H, d, J=6.0 Hz), 1.30 (3H, t, J=7.0 Hz), 2.24-2.48 (3H, m), 2.56 (2H, d, J=10.6 Hz), 4.41 (2H, q, J=6.8 Hz), 7.17 (1H, t, J=7.4 Hz), 7.33-7.67 (4H, m), 7.89-8.16 (3H, m), 8.30 (1H, s), 8.41 (1H, s), 9.93 (1H, s), 10.72 (1H, s)

Example 19

N-(4-cyanophenyl)-3-methyl-N'-(9-propyl-2,3,4,9-tetrahydro-1H-carbazol-6-yl)pentanediamide (Step 1)

To a solution of 6-nitro-2,3,4,9-tetrahydro-1H-carbazole (250 mg, 1.16 mmol) and potassium carbonate (479 mg, 3.47 mmol) in DMF (8 mL) was added 1-bromopropane (0.263 mL, 2.89 mmol), and the mixture was stirred at 70° C. for 14 hr. The reaction mixture was cooled, and to the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 55% ethyl acetate/hexane) to give 6-nitro-9-propyl-2,3,4,9-tetrahydro-1H-carbazole (279 mg, 1.081 mmol, 93%) as a yellow powder.

$^1$H-NMR (300 MHz, $CDCl_3$): δ0.95 (3H, t, J=7.4 Hz), 1.66-2.05 (6H, m), 2.60-2.85 (4H, m), 3.89-4.11 (2H, m), 7.15-7.33 (1H, m), 8.03 (1H, dd, J=8.7, 2.3 Hz), 8.41 (1H, d, J=2.3 Hz)

(Step 2)

A solution of the compound obtained in Step 1 (270 mg, 1.05 mmol) and 10% palladium on carbon (50% wet, 10 mg, 0.09 mmol) in a mixed solvent of methanol (4 mL) and ethyl acetate (4 mL) was stirred at room temperature for 14 hr under 1 atm of hydrogen atmosphere. The catalyst was removed by filtration, and the filtrate was concentrated under reduced pressure to give 9-propyl-2,3,4,9-tetrahydro-1H-carbazol-6-amine (230 mg, 1.006 mmol, 96%) as a brown oil.

MS (API): 229 (M+H)

(Step 3)

To a solution of the compound obtained in Step 2 (229 mg, 1.00 mmol), 5-(4-cyanophenylamino)-3-methyl-5-oxopentanoic acid (247 mg, 1.00 mmol) and DIEA (0.525 mL, 3.01 mmol) in DMF (6 mL) was added HATU (572 mg, 1.50 mmol), and the mixture was stirred at room temperature for 14 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane) to give the title compound (151 mg, 0.332 mmol, 33.1%) as a white powder.

$^1$H-NMR (300 MHz, DMSO-$d_6$): δ0.84 (3H, t, J=7.4 Hz), 1.00 (3H, d, J=6.4 Hz), 1.51-1.71 (2H, m), 1.71-1.94 (4H, m), 2.19-2.39 (3H, m), 2.41-2.48 (2H, m), 2.57 (2H, t, J=5.5 Hz), 2.68 (2H, t, J=5.7 Hz), 3.96 (2H, t, J=7.2 Hz), 7.15 (1H, dd, J=8.7, 1.9 Hz), 7.25 (1H, d, J=8.3 Hz), 7.67 (1H, d, J=1.9 Hz), 7.70-7.87 (4H, m), 9.66 (1H, s), 10.35 (1H, s)

Example 20

N-(4-cyanophenyl)-3-methyl-N'-[9-(2-methylpropyl)-2,3,4,9-tetrahydro-1H-carbazol-6-yl]pentanediamide (Step 1)

To a solution of 6-nitro-2,3,4,9-tetrahydro-1H-carbazole (250 mg, 1.16 mmol) and potassium carbonate (479 mg, 3.47 mmol) in DMF (8 mL) was added 1-bromo-2-methylpropane (0.314 mL, 2.89 mmol), and the mixture was stirred at 70° C. for 14 hr. The reaction mixture was cooled, and to the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 55% ethyl acetate/hexane) to give 9-isobutyl-6-nitro-2,3,4,9-tetrahydro-1H-carbazole (296 mg, 1.087 mmol, 94%) as a yellow powder.

$^1$H-NMR (300 MHz, $CDCl_3$): δ0.93 (6H, d, J=6.8 Hz), 1.77-2.05 (4H, m), 2.05-2.28 (1H, m), 2.62-2.84 (4H, m), 3.83 (2H, d, J=7.6 Hz), 7.14-7.32 (1H, m), 8.03 (1H, dd, J=9.1, 2.3 Hz), 8.41 (1H, d, J=2.3 Hz)

(Step 2)

A solution of the compound obtained in Step 1 (290 mg, 1.06 mmol) and 10% palladium on carbon (50% wet, 10 mg, 0.09 mmol) in a mixed solvent of methanol (4 mL) and ethyl acetate (4 mL) was stirred at room temperature for 14 hr under 1 atm of hydrogen atmosphere. The catalyst was removed by filtration, and the filtrate was concentrated under reduced pressure to give 9-isobutyl-2,3,4,9-tetrahydro-1H-carbazol-6-amine (237 mg, 0.977 mmol, 92%) as a brown oil.

MS (API): 243 (M+H)

(Step 3)

To a solution of the compound obtained in Step 2 (235 mg, 0.97 mmol), 5-(4-cyanophenylamino)-3-methyl-5-oxopentanoic acid (239 mg, 0.97 mmol) and DIEA (0.508 mL, 2.91 mmol) in DMF (6 mL) was added HATU (553 mg, 1.45 mmol), and the mixture was stirred at room temperature for 14 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane) to give the title compound (242 mg, 0.515 mmol, 53.1%) as a white powder.

$^1$H-NMR (300 MHz, DMSO-$d_6$): δ0.84 (6H, d, J=6.4 Hz), 1.00 (3H, d, J=6.4 Hz), 1.81 (4H, dt, J=13.3, 6.6 Hz), 1.94-2.16 (1H, m), 2.16-2.41 (3H, m), 2.41-2.48 (2H, m), 2.53-2.75 (4H, m), 3.79 (2H, d, J=7.6 Hz), 7.14 (1H, dd, J=8.7, 1.9 Hz), 7.24 (1H, d, J=8.7 Hz), 7.67 (1H, d, J=1.9 Hz), 7.70-7.86 (4H, m), 9.66 (1H, s), 10.35 (1H, s)

Example 21

$N^1$-(4-cyanobenzyl)-$N^4$-(9-ethyl-9H-carbazol-3-yl)-2-methylbutanediamide Using 3-methyldihydrofuran-2,5-dione, and by the reaction and purification in the same manner as in the method described in Step 1 of Example 3 and Step 2 of Example 1, the title compound was obtained.

$^1$H-NMR (300 MHz, DMSO-$d_6$): δ1.08-1.43 (6H, m), 2.23-2.48 (1H, m), 2.58-2.78 (1H, m), 2.78-3.00 (1H, m), 4.41 (2H, q, J=6.9 Hz), 7.17 (1H, t, J=7.6 Hz), 7.35-7.65 (4H, m), 8.05 (1H, d, J=7.9 Hz), 8.33-8.52 (1H, m), 9.95 (1H, s), 12.14 (1H, brs)

Example 22

4-cyano-N-{4-[(9-ethyl-9H-carbazol-3-yl)amino]-4-oxobutyl}benzamide (Step 1)

To a solution of 3-amino-9-ethylcarbazole (500 mg, 2.38 mmol), 4-(tert-butoxycarbonylamino)butyric acid (483 mg, 2.38 mmol) and DIEA (1.246 mL, 7.13 mmol) in DMF (12 mL) was added HATU (1085 mg, 2.85 mmol), and the mixture was stirred at room temperature for 3 days. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 75% ethyl acetate/hexane) to give crude tert-butyl 4-(9-ethyl-9H-carbazol-3-ylamino)-4-oxobutylcarbamate (1080 mg, 2.73 mmol, 115%) as a pale-yellow powder.

$^1$H-NMR (300 MHz, $CDCl_3$): δ1.29-1.59 (12H, m), 1.92 (2H, quin, J=6.6 Hz), 2.43 (2H, t, J=7.0 Hz), 3.26 (2H, q, J=6.0 Hz), 4.29 (2H, q, J=7.2 Hz), 7.09-7.23 (1H, m), 7.23-7.50 (3H, m), 7.55 (1H, d, J=7.9 Hz), 7.94-8.08 (2H, m), 8.37 (1H, s), 8.77 (1H, brs)

(Step 2)

A solution of the compound obtained in Step 1 (1.0 g, 2.53 mmol) and 4M hydrogen chloride/ethyl acetate (4 mL, 16.00 mmol) in ethyl acetate (10 mL) was stirred at room temperature for 14 hr. The precipitate was collected by filtration, and washed with ethyl acetate to give 4-amino-N-(9-ethyl-9H-carbazol-3-yl)butanamide hydrochloride (0.622 g, 1.875 mmol, 74.2%) as a white powder.

MS (API): 296 (M−HCl+H)

(Step 3)

To a solution of the compound obtained in Step 2 (150 mg, 0.45 mmol), 4-cyanobenzoic acid (80 mg, 0.54 mmol) and DIEA (0.395 mL, 2.26 mmol) in DMF (6 mL) was added HATU (258 mg, 0.68 mmol), and the mixture was stirred at room temperature for 14 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give the title compound (141 mg, 0.332 mmol, 73.5%) as a white powder.

$^1$H-NMR (300 MHz, DMSO-$d_6$): δ1.30 (3H, t, J=7.0 Hz), 1.78-2.00 (2H, m), 2.42 (2H, t, J=7.4 Hz), 3.34-3.47 (2H, m), 4.41 (2H, q, J=6.9 Hz), 7.17 (1H, t, J=7.2 Hz), 7.37-7.48 (1H, m), 7.48-7.65 (3H, m), 7.87-8.11 (5H, m), 8.39 (1H, s), 8.78 (1H, t, J=5.5 Hz), 9.92 (1H, s)

Example 23

N-(3-{[(4-cyanophenyl)sulfonyl]amino}-2-methylpropyl)-9-ethyl-9H-carbazole-3-carboxamide (Step 1)

To a solution of tert-butyl (3-amino-2-methylpropyl)carbamate (200 mg, 1.06 mmol) and TEA (0.444 mL, 3.19 mmol) in THF (5 mL) was added 4-cyanobenzene-1-sulfonyl chloride (214 mg, 1.06 mmol), and the mixture was stirred at room temperature for 16 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give tert-butyl (3-(4-cyanophenylsulfonamido)-2-methylpropyl)carbamate (273 mg, 0.772 mmol, 72.7%) as a white powder.

$^1$H-NMR (300 MHz, DMSO-$d_6$): δ0.77 (3H, d, J=6.8 Hz), 1.34 (9H, s), 1.53-1.71 (1H, m), 2.52-2.57 (1H, m), 2.64-2.89 (3H, m), 6.78 (1H, t, J=5.8 Hz), 7.84 (1H, s), 7.90-7.97 (2H, m), 8.05-8.12 (2H, m)

(Step 2)

A solution of the compound obtained in Step 1 (273 mg, 0.77 mmol) in TFA (1 mL, 12.98 mmol) was stirred at room temperature for min, and the mixture was concentrated under reduced pressure. To the residue were added ethyl acetate and 1N aqueous sodium hydroxide solution, and the organic layer was separated. The organic layer was washed with water and saturated brine, and dried, and the solvent was evaporated under reduced pressure to give N-(3-amino-2-methylpropyl)-4-cyanobenzenesulfonamide (128 mg, 0.505 mmol, 65.4%) as a white powder.

$^1$H-NMR (300 MHz, DMSO-$d_6$): δ0.77 (3H, d, J=6.4 Hz), 1.41-1.55 (1H, m), 2.32-2.45 (2H, m), 2.61 (1H, dd, J=12.5, 6.8 Hz), 2.74-2.84 (1H, m), 3.59 (3H, brs), 7.91-7.98 (2H, m), 8.05-8.12 (2H, m)

(Step 3)

A solution of the compound obtained in Step 2 (65.7 mg, 0.26 mmol), 9-ethyl-9H-carbazole-3-carboxylic acid (62.1 mg, 0.26 mmol), HATU (128 mg, 0.34 mmol) and TEA (0.108 mL, 0.78 mmol) in DMF (1.25 mL) was stirred at room temperature for 16 hr. To the reaction solution was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 50% ethyl acetate/hexane) to give the title compound (81 mg, 0.170 mmol, 65.7%) as a white powder.

$^1$H-NMR (300 MHz, DMSO-$d_6$): δ0.89 (3H, d, J=6.4 Hz), 1.33 (3H, t, J=7.2 Hz), 1.81-1.98 (1H, m), 2.60-2.74 (1H, m), 2.79-2.91 (1H, m), 3.10-3.26 (2H, m), 4.48 (2H, q, J=6.9 Hz), 7.27 (1H, t, J=7.2 Hz), 7.45-7.55 (1H, m), 7.66 (2H, d, J=8.7 Hz), 7.86-8.07 (6H, m), 8.18 (1H, d, J=7.6 Hz), 8.40 (1H, t, J=5.7 Hz), 8.65 (1H, d, J=1.5 Hz)

Example 24

2-({2-[(4-cyanophenyl)amino]-2-oxoethyl}sulfanyl)-N-(9-ethyl-9H-carbazol-3-yl)acetamide (Step 1)

A solution of 4-aminobenzonitrile (500 mg, 4.23 mmol), 2,2'-thiodiacetic acid (3.18 g, 21.2 mmol), WSC (4.87 g, 25.4 mmol), DMAP (258 mg, 0.21 mmol) and DIEA (5.47 g, 42.3 mmol) in THF (200 mL) was stirred at room temperature for 60 hr. To the reaction solution was added water, and the mixture was extracted with ethyl acetate. The organic layer was washed with dilute hydrochloric acid, and dried, and the solvent was evaporated under reduced pressure. The obtained residue was purified by preparative HPLC to give 2-((2-((4-cyanophenyl)amino)-2-oxoethyl)thio)acetic acid (162 mg, 15.3%) as a pale-yellow powder.

$^1$H-NMR (300 MHz, DMSO-$d_6$): δ3.42 (2H, s), 3.47 (2H, s), 7.75 (2H, d, J=9.0 Hz), 7.78 (2H, d, J=9.0 Hz), 10.53 (1H, s), 12.64 (1H, s)

(Step 2)

A solution of the compound obtained in Step 1 (145 mg, 0.58 mmol), 9-ethyl-9H-carbazol-3-amine (122 mg, 0.58 mmol), HATU (330 mg, 0.87 mmol) and DIEA (225 mg, 1.74 mmol) in DMF (4 mL) was stirred at room temperature for 16 hr. To the reaction solution was added dilute hydrochloric acid, and the mixture was extracted with ethyl acetate. The organic layer was washed with dilute hydrochloric acid, and dried, and the solvent was evaporated under reduced pressure. The obtained residue was purified by silica gel column chromatography to give the title compound (150 mg, 0.339 mmol, 59%) as a white powder.

$^1$H-NMR (300 MHz, DMSO-$d_6$): δ1.30 (3H, t, J=7.2 Hz), 3.53 (2H, s), 3.60 (2H, s), 4.41 (2H, q, J=7.2 Hz), 7.15-7.20 (1H, m), 7.42-7.47 (1H, m), 7.53-7.60 (3H, m), 7.73-7.80 (4H, m), 8.01 (1H, d, J=7.5 Hz), 8.37 (1H, t like), 10.13 (1H, s), 10.59 (1H, s)

Example 25

N-(3-chloro-4-cyanophenyl)-N'-(9-ethyl-9H-carbazol-3-yl)-3-methylpentanediamide (Optically Active Form Having a Shorter Retention Time)

Example 26

N-(3-chloro-4-cyanophenyl)-N'-(9-ethyl-9H-carbazol-3-yl)-3-methylpentanediamide (Optically Active Form Having a Longer Retention Time)

N-(3-Chloro-4-cyanophenyl)-N'-(9-ethyl-9H-carbazol-3-yl)-3-methylpentanediamide (0.500 g) was subjected to optical resolution by chiral column chromatography. The preparative fraction having a shorter retention time was concentrated to give the title compound (0.195 g) of Example 25, and the preparative fraction having a longer retention time was concentrated to give the title compound (0.203 g) of Example 26, each as a white powder.

purification condition by chiral column chromatography
- column: CHIRALPAK AD 50 mm ID×500 mL
- solvent: hexane/ethanol=500/500 (v/v)
- flow rate: 80 mL/min
- temperature: 40° C.
- detection: UV 220 nm The Title Compound of Example 25
- optical purity: >99.9% ee, chemical purity: >99.9%
- MS (API): 473 (M+H)

The Title Compound of Example 26
- optical purity: >99.9% ee, chemical purity: >99.9%
- MS (API): 473 (M+H)

Example 27

5-(3-chloro-4-cyanophenoxy)-N-(9-ethyl-9H-carbazol-3-yl)pentanamide (Step 1)

To a solution of 9-ethyl-9H-carbazol-3-amine (300 mg, 1.43 mmol) in toluene (4 mL) was added trimethylaluminium (1.8M in toluene solution, 1.189 mL, 2.14 mmol), and the mixture was stirred at room temperature for 30 min. To the reaction mixture was added a solution of δ-valerolactone (0.129 mL, 1.43 mmol) in toluene (4 mL) at room temperature, and the mixture was stirred at 80° C. for 4 hr. The reaction mixture was cooled to 0° C., neutralized with 1N hydrochloric acid, and extracted with ethyl acetate. The organic layer was washed with water and saturated brine, and dried, and the solvent was evaporated under reduced pressure to give N-(9-ethyl-9H-carbazol-3-yl)-5-hydroxypentanamide (420 mg, 1.352 mmol, 95%) as a pale-yellow powder.

MS (API): 311 (M+H)

(Step 2)

To a solution of the compound obtained in Step 1 (150 mg, 0.48 mmol) and 2-chloro-4-fluorobenzonitrile (75 mg, 0.48 mmol) in THF (6 mL) was added potassium t-butoxide (136 mg, 1.21 mmol), and the mixture was stirred at room temperature for 3 days. Water was poured into the reaction mixture, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 85% ethyl acetate/hexane) to give the title compound (79 mg, 0.178 mmol, 36.8%) as a white powder.

$^1$H-NMR (300 MHz, $CDCl_3$): δ1.42 (3H, t, J=7.2 Hz), 1.86-2.06 (4H, m), 2.42-2.59 (2H, m), 4.07 (2H, s), 4.35 (2H, q, J=7.1 Hz), 6.85 (1H, dd, J=8.7, 2.3 Hz), 7.01 (1H, d, J=2.6 Hz), 7.14-7.26 (2H, m), 7.29-7.61 (5H, m), 8.06 (1H, d, J=7.6 Hz), 8.30 (1H, d, J=1.9 Hz)

Example 28

4-cyano-N-ethyl-N-{4-[(9-ethyl-9H-carbazol-3-yl)amino]-4-oxobutyl}benzamide (Step 1)

To a solution of 4-cyanobenzoic acid (2.0 g, 13.59 mmol), ethyl 4-aminobutyrate hydrochloride (2.507 g, 14.95 mmol), HOBt (0.918 g, 6.80 mmol) and TEA (6.63 mL, 47.58 mmol) in DMF (20 mL) was added WSC (3.26 g, 16.99 mmol), and the mixture was stirred at room temperature for 14 hr. Water was poured into the reaction mixture, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane) to give ethyl 4-(4-cyanobenzamido)butanoate (1.558 g, 5.99 mmol, 44.0%) as a white powder.

$^1$H-NMR (300 MHz, $CDCl_3$): δ1.25 (3H, t, J=7.0 Hz), 1.98 (2H, quin, J=6.6 Hz), 2.48 (2H, t, J=6.6 Hz), 3.42-3.62 (2H, m), 4.14 (2H, q, J=7.2 Hz), 6.96 (1H, brs), 7.68-7.81 (2H, m), 7.85-7.97 (2H, m)

(Step 2)

To a solution of the compound obtained in Step 1 (200 mg, 0.77 mmol) in DMF (4 mL) were added sodium hydride (50% oil, 111 mg, 2.31 mmol) and ethyl iodide (0.093 mL, 1.15 mmol) at room temperature, and the mixture was stirred at 60° C. for 14 hr. To the reaction solution was added 1N aqueous sodium hydroxide solution (3 mL, 3.00 mmol), and the mixture was stirred at 60° C. for additional 2 hr. The reaction solution was cooled, and neutralized with 1N hydrochloric acid. The reaction mixture was extracted with ethyl acetate. The organic layer was washed with water and saturated brine, and dried, and the solvent was evaporated under reduced pressure to give 4-(4-cyano-N-ethylbenzamido)butanoic acid (0.23 g, 0.76 mmol, 98.7%) as a crude product.

(Step 3)

To a solution of the compound obtained in Step 1 (0.23 g, 0.76 mmol), 3-amino-N-ethylcarbazole (159 mg, 0.76 mmol) and DIEA (0.396 mL, 2.27 mmol) in DMF (6 mL) was added HATU (359 mg, 0.94 mmol), and the mixture was stirred at room temperature for 14 hr. Water was poured into the reaction mixture, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give the title compound (43.4 mg, 0.087 mmol, 11.56%) as a white powder.

$^1$H-NMR (300 MHz, $CDCl_3$): δ1.40 (3H, t, J=7.0 Hz), 1.66-1.86 (2H, m), 1.97 (1H, brs), 2.08-2.20 (1H, m), 2.24 (1H, brs), 2.52 (1H, t, J=6.2 Hz), 3.04-3.27 (4H, m), 3.27-3.42 (2H, m), 3.49 (1H, brs), 3.56-3.82 (2H, m), 4.33 (2H, q, J=7.2 Hz), 7.16-7.56 (7H, m), 7.61 (2H, d, J=7.9 Hz), 8.03 (1H, d, J=7.9 Hz), 8.37 (1H, s), 8.49 (1H, brs)

Example 29

4-cyano-N-{4-[(9-ethyl-9H-carbazol-3-yl)amino]-4-oxobutyl}-N-(3-methoxypropyl)benzamide (Step 1)

Using ethyl 4-(4-cyanobenzamido)butanoate and 1-bromo-3-methoxypropane, and by the reaction and purification in the same manner as in the method described in Step 2 of Example 28, 4-(4-cyano-N-(3-methoxypropyl)benzamido)butanoic acid was obtained.

MS (API): 303 (M−H)

(Step 2)

Using the compound obtained in Step 1, and by the reaction and purification in the same manner as in the method described in Step 3 of Example 28, the title compound was obtained.

$^1$H-NMR (300 MHz, $CDCl_3$): δ1.40 (3H, t, J=7.0 Hz), 1.66-1.86 (2H, m), 1.97 (1H, brs), 2.08-2.20 (1H, m), 2.24 (1H, brs), 2.52 (1H, t, J=6.2 Hz), 3.04-3.27 (4H, m), 3.27-3.42 (2H, m), 3.49 (1H, brs), 3.56-3.82 (2H, m), 4.33 (2H, q, J=7.2 Hz), 7.16-7.56 (7H, m), 7.61 (2H, d, J=7.9 Hz), 8.03 (1H, d, J=7.9 Hz), 8.37 (1H, s), 8.49 (1H, brs)

Example 30

5-(3-chloro-4-cyanophenoxy)-N-(9-ethyl-9H-carbazol-3-yl)-3-hydroxy-3-methylpentanamide (Step 1)

To a solution of 9-ethyl-9H-carbazol-3-amine (300 mg, 1.43 mmol) in toluene (4 mL) was added trimethylaluminium (1.8M in toluene solution, 1.189 mL, 2.14 mmol), and the mixture was stirred at room temperature for 30 min. To the reaction mixture was added a solution of 4-hydroxy-4-methyltetrahydro-2H-pyran-2-one (186 mg, 1.43 mmol) in toluene (4 mL) at room temperature, and the mixture was stirred at 80° C. for 4 hr. The reaction mixture was cooled to 0° C., neutralized with 1N hydrochloric acid, and extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give N-(9-ethyl-9H-carbazol-3-yl)-3,5-dihydroxy-3-methylpentanamide (359 mg, 1.056 mmol, 74.0%) as a colorless oil.

$^1$H-NMR (300 MHz, $CDCl_3$): δ1.33-1.53 (6H, m), 1.71-2.01 (2H, m), 2.49 (1H, d, J=14.7 Hz), 2.73 (1H, d, J=14.3 Hz), 2.83-3.03 (1H, m), 3.81-4.06 (2H, m), 4.33 (2H, q, J=7.2 Hz), 4.90 (1H, s), 7.16-7.55 (5H, m), 7.97-8.12 (1H, m), 8.27 (1H, d, J=1.9 Hz), 8.36 (1H, s)

(Step 2)

To a solution of the compound obtained in Step 1 (348 mg, 1.02 mmol) and 2-chloro-4-fluorobenzonitrile (159 mg, 1.02 mmol) in THF (10 mL) was added potassium t-butoxide (287 mg, 2.56 mmol), and the mixture was stirred at room temperature for 14 hr. Water was poured into the reaction mixture, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give the title compound (236 mg, 0.496 mmol, 48.5%) as a white powder.

$^1$H-NMR (300 MHz, $CDCl_3$): δ1.30-1.54 (6H, m), 1.85-2.24 (2H, m), 2.45-2.78 (2H, m), 4.03-4.43 (4H, m), 4.64 (1H, s), 6.83 (1H, dd, J=8.9, 2.5 Hz), 7.00 (1H, d, J=2.3 Hz), 7.17-7.55 (6H, m), 7.77-7.95 (1H, m), 7.96-8.10 (1H, m), 8.24 (1H, d, J=1.9 Hz)

Example 31

2-({2-[(4-cyanophenyl)amino]-2-oxoethyl}sulfonyl)-N-(9-ethyl-9H-carbazol-3-yl)acetamide To a solution of 2-({2-[(4-cyanophenyl)amino]-2-oxoethyl}sulfanyl)-N-(9-ethyl-9H-carbazol-3-yl)acetamide (60 mg, 0.14 mmol) in DMF (1.5 mL) was added mCPBA (73.5 mg, 0.30 mmol), and the mixture was stirred at room temperature for 3 hr. Aqueous sodium thiosulfate solution was poured into the reaction mixture, and the mixture was extracted with ethyl acetate. The organic layer was washed with aqueous sodium carbonate solution, and dried, and the solvent was evaporated under reduced pressure. The obtained residue was purified by silica gel column chromatography to give the title compound (42 mg, 0.088 mmol, 65%) as a pale-yellow powder.

$^1$H-NMR (300 MHz, $CDCl_3$): δ1.31 (3H, t, J=7.2 Hz), 4.43 (2H, q, J=7.2 Hz), 4.51 (2H, s), 4.60 (2H, s), 7.17-7.22 (1H, m), 7.43-7.49 (1H, m), 7.53-7.62 (3H, m), 7.77-7.85 (4H, m), 8.09 (1H, d, J=7.8 Hz), 8.44 (1H, d, J=1.8 Hz), 10.52 (1H, s), 10.92 (1H, s)

Example 32

N-(3-{[(4-cyanophenyl)carbonyl]amino}-2-methylpropyl)-9-ethyl-9H-carbazole-3-carboxamide (Step 1)

A solution of tert-butyl (3-amino-2-methylpropyl)carbamate (200 mg, 1.06 mmol), 4-cyanobenzoic acid (156 mg, 1.06 mmol), HATU (525 mg, 1.38 mmol) and TEA (0.444 mL, 3.19 mmol) in DMF (5 mL) was stirred at room temperature for 16 hr. Water was poured into the reaction mixture, and the mixture was extracted with ethyl acetate. The organic layer was dried, and the solvent was evaporated under reduced pressure. The obtained residue was purified by silica gel column chromatography (solvent gradient; 10 to 50% ethyl acetate/hexane) to give tert-butyl (3-(4-cyanobenzamido)-2-methylpropyl)carbamate (311 mg, 0.980 mmol, 92%) as a white powder.

$^1$H-NMR (300 MHz, $CDCl_3$): δ0.83 (3H, d, J=6.8 Hz), 1.37 (9H, s), 1.74-1.93 (1H, m), 2.76-3.00 (2H, m), 3.05-3.25 (2H, m), 6.82 (1H, t, J=5.7 Hz), 7.93-8.02 (4H, m), 8.65 (1H, t, J=5.5 Hz)

(Step 2)

A solution of the compound obtained in Step 1 (311 mg, 0.98 mmol) in TFA (1 mL, 12.98 mmol) was stirred at room temperature for 15 min, and concentrated under reduced pressure. To the residue were added ethyl acetate and 1N aqueous sodium hydroxide solution, and the organic layer was separated. The organic layer was washed with water and saturated brine, and dried, and the solvent was evaporated under reduced pressure to give N-(3-amino-2-methylpropyl)-4-cyanobenzamide (198 mg, 0.911 mmol, 93%) as a white powder.

(Step 3)

A solution of the compound obtained in Step 2 (198 mg, 0.91 mmol), 9-ethyl-9H-carbazole-3-carboxylic acid (218 mg, 0.91 mmol), HATU (450 mg, 1.18 mmol) and TEA (0.381 mL, 2.73 mmol) in DMF (4.5 mL) was stirred at room temperature for 16 hr. Water was poured into the reaction mixture, and the mixture was extracted with ethyl acetate. The organic layer was dried, and the solvent was evaporated under reduced pressure. The obtained residue was purified by silica gel column chromatography (solvent gradient; 20 to 100% ethyl acetate/hexane) to give the title compound (200 mg, 0.456 mmol, 50.0%) as a white powder.

$^1$H-NMR (300 MHz, DMSO-$d_6$): δ0.95 (3H, d, J=6.8 Hz 1.33 (3H, t, J=7.2 Hz), 2.02-2.16 (1H, m), 3.19-3.37 (3H, m), 4.48 (2H, q, J=6.9 Hz), 7.26 (1H, t, J=7.2 Hz), 7.46-7.55 (1H, m), 7.66 (2H, d, J=8.7 Hz), 7.92-8.06 (5H, m), 8.18 (1H, d, J=7.5 Hz), 8.50 (1H, t, J=5.8 Hz), 8.70 (1H, d, J=1.5 Hz), 8.79 (1H, t, J=5.8 Hz)

Example 33

N-{3-[(4-cyanobenzyl)amino]-2-methyl-3-oxopropyl}-9-ethyl-9H-carbazole-3-carboxamide (Step 1)

A solution of 3-((tert-butoxycarbonyl)amino)-2-methylpropanoic acid (200 mg, 0.98 mmol), 4-(aminomethyl)benzonitrile (130 mg, 0.98 mmol), HATU (486 mg, 1.28 mmol) and TEA (0.411 mL, 2.95 mmol) in DMF (5 mL) was stirred at room temperature for 16 hr. Water was poured into the reaction mixture, and the mixture was extracted with ethyl acetate. The organic layer was dried, and the solvent was evaporated under reduced pressure. The obtained residue was purified by silica gel column chromatography (solvent gradient; 20 to 67% ethyl acetate/hexane) to give tert-butyl (3-((4-cyanobenzyl)amino)-2-methyl-3-oxopropyl)carbamate (221 mg, 0.696 mmol, 70.8%) as a white powder.

$^1$H-NMR (300 MHz, DMSO-$d_6$): δ1.00 (3H, d, J=7.2 Hz), 1.37 (9H, s), 2.90 (1H, dt, J=13.2, 6.6 Hz), 3.03-3.16 (1H, m), 4.23-4.42 (2H, m), 6.77 (1H, t, J=5.5 Hz), 7.42 (2H, d, J=8.3 Hz), 7.72-7.82 (2H, m), 8.44 (1H, t, J=6.0 Hz)

(Step 2)

A solution of the compound obtained in Step 1 (221 mg, 0.70 mmol) in TFA (1 mL, 12.98 mmol) was stirred at room temperature for 15 min, and concentrated under reduced pressure. To the residue were added ethyl acetate and 1N aqueous sodium hydroxide solution, and the organic layer was separated. The organic layer was washed with water and saturated brine, and dried, and the solvent was evaporated under reduced pressure to give 3-amino-N-(4-cyanobenzyl)-2-methylpropanamide (112 mg, 0.515 mmol, 74.0%) as a white powder.

(Step 3)

A solution (2.5 mL) of the compound obtained in Step 2 (112 mg, 0.52 mmol), 9-ethyl-9H-carbazole-3-carboxylic acid (123 mg, 0.52 mmol), HATU (255 mg, 0.67 mmol) and TEA (0.216 mL, 1.55 mmol) in DMF was stirred at room temperature for 16 hr. Water was poured into the reaction mixture, and the mixture was extracted with ethyl acetate. The organic layer was dried, and the solvent was evaporated under reduced pressure. The obtained residue was purified by silica gel column chromatography (solvent; ethyl acetate) to give the title compound (158 mg, 0.360 mmol, 69.9%) as a white powder.

$^1$H-NMR (300 MHz, DMSO-$d_6$): δ1.11 (3H, d, J=6.8 Hz), 1.34 (3H, t, J=7.2 Hz), 2.75-2.89 (1H, m), 3.33-3.49 (2H, m), 4.19-4.32 (1H, m), 4.39-4.56 (3H, m), 7.26 (1H, t, J=7.3 Hz), 7.38 (2H, d, J=8.7 Hz), 7.46-7.60 (3H, m), 7.66 (2H, d, J=8.3

Hz), 7.99 (1H, dd, J=8.7, 1.5 Hz), 8.15 (1H, d, J=7.9 Hz), 8.51 (2H, q, J=5.8 Hz), 8.71 (1H, d, J=1.5 Hz)

Example 34

2-((2-((4-cyanophenyl)amino)-2-oxoethyl)sulfinyl)-N-(9-ethyl-9H-carbazol-3-yl)acetamide To a solution of 2-({2-[(4-cyanophenyl)amino]-2-oxoethyl}sulfanyl)-N-(9-ethyl-9H-carbazol-3-yl)acetamide (55 mg, 0.12 mmol) in a mixed solvent of acetonitrile (4 mL) and water (2 mL) was added sodium periodate (29.2 mg, 0.14 mmol), and the mixture was stirred at room temperature for 18 days. Aqueous sodium thiosulfate solution was poured into the reaction mixture, and the mixture was extracted with ethyl acetate. The organic layer was washed with aqueous sodium carbonate solution, and dried, and the solvent was evaporated under reduced pressure. The obtained residue was purified by preparative HPLC to give the title compound (13 mg, 0.028 mmol, 23%) as a pale-yellow powder.

$^1$H-NMR (300 MHz, DMSO-$d_6$): δ1.31 (3H, t, J=6.9 Hz), 4.01 (2H, t, J=13.8 Hz), 4.19 (2H, t, J=13.8 Hz), 4.43 (2H, q, J=6.9 Hz), 7.19 (1H, t, J=7.8 Hz), 7.46 (1H, t, J=7.5 Hz), 7.55-7.61 (3H, m), 7.81 (4H, s), 8.07 (1H, d, J=7.5 Hz), 8.45 (1H, s), 10.43 (1H, s), 10.85 (1H, s)

Example 35

2-((2-((4-cyanophenyl)amino)-2-oxoethyl)(methyl)amino)-N-(9-ethyl-9H-carbazol-3-yl)acetamide (Step 1)

A mixture of 2,2'-(methylazanediyl)diacetic acid (500 mg, 3.40 mmol) and acetic anhydride (5 mL) was stirred at 165° C. for 30 min. The reaction mixture was concentrated under reduced pressure to give 4-methylmorpholine-2,6-dione as a crude product. The obtained crude product was dissolved in THF (10 mL), and p-aminobenzonitrile (401 mg, 3.40 mmol) was added thereto. The mixture was heated with reflux for 22 hr, and concentrated under reduced pressure to give 2-((2-((4-cyanophenyl)amino)-2-oxoethyl)(methyl)amino)acetic acid (467 mg, 56%) as a pale-brown powder.

$^1$H-NMR (300 MHz, DMSO-$d_6$): δ2.42 (3H, s), 3.41 (4H, s), 7.76-7.85 (4H, m), 10.30 (1H, s)

(Step 2)

Using the compound obtained in Step 1 and 9-ethyl-9H-carbazol-3-amine, and by the reaction and purification in the same manner as in the method described in Step 2 of Example 3, the title compound was obtained.

$^1$H-NMR (300 MHz, DMSO-$d_6$): δ1.31 (3H, t, J=7.2 Hz), 2.49 (3H, s), 3.43 (2H, s), 3.48 (2H, s), 4.42 (2H, q, J=7.2 Hz), 7.19 (1H, t, J=7.5 Hz), 7.42-7.48 (1H, m), 7.56-7.67 (3H, m), 7.81 (2H, d, J=8.7 Hz), 7.91 (2H, d, J=8.7 Hz), 8.07 (1H, d, J=7.8 Hz), 8.44 (1H, d, J=2.1 Hz), 10.07 (1H, s), 10.55 (1H, s)

Example 36

$N^2$-[(4-cyanophenyl)acetyl]-N-[(9-ethyl-9H-carbazol-3-yl)methyl]alanine amide (Step 1)

A solution of 2-((tert-butoxycarbonyl)amino)propanoic acid (200 mg, 1.06 mmol), (9-ethyl-9H-carbazol-3-yl)methanamine (237 mg, 1.06 mmol), HATU (522 mg, 1.37 mmol) and TEA (0.442 mL, 3.17 mmol) in DMF (5 mL) was stirred at room temperature for 16 hr. To the reaction mixture was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 60% ethyl acetate/hexane), and crystallized from ethyl acetate and hexane to give tert-butyl (1-(((9-ethyl-9H-carbazol-3-yl)methyl)amino)-1-oxopropan-2-yl)carbamate (324 mg, 0.819 mmol, 78%) as a white powder.

$^1$H-NMR (300 MHz, DMSO-$d_6$): δ1.19-1.43 (15H, m), 3.95-4.09 (1H, m), 4.35-4.50 (4H, m), 6.93 (1H, d, J=7.6 Hz), 7.12-7.21 (1H, m), 7.35 (1H, d, J=9.1 Hz), 7.43 (1H, td, J=7.7, 1.1 Hz), 7.56 (2H, dd, J=13.2, 8.3 Hz), 8.03 (1H, s), 8.11 (1H, d, J=7.6 Hz), 8.27 (1H, t, J=5.7 Hz).

(Step 2)

A solution of the compound obtained in Step 1 (324 mg, 0.82 mmol) in TFA (1 mL, 12.98 mmol) was stirred at room temperature for 15 min, and concentrated under reduced pressure. To the residue were added ethyl acetate and 1N aqueous sodium hydroxide solution, and the organic layer was separated. The organic layer was washed with water and saturated brine, and dried, and the solvent was evaporated under reduced pressure to give 2-amino-N-((9-ethyl-9H-carbazol-3-yl)methyl)propanamide (242 mg, 0.819 mmol, 100%) as a white powder.

$^1$H-NMR (300 MHz, DMSO-$d_6$): δ1.11-1.21 (3H, m), 1.22-1.33 (3H, m), 1.81-2.14 (2H, m), 3.19-3.42 (1H, m), 4.29-4.51 (4H, m), 7.05-7.25 (1H, m), 7.30-7.63 (4H, m), 7.93-8.16 (2H, m), 8.22-8.35 (1H, m).

(Step 3)

A solution of the compound obtained in Step 2 (242 mg, 0.82 mmol), 2-(4-cyanophenyl)acetic acid (198 mg, 1.23 mmol), HATU (468 mg, 1.23 mmol) and TEA (0.343 mL, 2.46 mmol) in DMF (3 mL) was stirred at room temperature for 16 hr. To the reaction solution was added dilute hydrochloric acid, and the mixture was extracted with ethyl acetate. The organic layer was washed with dilute hydrochloric acid, and dried, and the solvent was evaporated under reduced pressure. The obtained residue was purified by silica gel column chromatography (solvent: ethyl acetate) to give the title compound (50.3 mg, 0.115 mmol, 14%) as a white powder.

$^1$H-NMR (300 MHz, DMSO-$d_6$): δ1.23-1.40 (6H, m), 3.61 (2H, s), 4.24-4.52 (5H, m), 7.11-7.21 (1H, m), 7.33 (1H, dd, J=8.3, 1.5 Hz), 7.39-7.61 (5H, m), 7.67-7.75 (2H, m), 7.97-8.10 (2H, m), 8.37-8.51 (2H, m).

Example 37

4-cyano-N-(3-{[(9-ethyl-9H-carbazol-3-yl)methyl]amino}-2-methyl-3-oxopropyl)benzamide (Step 1)

Using 3-((tert-butoxycarbonyl)amino)-2-methylpropanoic acid and (9-ethyl-9H-carbazol-3-yl)methanamine, and by the reaction and purification in the same manner as in the method described in Step 1 of Example 36, tert-butyl (3-(((9-ethyl-9H-carbazol-3-yl)methyl)amino)-2-methyl-3-oxopropyl)carbamate was obtained.

$^1$H-NMR (300 MHz, DMSO-$d_6$): δ1.02 (3H, d, J=6.8 Hz), 1.29 (3H, t, J=7.0 Hz), 1.36 (9H, s), 2.53-2.58 (1H, m), 2.90-2.99 (1H, m), 3.14 (1H, dt, J=13.0, 6.3 Hz), 4.33-4.51 (4H, m), 6.75 (1H, t, J=5.5 Hz), 7.14-7.22 (1H, m), 7.36 (1H, dd, J=8.5, 1.7 Hz), 7.44 (1H, ddd, J=8.3, 7.2, 1.1 Hz), 7.56 (2H, dd, J=12.1, 8.3 Hz), 8.00 (1H, d, J=0.8 Hz), 8.11 (1H, d, J=7.6 Hz), 8.34 (1H, t, J=5.7 Hz).

(Step 2)

Using the compound obtained in Step 1, and by the reaction and purification in the same manner as in the method described in Step 2 of Example 36, 3-amino-N-((9-ethyl-9H-carbazol-3-yl)methyl)-2-methylpropanamide was obtained.

$^1$H-NMR (300 MHz, DMSO-$d_6$): δ1.02 (3H, d, J=6.8 Hz), 1.25-1.32 (3H, m), 1.47-1.89 (1H, m), 2.25-2.40 (1H, m), 2.53-2.60 (1H, m), 2.67-2.77 (1H, m), 4.32-4.52 (4H, m), 7.12-7.22 (1H, m), 7.29-7.64 (4H, m), 7.94-8.14 (2H, m), 8.32-8.47 (1H, m).

(Step 3)

Using the compound obtained in Step 2 and 4-cyanobenzoic acid, and by the reaction and purification in the same manner as in the method described in Step 3 of Example 36, the title compound was obtained.

$^1$H-NMR (300 MHz, DMSO-$d_6$): δ1.09 (3H, d, J=6.8 Hz), 1.27 (3H, t, J=7.0 Hz), 2.67-2.81 (1H, m), 3.32-3.46 (2H, m), 4.28 (1H, dd, J=14.7, 4.9 Hz), 4.40 (2H, q, J=7.2 Hz), 4.58 (1H, dd, J=14.7, 6.8 Hz), 7.12-7.20 (1H, m), 7.27-7.33 (1H, m), 7.36-7.47 (2H, m), 7.58 (1H, d, J=8.3 Hz), 7.77-7.84 (2H, m), 7.88-8.04 (4H, m), 8.41 (1H, t, J=5.9 Hz), 8.79 (1H, t, J=5.5 Hz).

Example 38

5-(3-chloro-4-cyanophenoxy)-N-(9-ethyl-9H-carbazol-3-yl)-3-methylpentanamide (Step 1)

To a solution of 9-ethyl-9H-carbazol-3-amine (4.21 g, 20 mmol) in THF (40 mL) was added 3-methylglutaric anhydride (2.56 g, 20.00 mmol), and the mixture was stirred at 90° C. for 4 hr. To the reaction mixture was added water, and the mixture was extracted with ethyl acetate. The organic layer was washed with water and saturated brine, and dried, and the solvent was evaporated under reduced pressure to give 5-(9-ethyl-9H-carbazol-3-ylamino)-3-methyl-5-oxopentanoic acid (6.23 g, 18.41 mmol, 92%) as a white powder.

$^1$H-NMR (300 MHz, DMSO-$d_6$): δ1.00 (3H, d, J=6.1 Hz), 1.30 (3H, t, J=7.0 Hz), 2.07-2.32 (2H, m), 2.32-2.46 (3H, m), 4.41 (2H, q, J=6.9 Hz), 7.17 (1H, t, J=7.4 Hz), 7.43 (1H, t, J=7.6 Hz), 7.49-7.63 (3H, m), 8.05 (1H, d, J=8.0 Hz), 8.41 (1H, s), 9.91 (1H, s), 12.09 (1H, brs)

(Step 2)

To a solution of the compound obtained in Step 1 (1.0 g, 2.96 mmol) in THF (10 mL) was added a THF (5.91 mL, 5.91 mmol) solution of 1M borane-tetrahydrofuran complex at room temperature, and the mixture was stirred for 14 hr. To the reaction mixture was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give N-(9-ethyl-9H-carbazol-3-yl)-5-hydroxy-3-methylpentanamide (0.514 g, 1.586 mmol, 53.7%) as a colorless powder.

$^1$H-NMR (300 MHz, DMSO-$d_6$): δ0.95 (3H, d, J=6.4 Hz), 1.21-1.46 (4H, m), 1.47-1.73 (1H, m), 2.01-2.24 (2H, m), 2.24-2.44 (1H, m), 3.40-3.58 (2H, m), 4.27-4.53 (3H, m), 7.17 (1H, t, J=7.2 Hz), 7.43 (1H, td, J=7.7, 1.1 Hz), 7.49-7.65 (3H, m), 8.05 (1H, d, J=7.6 Hz), 8.41 (1H, d, J=1.5 Hz), 9.85 (1H, s).

(Step 3)

To a solution of the compound obtained in Step 2 (500 mg, 1.54 mmol) and 2-chloro-4-fluorobenzonitrile (240 mg, 1.54 mmol) in THF (15 mL) was added potassium t-butoxide (432 mg, 3.85 mmol) at room temperature, and the mixture was stirred for 14 hr. To the reaction mixture was added water, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 75% ethyl acetate/hexane) to give the title compound (458 mg, 0.996 mmol, 64.6%) as a colorless powder.

$^1$H-NMR (300 MHz, DMSO-$d_6$): δ1.03 (3H, d, J=6.0 Hz), 1.20-1.42 (3H, m), 1.56-1.79 (1H, m), 1.79-2.00 (1H, m), 2.14-2.33 (2H, m), 2.33-2.48 (1H, m), 4.04-4.31 (2H, m), 4.41 (2H, q, J=6.9 Hz), 7.00-7.26 (2H, m), 7.35 (1H, d, J=2.3 Hz), 7.38-7.49 (1H, m), 7.49-7.66 (3H, m), 7.85 (1H, d, J=8.7 Hz), 8.04 (1H, d, J=7.9 Hz), 8.40 (1H, s), 9.91 (1H, s).

Example 39

N-(3-chloro-4-cyanophenyl)-N'-(9-ethyl-9H-carbazol-3-yl)-3-phenylpentanediamide (Step 1)

A solution of 3-phenylpentanedicarboxylic acid (1.0 g, 4.80 mmol) in acetic anhydride (0.453 mL, 4.80 mmol) was stirred at 100° C. for 14 hr. The reaction mixture was concentrated, to the residue was added toluene (10 mL), and 4-amino-2-chlorobenzonitrile (0.733 g, 4.80 mmol) and TEA (0.669 mL, 4.80 mmol) were added thereto. The mixture was stirred at 80° C. for 3 hr, brine was added thereto at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane) to give 5-((3-chloro-4-cyanophenyl)amino)-5-oxo-3-phenylpentanoic acid (1.200 g, 3.50 mmol, 72.9%) as a pale-yellow powder.

MS (API): 341 (M−H)

(Step 2)

A solution of the compound obtained in Step 1 (1.2 g, 3.50 mmol), 9-ethyl-9H-carbazol-3-ylamine (0.736 g, 3.50 mmol), HATU (1.464 g, 3.85 mmol) and TEA (0.537 mL, 3.85 mmol) in DMF (10 mL) was stirred at room temperature for 3 hr. To the reaction mixture was added brine at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 50% ethyl acetate/hexane), and crystallized from ethyl acetate to give the title compound (0.187 g, 0.350 mmol, 9.98%) as white crystals.

$^1$H-NMR (300 MHz, DMSO-$d_6$): δ1.28 (3H, t, J=7.2 Hz), 2.66-2.96 (4H, m), 3.77 (1H, t, J=7.6 Hz), 4.39 (2H, d, J=7.2 Hz), 7.16 (2H, td, J=6.9, 4.3 Hz), 7.23-7.66 (9H, m), 7.82 (1H, d, J=8.7 Hz), 7.91-8.11 (2H, m), 8.29 (1H, d, J=1.5 Hz), 9.88 (1H, s), 10.52 (1H, s).

Example 40

N-(3-chloro-4-cyanophenyl)-N'-(9-ethyl-9H-carbazol-3-yl)cyclobutane-1,2-dicarboxamide (Step 1)

A solution of 4-amino-2-chlorobenzonitrile (1229 mg, 8.06 mmol), 3-oxabicyclo[3.2.0]heptane-2,4-dione (1016 mg, 8.06 mmol) and TEA (1.123 mL, 8.06 mmol) in toluene (10 mL) was stirred at 80° C. for 14 hr. To the reaction mixture was added brine at room temperature, and the mixture was extracted with ethyl acetate. The organic layer was washed with water and saturated brine, and dried, and the solvent was evaporated under reduced pressure. The obtained residue was purified by COOH-silica gel column chromatography (solvent gradient; 10 to 100% ethyl acetate/hexane), and crystallized from ethyl acetate to give 2-((3-chloro-4-cyanophenyl) carbamoyl)cyclobutanecarboxylic acid (795 mg, 2.85 mmol, 35.4%) as colorless crystals.

MS (API): 277 (M−H)

(Step 2)

A solution of the compound obtained in Step 1 (795 mg, 2.85 mmol), 9-ethyl-9H-carbazol-3-amine (600 mg, 2.85 mmol), HATU (1085 mg, 2.85 mmol) and TEA (0.437 mL, 3.14 mmol) in DMF (5 mL) was stirred at room temperature for 14 hr. To the reaction mixture was added brine at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane), and crystallized from ethyl acetate and ethanol to give the title compound (82 mg, 0.174 mmol, 6.10%) as colorless crystals.

$^1$H-NMR (300 MHz, DMSO-$d_6$): δ1.28 (3H, t, J=7.0 Hz), 2.07-2.25 (1H, m), 2.25-2.45 (4H, m), 3.47-3.74 (1H, m), 4.39 (2H, d, J=7.2 Hz), 7.15 (1H, t, J=7.0 Hz), 7.33-7.49 (3H, m), 7.50-7.66 (2H, m), 7.80 (1H, d, J=8.7 Hz), 7.90 (1H, d, J=7.6 Hz), 8.01 (1H, d, J=1.9 Hz), 8.16 (1H, d, J=1.1 Hz), 9.64 (1H, brs), 10.28 (1H, brs).

Example 41

N-(4-cyano-3-methoxyphenyl)-N'-(9-ethyl-9H-carbazol-3-yl)-3-methylpentanediamide (Step 1)

A solution of 2-methoxy-4-nitrobenzonitrile (750 mg, 4.21 mmol) and palladium on carbon (50 mg, 0.47 mmol) in methanol (15 mL) was stirred at room temperature for 48 hr under hydrogen atmosphere (1 atm). The catalyst was removed by filtration, and the filtrate was concentrated under reduced pressure to give 4-amino-2-methoxybenzonitrile (679 mg, 4.58 mmol, quantitative) as a brownish-red powder.

$^1$H-NMR (300 MHz, DMSO-$d_6$): δ3.32 (3H, s), 6.05-6.29 (4H, m), 7.23 (1H, d, J=8.3 Hz).

(Step 2)

A solution of the compound obtained in Step 1 (670 mg, 4.52 mmol) and 3-methylglutaric anhydride (579 mg, 4.52 mmol) in THF (20 mL) was heated with reflux for 14 hr. The reaction solution was concentrated under reduced pressure to give 5-((4-cyano-3-methoxyphenyl)amino)-3-methyl-5-oxopentanoic acid (1.35 g, 4.89 mmol, quantitative) as a brownish-red oil.

$^1$H-NMR (300 MHz, DMSO-$d_6$): δ0.75-1.12 (3H, m), 1.58-1.91 (1H, m) 2.08-2.19 (1H, m), 2.22-2.46 (2H, m), 2.48-2.55 (1H, m), 2.65-2.94 (1H, m), 3.36 (1H, brs), 3.60 (1H, t, J=6.4 Hz), 7.25 (1H, dd, J=8.3, 1.5 Hz), 7.45-7.76 (2H, m), 10.34 (1H, s), 12.11 (1H, brs).

(Step 3)

To a solution of the compound obtained in Step 2 (1.20 g, 4.34 mmol), 9-ethyl-9H-carbazol-3-amine (0.913 g, 4.34 mmol) and DIEA (1.896 mL, 10.86 mmol) in DMF (15 mL) was added HATU (1.982 g, 5.21 mmol), and the mixture was stirred at room temperature for 4 hr. To the reaction mixture was added water, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 85% ethyl acetate/hexane), and purified by NH-silica gel column chromatography (solvent gradient; 10 to 100% ethyl acetate/hexane) to give the title compound (0.788 g, 1.681 mmol, 38.7%) as a colorless powder.

$^1$H-NMR (300 MHz, DMSO-$d_6$): δ1.04 (3H, d, J=6.0 Hz), 1.30 (3H, t, J=7.0 Hz), 2.22-2.49 (4H, m), 2.53-2.64 (1H, m), 3.86 (3H, s), 4.41 (2H, q, J=7.2 Hz), 7.07-7.34 (2H, m), 7.36-7.70 (6H, m), 8.04 (1H, d, J=7.6 Hz), 8.31-8.50 (1H, m), 9.94 (1H, s), 10.39 (1H, s).

Example 42

$N^5$-(3-chloro-4-cyanophenyl)-$N^1$-(9-ethyl-9H-carbazol-3-yl)-2-methylpentanediamide

Example 43

$N^1$-(3-chloro-4-cyanophenyl)-$N^5$-(9-ethyl-9H-carbazol-3-yl)-2-methylpentanediamide (Step 1)

A solution of 3-methyldihydro-2H-pyran-2,6(3H)-dione (876 mg, 6.84 mmol), 4-amino-2-chlorobenzonitrile (1044 mg, 6.84 mmol) and TEA (0.953 mL, 6.84 mmol) in toluene (10 mL) was stirred at 70° C. for 3 hr. To the reaction mixture was added brine at room temperature, and the mixture was extracted with ethyl acetate. The organic layer was washed with water and saturated brine, and dried, and the solvent was evaporated under reduced pressure. The obtained residue was purified by COOH-silica gel column chromatography (solvent gradient; 10 to 100% ethyl acetate/hexane) to give a mixture (750 mg, 2.67 mmol, 39.1%) of 5-((3-chloro-4-cyanophenyl)amino)-2-methyl-5-oxopentanoic acid and 5-((3-chloro-4-cyanophenyl)amino)-4-methyl-5-oxopentanoic acid, as a colorless powder.

MS (API): 279 (M−H)

(Step 2)

A solution of the mixture obtained in Step 2 (750 mg, 2.67 mmol), HATU (1117 mg, 2.94 mmol), 3-amino-9-ethylcarbazole (590 mg, 2.81 mmol) in DMF (5 mL) was stirred at room temperature for 14 hr. To the reaction mixture was added brine at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 100% ethyl acetate/hexane), and purified by preparative HPLC (column: L-Column 2 ODS, eluent: 0.1% TFA-containing acetonitrile/water) to give the compound of Example 42 (42.0 mg, 0.089 mmol, 3.32%) and the compound of Example 43 (20.00 mg, 0.042 mmol, 1.583%), each as a white powder.

The Compound of Example 42

$^1$H-NMR (300 MHz, $CDCl_3$): δ1.29-1.42 (6H, m), 1.86-2.02 (2H, m), 2.31-2.52 (2H, m), 2.62 (1H, d, J=6.8 Hz), 4.18-4.44 (2H, m), 7.14-7.25 (2H, m), 7.28-7.41 (4H, m), 7.42-7.51 (1H, m), 7.67-7.81 (2H, m), 7.87 (1H, d, J=4.5 Hz), 8.12 (1H, d, J=1.5 Hz), 9.18 (1H, brs).

The Compound of Example 43

$^1$H-NMR (300 MHz, $CDCl_3$): δ1.24-1.48 (6H, m), 1.78-1.98 (1H, m), 2.05-2.19 (1H, m), 2.36-2.63 (2H, m), 2.67-

2.94 (1H, m), 4.35 (2H, q, J=6.9 Hz), 7.12-7.24 (1H, m), 7.29-7.73 (7H, m), 7.88-8.09 (2H, m), 8.21 (1H, s), 9.66 (1H, s).

Example 44

5-(4-cyano-3-methylphenoxy)-N-(9-ethyl-9H-carbazol-3-yl)-3-methylpentanamide

To a solution of N-(9-ethyl-9H-carbazol-3-yl)-5-hydroxy-3-methylpentanamide (0.34 g, 1.05 mmol) in DMF (8.0 mL) was added potassium-t-butoxide (0.258 g, 2.31 mmol) under argon atmosphere. The mixture was stirred at room temperature for 15 min, and 4-fluoro-2-methylbenzonitrile (0.212 g, 1.57 mmol) was added thereto. The reaction solution was stirred at room temperature for 14 hr, and ethyl acetate (80 mL) was added thereto. The organic layer was washed with cold water (2×20 mL) and saturated brine (2×20 mL), and dried, and the solvent was evaporated under reduced pressure. The obtained residue was purified by silica gel column chromatography (solvent gradient; 20 to 30% ethyl acetate/hexane) to give the title compound (0.16 g, 35%) as a white powder.

$^1$H-NMR (300 MHz, DMSO-$d_6$): δ1.01 (3H, d, J=6.1 Hz), 1.29 (3H, t, J=7.2 Hz), 1.66-1.70 (1H, m), 1.84-1.87 (1H, m), 2.23-2.27 (2H, m), 2.40-2.44 (4H, m), 4.14 (2H, dd, J=10.9, 6.6 Hz), 4.41 (2H, q, J=7.1 Hz), 6.93 (1H, dd, J=2.4, 8.6 Hz), 7.04 (1H, d, J=2.2 Hz), 7.16 (1H, t, J=7.2 Hz), 7.41-7.45 (1H, m), 7.53 (2H, brs), 7.57 (1H, d, J=8.2 Hz), 7.65 (1H, d, J=8.6 Hz), 8.04 (1H, d, J=7.7 Hz), 8.39 (1H, brs), 9.91 (1H, brs).

Example 45

5-[(5-cyano-6-methylpyridin-2-yl)oxy]-N-(9-ethyl-9H-carbazol-3-yl)-3-methylpentanamide Using 2-fluoro-5-cyano-6-methylpyridine, and by the reaction and purification in the same manner as in the method described in Example 44, the title compound was obtained.

$^1$H-NMR (300 MHz, DMSO-$d_6$): δ1.01 (3H, d, J=6.1 Hz), 1.29 (3H, t, J=7.1 Hz), 1.66-1.69 (1H, m,), 1.84-1.87 (1H, m), 2.20-2.26 (2H, m), 2.37-2.40 (1H, m), 2.53 (3H, s), 4.38-4.45 (4H, m), 6.80 (1H, d, J=8.6 Hz), 7.16 (1H, t, J=7.4 Hz), 7.43 (1H, t, J=7.6 Hz), 7.52 (2H, brs), 7.57 (1H, d, J=8.2 Hz), 8.03 (2H, d, J=8.6 Hz), 8.38 (1H, brs), 9.91 (1H, brs).

Example 46

5-[(5-cyanopyridin-2-yl)oxy]-N-(9-ethyl-9H-carbazol-3-yl)-3-methylpentanamide

Using 5-cyano-2-fluoropyridine, and by the reaction and purification in the same manner as in the method described in Example 44, the title compound was obtained.

$^1$H-NMR (300 MHz, DMSO-$d_6$): δ1.01 (3H, d, J=6.2 Hz), 1.29 (3H, t, J=7.1 Hz), 1.65-1.70 (1H, m), 1.87-1.90 (1H, m), 2.21-2.26 (2H, m), 2.37-2.41 (1H, m), 4.38-4.47 (4H, m), 6.99 (1H, d, J=8.7 Hz), 7.16 (1H, t, J=7.4 Hz), 7.41 (1H, t, J=7.3 Hz), 7.52-7.58 (3H, m), 8.04 (1H, d, J=7.7 Hz), 8.12 (1H, dd, J=2.3, 8.7 Hz), 8.38 (1H, brs), 8.67 (1H, d, J=2.0 Hz), 9.90 (1H, brs).

Example 47

5-[(6-cyanopyridin-3-yl)oxy]-N-(9-ethyl-9H-carbazol-3-yl)-3-methylpentanamide

Using 2-cyano-5-fluoropyridine, and by the reaction and purification in the same manner as in the method described in Example 44, the title compound was obtained.

$^1$H-NMR (300 MHz, DMSO-$d_6$): δ1.02 (3H, d, J=6.2 Hz), 1.29 (3H, t, J=7.1 Hz), 1.70-1.73 (1H, m), 1.87-1.91 (1H, m), 2.24-2.28 (2H, m), 2.38-2.49 (1H, m), 4.23-4.27 (2H, m), 4.41 (2H, q, J=7.0 Hz), 7.16 (1H, t, J=7.0 Hz), 7.43 (1H, t, J=7.1 Hz), 7.52 (2H, brs), 7.58-7.62 (2H, m), 7.98 (1H, d, J=8.6 Hz), 8.04 (1H, d, J=7.7 Hz), 8.38 (1H, brs), 8.44 (1H, d, J=2.8 Hz), 9.91 (1H, brs).

Example 48

N-{4-[(3-chloro-4-cyanophenyl)amino]-2-methyl-4-oxobutyl}-9-ethyl-9H-carbazole-3-carboxamide (Step 1)

A solution of crotonic acid (8.24 mL, 98.31 mmol) and thionyl chloride (7.18 mL, 98.31 mmol) in DMA (150 mL) was stirred at 0° C. for 1 hr. To the reaction mixture was added 4-amino-2-chlorobenzonitrile (15 g, 98.31 mmol), and the mixture was stirred at room temperature for additional 14 hr. To the reaction solution was added brine at room temperature, and the mixture was extracted with ethyl acetate. The organic layer was washed with 1N aqueous sodium hydroxide solution and 1N hydrochloric acid, and dried, and the solvent was evaporated under reduced pressure to give (E)-N-(3-chloro-4-cyanophenyl)but-2-enamide (21.69 g, 98.31 mmol, quantitative) as a brownish-red powder.

MS (API): 229 (M−H)

(Step 2)

The compound obtained in Step 1 (21.69 g, 98.31 mmol), DBU (16.30 mL, 108.14 mmol) and nitromethane (6.00 g, 98.31 mmol) were stirred at room temperature for 14 hr. To the reaction solution was added brine at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 5 to 30% ethyl acetate/hexane) to give N-(3-chloro-4-cyanophenyl)-3-methyl-4-nitrobutanamide (21.20 g, 75 mmol, 77%) as a pale-orange powder.

$^1$H-NMR (300 MHz, $CDCl_3$): δ1.18 (3H, d, J=7.2 Hz), 2.35-2.69 (2H, m), 2.75-3.06 (1H, m), 4.50 (2H, t, J=5.7 Hz), 7.41-7.54 (1H, m), 7.53-7.69 (1H, m), 7.71-7.83 (1H, m), 7.91 (1H, d, J=2.3 Hz).

(Step 3)

A solution of the compound obtained in Step 2 (21.2 g, 75.26 mmol), iron powder (21.01 g, 376.29 mmol) and calcium chloride (25.06 g, 225.78 mmol) in a mixed solvent of methanol (100 mL) and water (20 mL) was stirred at 60° C. for 3 hr. To the reaction solution was added brine at room temperature, and the mixture was extracted with ethyl acetate. The organic layer was washed with water and saturated brine, and dried, and the solvent was evaporated under reduced pressure. The obtained residue was purified by NH-silica gel column chromatography (solvent gradient; 10 to 50% ethyl acetate/hexane) to give 4-amino-N-(3-chloro-4-cyanophenyl)-3-methylbutanamide (6.02 g, 23.92 mmol, 31.8%) as a brown oil.

MS (API): 252 (M+H)

(Step 4)

A solution of the compound obtained in Step 3 (158 mg, 0.63 mmol), 9-ethyl-9H-carbazole-3-carboxylic acid (150 mg, 0.63 mmol), HATU (262 mg, 0.69 mmol) and TEA (0.096 mL, 0.69 mmol) in DMF (5 mL) was stirred at 50° C. for 14 hr. To the reaction solution was added brine at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 80% ethyl acetate/hexane) to give the title compound (156 mg, 0.330 mmol, 52.6%) as white crystals.

$^1$H-NMR (300 MHz, DMSO-$d_6$): δ0.99 (3H, d, J=6.8 Hz), 1.33 (3H, t, J=7.2 Hz), 2.13-2.43 (2H, m), 3.24-3.31 (1H, m), 4.47 (2H, d, J=7.2 Hz), 7.25 (1H, t, J=7.4 Hz), 7.42-7.69 (4H, m), 7.77 (1H, d, J=8.7 Hz), 7.93-8.03 (2H, m), 8.13 (1H, d, J=7.9 Hz), 8.47 (1H, t, J=5.7 Hz), 8.66 (1H, d, J=1.5 Hz), 10.54 (1H, s).

MS (API): 473 (M+H)

Example 49

N-(6-cyanopyridin-3-yl)-N'-(9-ethyl-9H-carbazol-3-yl)-3-methylpentanediamide (Step 1)

A solution of 5-aminopyridine-2-carbonitrile (300.0 mg, 2.518 mmol) and 4-methyldihydro-2H-pyran-2,6(3H)-dione (354.931 mg, 2.77 mmol) in a mixed solvent of toluene (7 mL) and DMSO (0.7 mL) was stirred at 110° C. for 16 hr. To the reaction mixture was added cold water, and the mixture was extracted with ethyl acetate (4×30 mL). The organic layer was washed with water, and dried, and the solvent was evaporated under reduced pressure. The obtained solid was washed with 50% dichloromethane/hexane solution to give 4-(6-cyanopyridin-3-ylcarbamoyl)-3-methylbutyric acid (300 mg, 48.2%) as a pale-yellow powder.

$^1$H-NMR (300 MHz, DMSO-$d_6$): δ0.96 (3H, d, J=5.8 Hz), 2.12-2.50 (5H, m), 7.97 (1H, d, J=8.6 Hz), 8.27 (1H, dd, J=8.60, 2.2 Hz), 8.84 (1H, d, J=2.0 Hz), 10.59 (1H, s), 12.12 (1H, brs).

(Step 2)

To a solution of 9-ethyl-9H-carbazol-3-ylamine (306.5 mg, 1.457 mmol) in DMF (7 mL) were added the compound obtained in Step 1 (300 mg, 1.215 mmol), HATU (554.14 mg, 1.457 mmol) and DIPEA (0.632 mL, 3.644 mmol) at room temperature, and the mixture was stirred at room temperature for 16 hr. To the reaction mixture was added water, and the mixture was extracted with ethyl acetate (2×50 mL). The organic layer was dried, and the solvent was evaporated under reduced pressure. The obtained residue was purified by preparative HPLC to give the title compound (260 mg, 48.71%) as a colorless powder.

$^1$H-NMR (300 MHz, DMSO-$d_6$): δ1.03 (3H, d, J=6.2 Hz), 1.29 (3H, t, J=7.0 Hz), 2.29-2.50 (5H, m), 4.38-4.44 (2H, m), 7.17 (1H, t, J=7.4 Hz), 7.44 (1H, t, J=7.6 Hz), 7.51-7.58 (3H, m), 7.96 (1H, d, J=8.6 Hz), 8.03 (1H, d, J=7.6 Hz), 8.28 (vdd, J=8.6, 2.4 Hz), 8.40 (1H, s), 8.86 (1H, s), 9.93 (1H, s), 10.64 (1H, s).

Purification Condition by Preparative HPLC equipment: Waters Semi-Preparative HPLC instrument column: Prep Scalar 10 μm C18 (250×30 mm)

solvent: A=0.05% aqueous formic acid solution, B=acetonitrile solvent gradient: 60% A/B (0 min)→40% A/B (60 min)→5% A/B (61 min)→5% A/B (70 min)→60% A/B (71 min)

flow rate: 30 mL/min temperature: room temperature

Example 50

N-(5-cyanopyridin-2-yl)-N'-(9-ethyl-9H-carbazol-3-yl)-3-methylpentanediamide (Step 1)

A solution of 6-aminonicotinonitrile (100.0 mg, 0.839 mmol) and 4-methyldihydro-2H-pyran-2,6(3H)-dione (118 mg, 0.923 mmol) in a mixed solvent of toluene (3 mL) and DMSO (0.3 mL) was stirred at 120° C. for 24 hr. To the reaction mixture was added cold water, and the mixture was extracted with ethyl acetate (4×30 mL). The organic layer was washed with water, and dried, and the solvent was evaporated under reduced pressure. The obtained solid was washed with 50% dichloromethane/hexane solution to give 4-(5-cyanopyridin-2-ylcarbamoyl)-3-methylbutyric acid (30 mg, 14.49%) as a pale-yellow powder.

$^1$H-NMR (300 MHz, DMSO-$d_6$): δ0.94 (3H, d, J=6.1 Hz), 2.06-2.50 (5H, m), 7.01 (1H, s), 8.23 (1H, s), 8.77 (1H, s), 10.98 (1H, s), 12.09 (1H, brs).

(Step 2)

To a solution of 9-ethyl-9H-carbazol-3-ylamine (306.5 mg, 1.457 mmol) in DMF (7 mL) were added the compound obtained in Step 1 (300 mg, 1.215 mmol), HATU (554.14 mg, 1.457 mmol) and DIPEA (0.632 mL, 3.644 mmol) at room temperature, and the mixture was stirred at room temperature for 16 hr. To the reaction mixture was added water, and the mixture was extracted with ethyl acetate (2×50 mL). The organic layer was dried, and the solvent was evaporated under reduced pressure. The obtained residue was purified by preparative HPLC to give the title compound (220 mg, 41.21%) as a colorless powder.

$^1$H-NMR (300 MHz, DMSO-$d_6$): δ1.01 (3H, d, J=6.0 Hz) 1.29 (3H, t, J=7.0 Hz), 2.27-2.50 (5H, m), 4.38-4.44 (2H, m), 7.16 (1H, t, J=7.6 Hz), 7.43 (1H, t, J=7.4 Hz), 7.53-7.58 (3H, m), 8.03 (1H, d, J=7.7 Hz), 8.21-8.28 (2H, m), 8.40 (1H, s), 8.77 (1H, s), 9.92 (1H, s), 11.03 (1H, s).

Purification Condition by Preparative HPLC

The Same as Example 49

Example 51

N-{4-[(3-chloro-4-cyanophenyl)amino]-1-ethyl-2-methyl-4-oxobutyl}-9-ethyl-9H-carbazole-3-carboxamide (Step 1)

A solution of the compound obtained in Step 1 of Example 48 (1.2 g, 5.44 mmol) and DBU (0.984 mL, 6.53 mmol) in 1-nitropropane (2.420 mL, 27.19 mmol) was stirred at 60° C. for 2 hr. To the reaction solution was added brine at room temperature, and the mixture was extracted with ethyl acetate. The organic layer was washed with water and saturated brine, and dried, and the solvent was evaporated under reduced pressure. The obtained residue was purified by silica gel column chromatography (solvent gradient; 10 to 30% ethyl acetate/hexane) to give N-(3-chloro-4-cyanophenyl)-3-methyl-4-nitrohexanamide (1.420 g, 4.58 mmol, 84%) as a pale-yellow oil.

$^1$H-NMR (300 MHz, $CDCl_3$): δ0.88-1.18 (6H, m), 1.66-1.94 (1H, m), 2.09-2.74 (4H, m), 4.38-4.59 (1H, m), 7.49 (1H, td, J=4.2, 2.1 Hz), 7.55-7.67 (1H, m), 7.92 (2H, dd, J=4.7, 2.1 Hz).

(Step 2)

Using the compound obtained in Step 1, and by the reaction and purification in the same manner as in the method described in Step 3 of Example 48, 4-amino-N-(3-chloro-4-cyanophenyl)-3-methylhexanamide was obtained as a crude product.

MS (API): 278 (M−H)

(Step 3)

Using the compound obtained in Step 2, and by the reaction and purification in the same manner as in the method described in Step 4 of Example 48, the title compound was obtained.

MS (API): 501 (M+H)

Example 52

N-(3-chloro-4-cyanophenyl)-N'-(6-chloro-1-methyl-1H-indol-5-yl)-3-methylpentanediamide Using 5-(3-chloro-4-cyanophenylamino)-3-methyl-5-oxopentanoic acid and 6-chloro-1-methyl-1H-indol-5-amine, and by the reaction and purification in the same manner as in the method described in Step 2 of Example 3, the title compound was obtained.

MS (API): 443 (M+H)

Example 53

5-(4-cyano-3-methoxyphenoxy)-N-(9-ethyl-9H-carbazol-3-yl)-3-methylpentanamide

Using N-(9-ethyl-9H-carbazol-3-yl)-5-hydroxy-3-methylpentanamine and 4-fluoro-2-methoxybenzonitrile, and by the reaction and purification in the same manner as in the method described in Example 44, the title compound was obtained.

$^1$H-NMR (300 MHz, DMSO-$d_6$): δ1.01 (3H, d, J=6.0 Hz), 1.29 (3H, t, J=7.1 Hz), 1.65-1.70 (1H, m), 1.86-1.89 (1H, m), 2.24-2.28 (2H, m), 2.38-2.43 (1H, m), 3.9 (3H, s), 4.15-4.19 (2H, m), 4.41 (2H, q, J=7.0 Hz), 6.7 (1H, dd, J=2.0, 8.7 Hz), 6.73-6.74 (1H, m), 7.17 (1H, t, J=7.5 Hz), 7.43 (1H, d, J=7.6 Hz), 7.53-7.62 (4H, m), 8.04 (1H, d, J=7.7 Hz), 8.39 (1H, s), 9.91 (1H, brs).

Example 54

5-(4-cyano-3,5-dimethylphenoxy)-N-(9-ethyl-9H-carbazol-3-yl)-3-methylpentanamide Using N-(9-ethyl-9H-carbazol-3-yl)-5-hydroxy-3-methylpentanamine and 4-fluoro-2,6-dimethylbenzonitrile, and by the reaction and purification in the same manner as in the method described in Example 44, the title compound was obtained.

$^1$H-NMR (300 MHz, DMSO-$d_6$): δ1.01 (3H, d, J=6.0 Hz), 1.29 (3H, t, J=7.0 Hz), 1.64-1.69 (1H, m), 1.85-1.86 (1H, m), 2.23-2.27 (3H, m), 2.38 (6H, s), 4.11-4.12 (2H, m), 4.41 (2H, q, J=6.8 Hz), 6.84 (2H, s), 7.16 (1H, t, J=7.26 Hz), 7.43 (1H, d, J=7.2 Hz), 7.53-7.58 (3H, m), 8.03 (1H, d, J=7.5 Hz), 8.39 (1H, s), 9.91 (1H, brs)

Example 55

5-(3,4-dicyanophenoxy)-N-(9-ethyl-9H-carbazol-3-yl)-3-methylpentanamide

To a solution of N-(9-ethyl-9H-carbazol-3-yl)-5-hydroxy-3-methylpentanamine (0.40 g, 1.23 mmol) in DMF (10.0 mL) was added potassium-t-butoxide (0.304 g, 2.71 mmol) under argon atmosphere. The mixture was stirred at room temperature for 15 min, and 4-fluorophthalonitrile (0.270 g, 1.85 mmol) was added thereto. The reaction solution was stirred at room temperature for 14 hr, and ethyl acetate (100 mL) was added thereto. The organic layer was washed with cold water (2×25 mL) and saturated brine (2×25 mL), and dried, and the solvent was evaporated under reduced pressure. The obtained residue was purified by preparative HPLC to give the title compound (0.285 g, 51%) as a white powder.

$^1$H-NMR (300 MHz, DMSO-$d_6$): δ0.99 (3H, d, J=5.9 Hz), 1.26 (3H, t, J=7.0 Hz), 1.64-1.69 (1H, m), 1.83-1.88 (1H, m), 2.21-2.25 (2H, m), 2.37-2.39 (1H, m), 4.18-4.21 (2H, m), 4.37 (2H, q, J=6.8 Hz), 7.13 (1H, t, J=7.2 Hz), 7.38-7.43 (2H, m), 7.49-7.55 (3H, m), 7.74 (1H, d, J=2.20 Hz), 7.99 (2H, t, J=9.2 Hz), 8.34 (1H, s), 9.86 (1H, brs).

Purification Condition by Preparative HPLC equipment: Waters Semi-Preparative HPLC instrument column: Prep Scalar 10 μm C18 (250×30 mm)

solvent: A=5 mM aqueous ammonium acetate solution, B=acetonitrile solvent gradient: 50% A/B (0 min)→30% A/B (60 min)→5% A/B (65 min)→5% A/B (75 min)→50% A/B (76 min)

flow rate: 30 mL/min temperature: room temperature

Example 56

4-((4-cyanobenzyl)oxy)-N-(9-ethyl-9H-carbazol-3-yl)-3-methylbutanamide (Step 1)

To a solution of 2,4-dimethoxybenzaldehyde (4 g, 24.07 mmol) in toluene (440 mL) was added 9-ethyl-9H-carbazol-3-ylamine (7.58 g, 36.1 mmol), and titanium(IV) isopropoxide (10.8 mL, 36.1 mmol) was added dropwise thereto. The mixture was heated with reflux for 14 hr, cooled, and concentrated under reduced pressure. The obtained residue was dissolved in dichloromethane (440 mL), methanol (440 mL) was added thereto, and the mixture was cooled to 0° C. Sodium borohydride (1.82 g, 48.14 mmol) was slowly added thereto, the mixture was stirred for 30 min, and cold water (200 mL) was added thereto. The insoluble substance was removed by filtration through Celite, and washed with dichloromethane (100 mL×2). The organic layer was separated, and the aqueous layer was extracted with dichloromethane (100 mL×3). The organic layers were combined, washed with saturated brine, and dried, and the solvent was evaporated under reduced pressure. The obtained residue was purified by silica gel column chromatography (solvent; 30% ethyl acetate/hexane) to give 2,4-dimethoxybenzyl)-(9-ethyl-9H-carbazol-3-yl)-amine (8 g, 92.2%) as a white powder.

$^1$H-NMR (300 MHz, DMSO-$d_6$): δ1.24 (3H, t, J=7.1 Hz), 3.71 (3H, s), 3.85 (3H, s), 4.22 (2H, d, J=6.0 Hz), 4.31 (2H, q, J=7.1 Hz), 5.54 (1H, t, J=6.1 Hz), 6.44 (1H, dd, J=2.3, 8.3 Hz), 6.57 (1H, d, J=2.2 Hz), 6.87 (1H, dd, J=2.1, 8.7 Hz), 7.05 (1H, t, J=7.5 Hz), 7.24-7.26 (2H, m), 7.30-7.35 (2H, m), 7.45 (1H, d, J=8.2 Hz), 7.93 (1H, d, J=7.6 Hz).

(Step 2)

To a solution of the compound obtained in Step 1 (8 g, 22.22 mmol) in dichloromethane (100 mL) was added 3-methyldihydrofuran-2,5-dione (2.78 g, 24.44 mmol) at 0° C., and the mixture was stirred at room temperature for 4 hr. The reaction solution was concentrated under reduced pressure, and the precipitate was triturated with 20% ethyl acetate/hexane to give a mixture (10.4 g, 98.6%) of N-(2,4-dimethoxybenzyl)-N-(9-ethyl-9H-carbazol-3-yl)-2-methylsuccinamidic acid and a regioisomer thereof, as a white powder. The regioisomeric mixture was used for the next step without purification.

(Step 3)

To a solution of the regioisomeric mixture (10.4 g, 21.94 mmol) obtained in Step 2 in THF (300 mL) was added 2M borane-dimethyl sulfide THF solution (10.75 mL, 21.5 mmol) at 0° C., and the mixture was stirred at room temperature for 4 hr. The reaction solution was concentrated under reduced pressure, and the residue was dissolved in ethyl acetate (200 mL). The solution was washed with water (100 mL) and saturated brine (100 mL), and dried, and the solvent was evaporated under reduced pressure. The obtained residue was purified by silica gel column chromatography (solvent; 4% methanol/dichloromethane) to give a mixture (6 g, 59.4%) of N-(2,4-dimethoxybenzyl)-N-(9-ethyl-9H-carbazol-3-yl)-4-hydroxy-3-methylbutylamide and a regioisomer thereof, as a white powder. The regioisomeric mixture was used for the next step without further purification.

(Step 4)

To a solution of the regioisomeric mixture (2 g, 4.35 mmol) obtained in Step 3 in DMF (25 mL) was added sodium hydride (60% oil, 261 mg, 6.52 mmol) at 0° C., and the mixture was stirred at the same temperature for 30 min. 4-Cyanobenzyl bromide (2.55 g, 13.05 mmol) was added thereto at 0° C., and the mixture was stirred at room temperature for 24 hr. To the reaction solution was added water (50 mL), and the mixture was extracted with ethyl acetate (100 mL×2). The organic layer was dried, and the solvent was evaporated under reduced pressure. The obtained residue was purified by silica gel column chromatography (solvent; 30% ethyl acetate/hexane) to give a mixture (1 g, 40%) of 4-(4-cyanobenzyloxy)-N-(2,4-dimethoxybenzyl)-N-(9-ethyl-9H-carbazol-3-yl)-3-methylbutylamide and a regioisomer thereof, as a white powder. The regioisomeric mixture was used for the next step without further purification.

(Step 5)

To a solution of the regioisomeric mixture (1 g, 1.74 mmol) obtained in Step 4 in TFA (20 mL) was added anisole (2 mL) at 0° C., and the mixture was stirred at 50° C. for 16 hr, and then stirred at room temperature for 24 hr. The reaction solution was concentrated under reduced pressure, and the obtained residue was purified by preparative HPLC to give the title compound (0.035 g, 4.7%) as a white powder.

$^1$H-NMR (300 MHz, DMSO-$d_6$): δ1.00 (3H, d, J=6.6 Hz), 1.29 (3H, t, J=7.0 Hz), 2.19-2.25 (1H, m), 2.31-2.34 (1H, m), 2.44-2.47 (1H, m), 3.41 (2H, t, J=5.2 Hz), 4.41 (2H, q, J=7.0 Hz), 4.59 (2H, s), 7.16 (1H, t, J=7.4 Hz), 7.43 (1H, t, J=7.6 Hz), 7.50-7.58 (5H, m), 7.77 (2H, d, J=8.1 Hz), 8.03 (1H, d, J=7.4 Hz), 8.39 (1H, s), 9.89 (1H, s).

Purification Condition by Preparative HPLC equipment: Waters Semi-Preparative HPLC instrument column: Prep Scalar 10 μm C18 (250×30 mm)

solvent: A=5 mM aqueous ammonium acetate solution, B=acetonitrile solvent gradient: 50% A/B (0 min)→45% A/B (15 min) →40% A/B (60 min)→5% A/B (61 min)→5% A/B (70 min) →50% A/B (71 min)

flow rate: 30 mL/min temperature: room temperature

The compounds described in Examples 1 to 56 are as follows (Table 1). The “free” shown in Table 1 means a free form.

TABLE 1
| Example No. | 1 | 2 | 3 |
|---|---|---|---|
| structural formula | 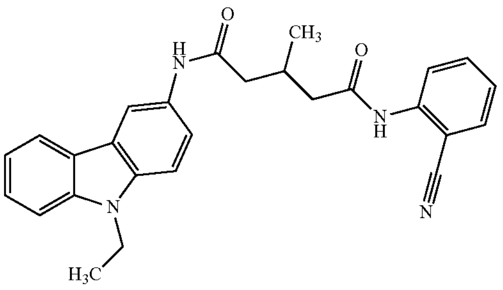 [SMILES: CCn1c2ccccc2c2cc(NC(=O)CC(C)CC(=O)Nc3ccccc3C#N)ccc21] | 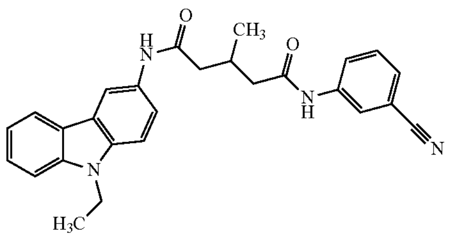 [SMILES: CCn1c2ccccc2c2cc(NC(=O)CC(C)CC(=O)Nc3cccc(C#N)c3)ccc21] | 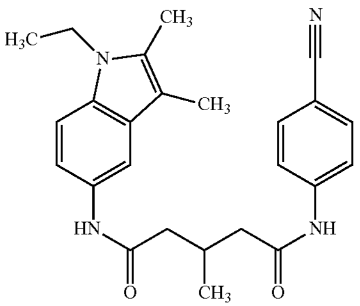 [SMILES: CCn1c(C)c(C)c2cc(NC(=O)CC(C)CC(=O)Nc3ccc(C#N)cc3)ccc21] |
| salt | free | free | free |
| Example No. | 4 | 5 | 6 |
| structural formula | 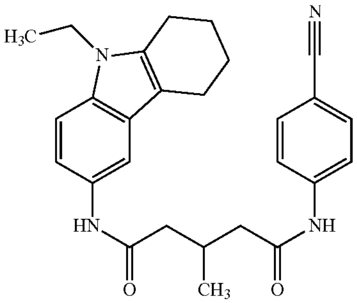 [SMILES: CCn1c2c(c3cc(NC(=O)CC(C)CC(=O)Nc4ccc(C#N)cc4)ccc31)CCCC2] | 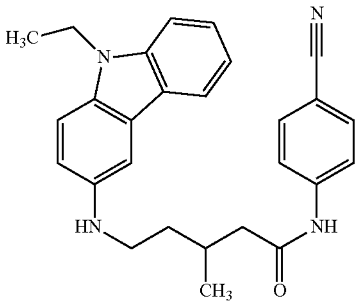 [SMILES: CCn1c2ccccc2c2cc(NCCC(C)CC(=O)Nc3ccc(C#N)cc3)ccc21] | 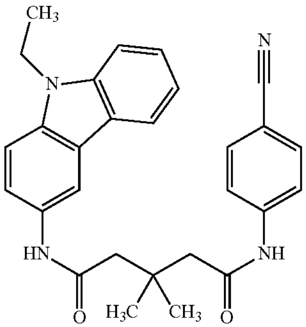 [SMILES: CCn1c2ccccc2c2cc(NC(=O)CC(C)(C)CC(=O)Nc3ccc(C#N)cc3)ccc21] |

TABLE 1-continued
| salt | free | free | free |
|---|---|---|---|
| Example No. | 7 | 8 | 9 |
| structural formula | 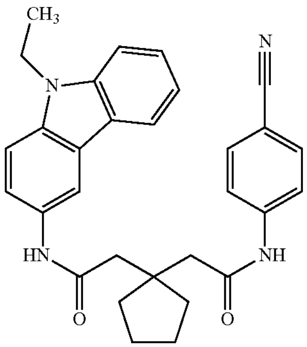 [SMILES: CCn1c2ccccc2c2cc(NC(=O)CC3(CC(=O)Nc4ccc(C#N)cc4)CCCC3)ccc21] | 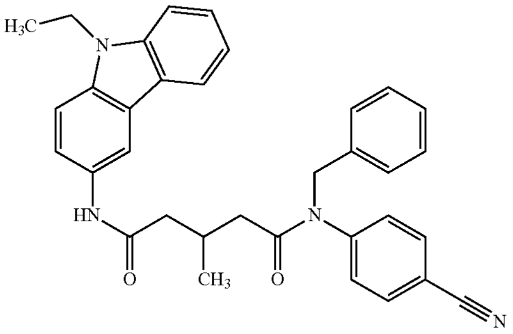 [SMILES: CCn1c2ccccc2c2cc(NC(=O)CC(C)CC(=O)N(Cc3ccccc3)c3ccc(C#N)cc3)ccc21] | 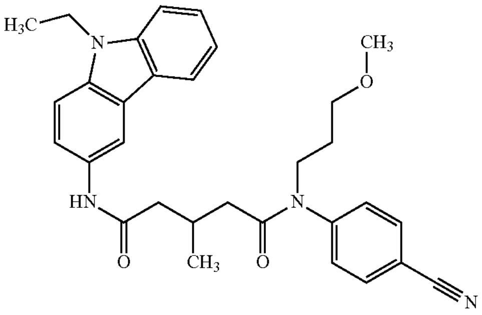 [SMILES: CCn1c2ccccc2c2cc(NC(=O)CC(C)CC(=O)N(CCCOC)c3ccc(C#N)cc3)ccc21] |
| salt | free | free | free |
|---|---|---|---|
| Example No. | 10 | 11 | 12 |
| structural formula | 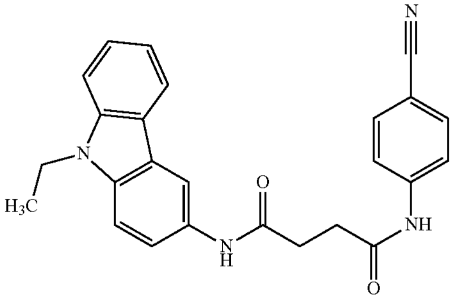 [SMILES: CCn1c2ccccc2c2cc(NC(=O)CCC(=O)Nc3ccc(C#N)cc3)ccc21] | 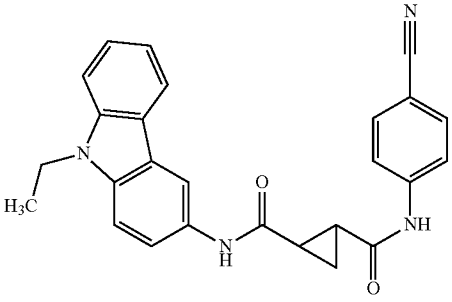 [SMILES: CCn1c2ccccc2c2cc(NC(=O)C3CC3C(=O)Nc3ccc(C#N)cc3)ccc21] | 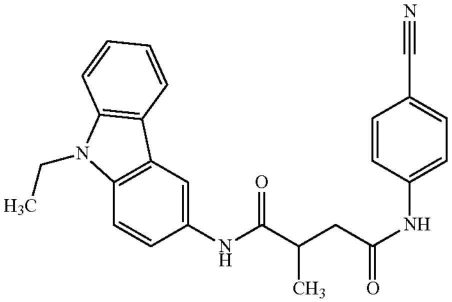 [SMILES: CCn1c2ccccc2c2cc(NC(=O)C(C)CC(=O)Nc3ccc(C#N)cc3)ccc21] |

TABLE 1-continued
| salt | free | free | free |
|---|---|---|---|
| Example No. | 13 | 14 | 15-step 1 |
| structural formula | 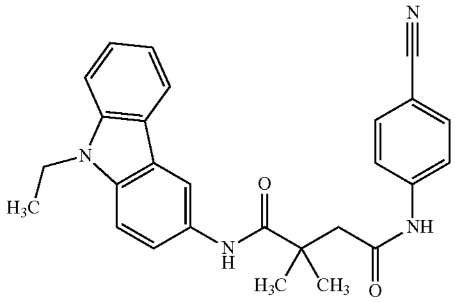 [SMILES: CCn1c2ccccc2c2cc(NC(=O)C(C)(C)CC(=O)Nc3ccc(C#N)cc3)ccc21] | 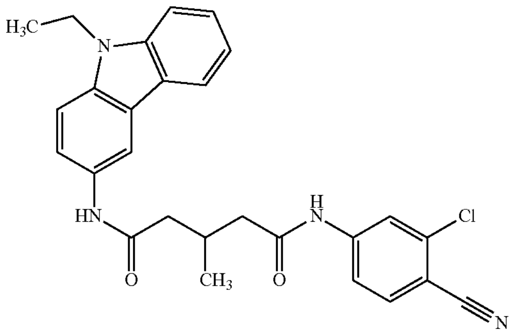 [SMILES: CCn1c2ccccc2c2cc(NC(=O)CC(C)CC(=O)Nc3ccc(C#N)c(Cl)c3)ccc21] | 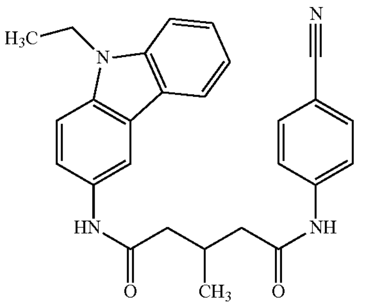 [SMILES: CCn1c2ccccc2c2cc(NC(=O)CC(C)CC(=O)Nc3ccc(C#N)cc3)ccc21] |
| salt | free | free | free |
| Example No. | 15 | 16 | 17 |
| structural formula | 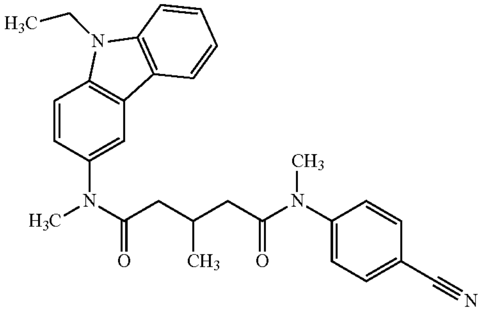 [SMILES: CCn1c2ccccc2c2cc(N(C)C(=O)CC(C)CC(=O)N(C)c3ccc(C#N)cc3)ccc21] | 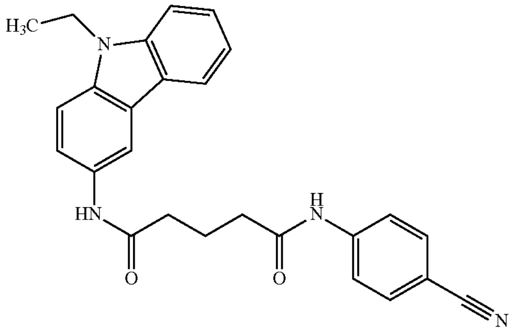 [SMILES: CCn1c2ccccc2c2cc(NC(=O)CCCC(=O)Nc3ccc(C#N)cc3)ccc21] | 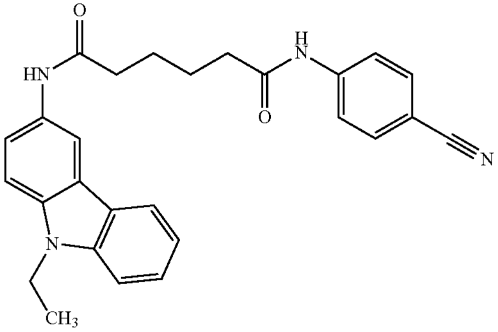 [SMILES: CCn1c2ccccc2c2cc(NC(=O)CCCCC(=O)Nc3ccc(C#N)cc3)ccc21] |

TABLE 1-continued
| salt | free | free | free |
|---|---|---|---|
| Example No. | 18 | 19 | 20 |
| structural formula | 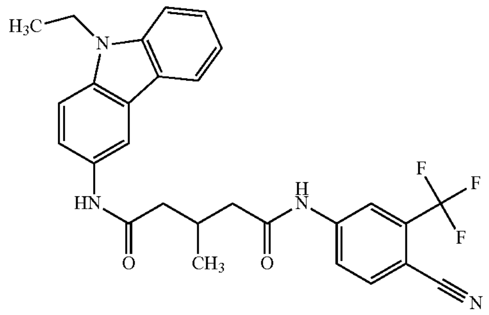 [SMILES: CCn1c2ccccc2c2cc(NC(=O)CC(C)CC(=O)Nc3ccc(C#N)c(C(F)(F)F)c3)ccc21] | 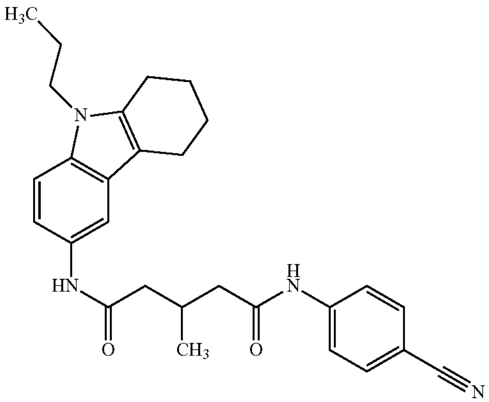 [SMILES: CCCn1c2c(c3cc(NC(=O)CC(C)CC(=O)Nc4ccc(C#N)cc4)ccc31)CCCC2] | 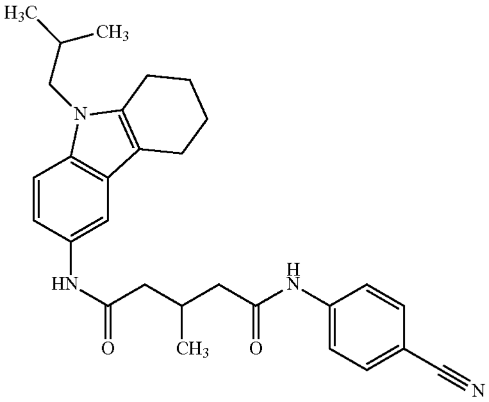 [SMILES: CC(C)Cn1c2c(c3cc(NC(=O)CC(C)CC(=O)Nc4ccc(C#N)cc4)ccc31)CCCC2] |
| salt | free | free | free |
|---|---|---|---|
| Example No. | 21 | 22 | 23 |
| structural formula | 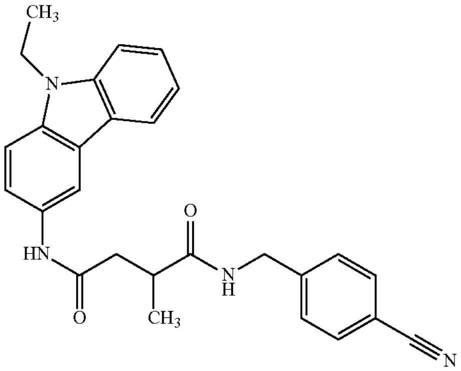 [SMILES: CCn1c2ccccc2c2cc(NC(=O)CC(C)C(=O)NCc3ccc(C#N)cc3)ccc21] | 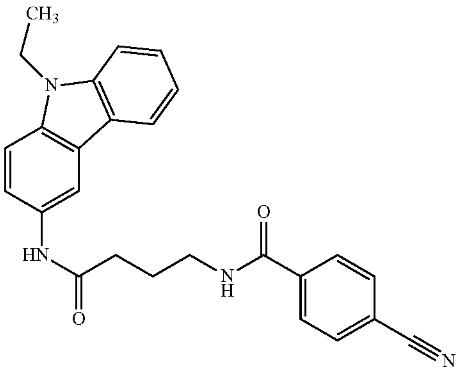 [SMILES: CCn1c2ccccc2c2cc(NC(=O)CCCNC(=O)c3ccc(C#N)cc3)ccc21] | 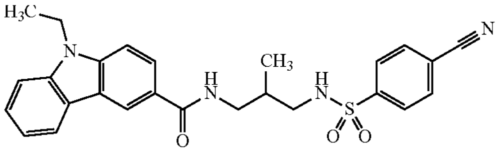 [SMILES: CCn1c2ccccc2c2cc(C(=O)NCC(C)CNS(=O)(=O)c3ccc(C#N)cc3)ccc21] |

TABLE 1-continued
| salt | free | free | free |
|---|---|---|---|
| Example No. | 24 | 25 | 26 |
| structural formula | 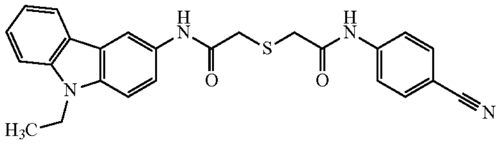 [SMILES: CCn1c2ccccc2c2cc(NC(=O)CSCC(=O)Nc3ccc(C#N)cc3)ccc21] | 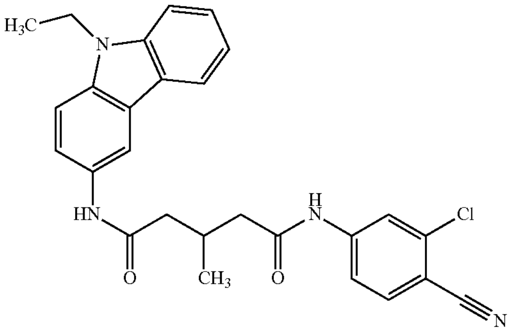 [SMILES: CCn1c2ccccc2c2cc(NC(=O)CC(C)CC(=O)Nc3ccc(C#N)c(Cl)c3)ccc21] | 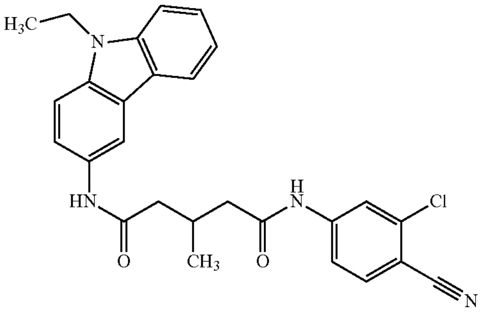 [SMILES: CCn1c2ccccc2c2cc(NC(=O)CC(C)CC(=O)Nc3ccc(C#N)c(Cl)c3)ccc21] |
| salt | free | free | free |
|---|---|---|---|
| Example No. | 27 | 28 | 29 |
| structural formula | 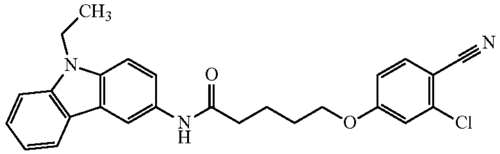 [SMILES: CCn1c2ccccc2c2cc(NC(=O)CCCCOc3ccc(C#N)c(Cl)c3)ccc21] | 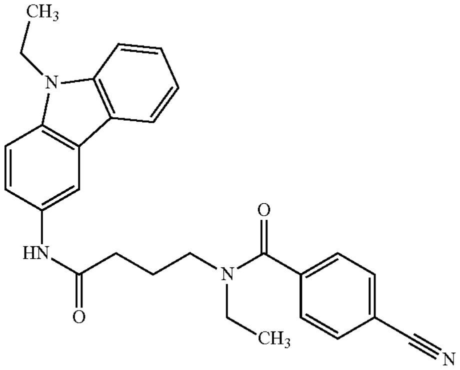 [SMILES: CCN(CCCC(=O)Nc1ccc2c(c1)c1ccccc1n2CC)C(=O)c1ccc(C#N)cc1] | 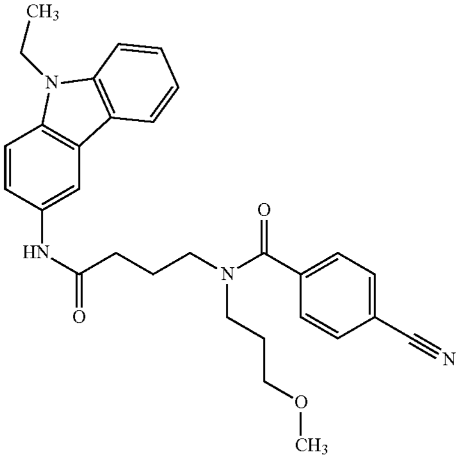 [SMILES: CCn1c2ccccc2c2cc(NC(=O)CCCN(CCCOC)C(=O)c3ccc(C#N)cc3)ccc21] |

TABLE 1-continued
| salt | free | free | free |
|---|---|---|---|
| Example No. | 30 | 31 | 32 |
| structural formula | 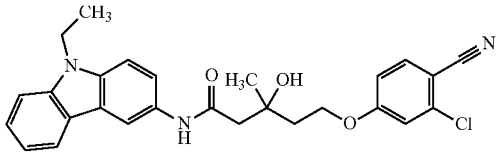 [SMILES: CCn1c2ccccc2c2cc(NC(=O)CC(C)(O)CCOc3ccc(C#N)c(Cl)c3)ccc21] | 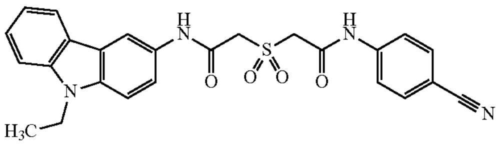 [SMILES: CCn1c2ccccc2c2cc(NC(=O)CS(=O)(=O)CC(=O)Nc3ccc(C#N)cc3)ccc21] | 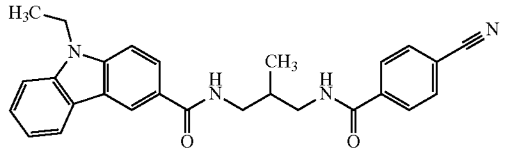 [SMILES: CCn1c2ccccc2c2cc(C(=O)NCC(C)CNC(=O)c3ccc(C#N)cc3)ccc21] |
| salt | free | free | free |
| Example No. | 33 | 34 | 35 |
| structural formula | 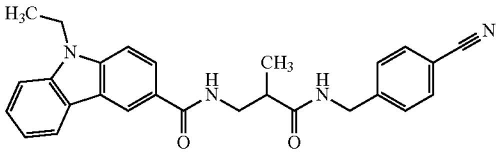 [SMILES: CCn1c2ccccc2c2cc(C(=O)NCC(C)C(=O)NCc3ccc(C#N)cc3)ccc21] | 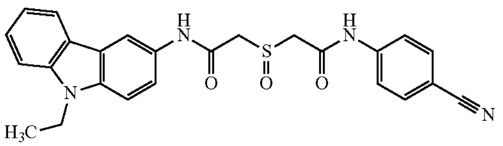 [SMILES: CCn1c2ccccc2c2cc(NC(=O)CS(=O)CC(=O)Nc3ccc(C#N)cc3)ccc21] | 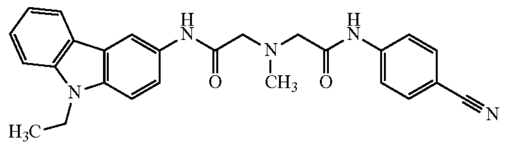 [SMILES: CCn1c2ccccc2c2cc(NC(=O)CN(C)CC(=O)Nc3ccc(C#N)cc3)ccc21] |
| salt | free | free | free |
| Example No. | 36 | 37 | 38 |
| structural formula | 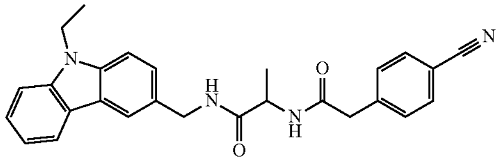 [SMILES: CCn1c2ccccc2c2cc(CNC(=O)C(C)NC(=O)Cc3ccc(C#N)cc3)ccc21] | 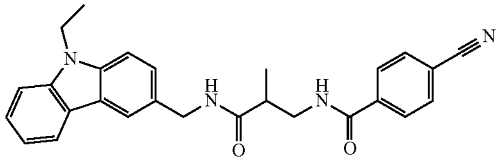 [SMILES: CCn1c2ccccc2c2cc(CNC(=O)C(C)CNC(=O)c3ccc(C#N)cc3)ccc21] | 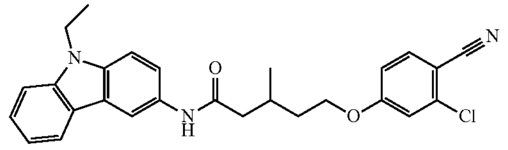 [SMILES: CCn1c2ccccc2c2cc(NC(=O)CC(C)CCOc3ccc(C#N)c(Cl)c3)ccc21] |

TABLE 1-continued
| | | | |
|---|---|---|---|
| salt | free | free | free |
| Example No. | 39 | 40 | 41 |
| structural formula | 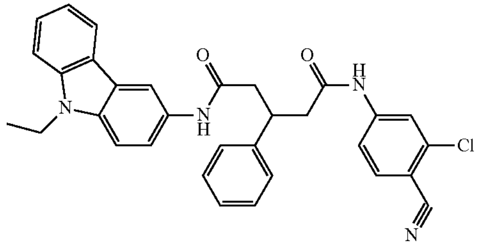 [SMILES: CCn1c2ccccc2c2cc(NC(=O)CC(CC(=O)Nc3ccc(C#N)c(Cl)c3)c3ccccc3)ccc21] | 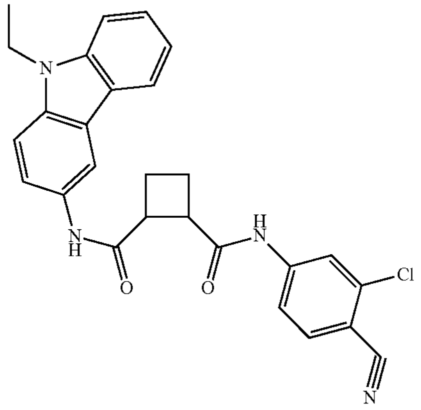 [SMILES: CCn1c2ccccc2c2cc(NC(=O)C3CCC3C(=O)Nc3ccc(C#N)c(Cl)c3)ccc21] | 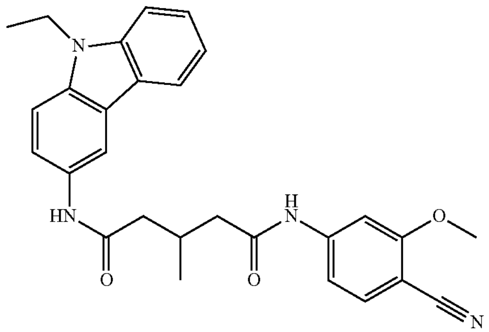 [SMILES: CCn1c2ccccc2c2cc(NC(=O)CC(C)CC(=O)Nc3ccc(C#N)c(OC)c3)ccc21] |
| salt | free | free | free |
| Example No. | 42 | 43 | 44 |
| structural formula | 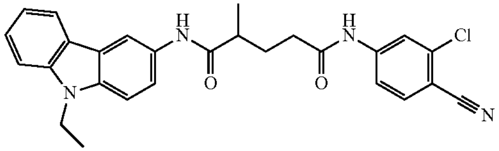 [SMILES: CCn1c2ccccc2c2cc(NC(=O)C(C)CCC(=O)Nc3ccc(C#N)c(Cl)c3)ccc21] | 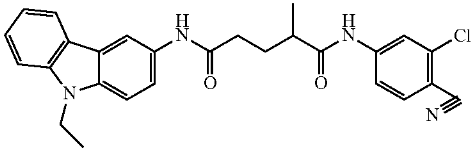 [SMILES: CCn1c2ccccc2c2cc(NC(=O)CCC(C)C(=O)Nc3ccc(C#N)c(Cl)c3)ccc21] | 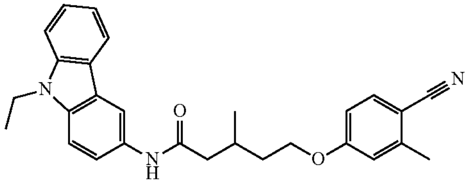 [SMILES: CCn1c2ccccc2c2cc(NC(=O)CC(C)CCOc3ccc(C#N)c(C)c3)ccc21] |
| salt | free | free | free |
| Example No. | 45 | 46 | 47 |
| structural formula | 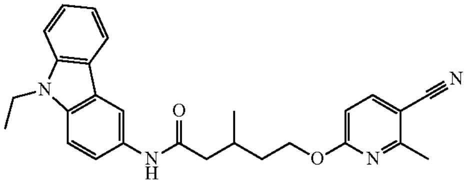 [SMILES: CCn1c2ccccc2c2cc(NC(=O)CC(C)CCOc3ccc(C#N)c(C)n3)ccc21] | 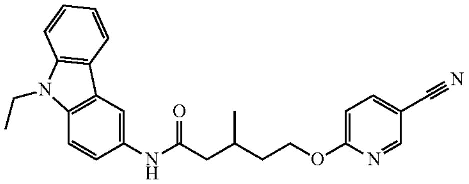 [SMILES: CCn1c2ccccc2c2cc(NC(=O)CC(C)CCOc3ccc(C#N)cn3)ccc21] | 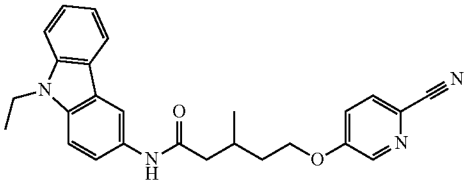 [SMILES: CCn1c2ccccc2c2cc(NC(=O)CC(C)CCOc3ccc(C#N)nc3)ccc21] |
| salt | free | free | free |

TABLE 1-continued
| | | | |
|---|---|---|---|
| Example No. | 48 | 49 | 50 |
| structural formula | 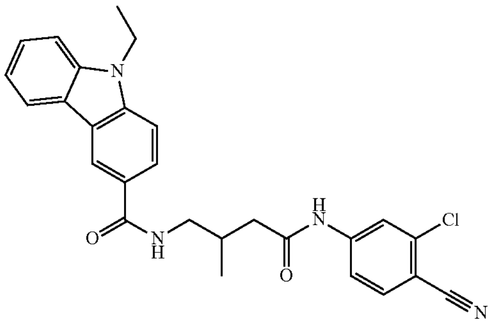 [SMILES: CCn1c2ccccc2c2cc(C(=O)NCC(C)CC(=O)Nc3ccc(C#N)c(Cl)c3)ccc21] | 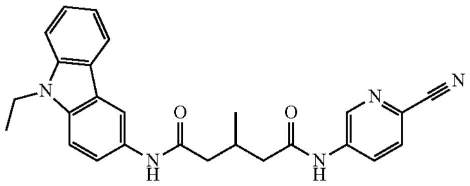 [SMILES: CCn1c2ccccc2c2cc(NC(=O)CC(C)CC(=O)Nc3ccc(C#N)nc3)ccc21] | 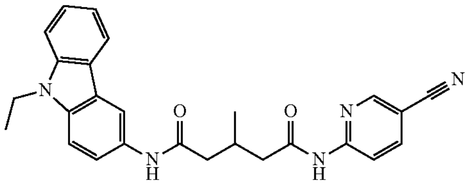 [SMILES: CCn1c2ccccc2c2cc(NC(=O)CC(C)CC(=O)Nc3ccc(C#N)cn3)ccc21] |
| salt | free | free | free |
| Example No. | 51 | 52 | 53 |
| structural formula | 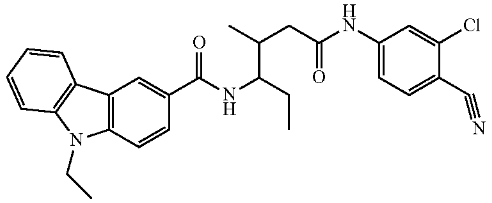 [SMILES: CCC(NC(=O)c1ccc2c(c1)c1ccccc1n2CC)C(C)CC(=O)Nc1ccc(C#N)c(Cl)c1] | 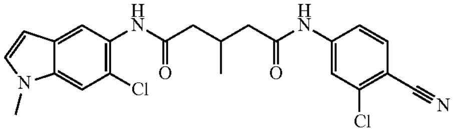 [SMILES: CC(CC(=O)Nc1ccc(C#N)c(Cl)c1)CC(=O)Nc1cc2ccn(C)c2cc1Cl] | 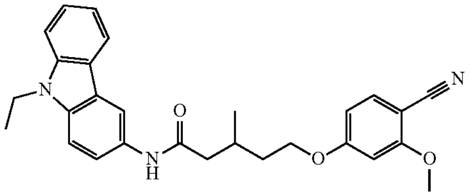 [SMILES: CCn1c2ccccc2c2cc(NC(=O)CC(C)CCOc3ccc(C#N)c(OC)c3)ccc21] |
| salt | free | free | free |
| Example No. | 54 | 55 | 56 |
| structural formula | 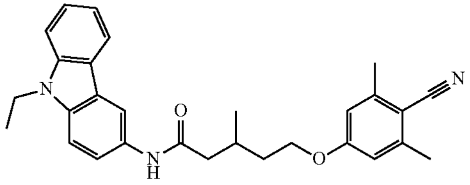 [SMILES: CCn1c2ccccc2c2cc(NC(=O)CC(C)CCOc3cc(C)c(C#N)c(C)c3)ccc21] | 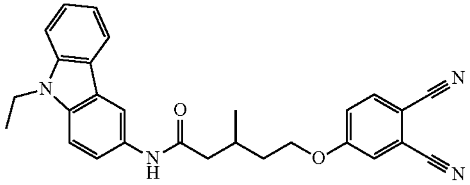 [SMILES: CCn1c2ccccc2c2cc(NC(=O)CC(C)CCOc3ccc(C#N)c(C#N)c3)ccc21] | 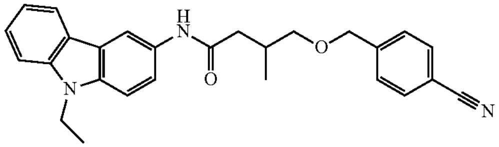 [SMILES: CCn1c2ccccc2c2cc(NC(=O)CC(C)COCc3ccc(C#N)cc3)ccc21] |
| salt | free | free | free |

Experimental Example 1

RORγt Binding Test

The binding activity of the test compound to RORγt was measured by a time resolved fluorescence resonance energy transfer method (TR-FRET) utilizing histidine-tagged RORγt, fluorescent-labeled cholesterol (BODIPY-cholesterol, AVIVA) and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 μL each. Then, RORγt diluted with an assay buffer to 240 nM was added by 3 μL each, after which fluorescent-labeled cholesterol diluted with the assay buffer to 12 μM was added by 3 μL each, and the mixture was stood at room temperature for 20 min. Thereafter, a terbium-labeled anti-histidine tag antibody diluted with the assay buffer to 8 nM was added by 3 μL each. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled cholesterol to RORγt at test compound 1 μM) measured by the above-mentioned method are shown in Table 2.

TABLE 2

| Test compound (Example No.) | binding inhibitory rate (%) |
|---|---|
| 3 | 88.2 |
| 4 | 99.4 |
| 14 | 101.0 |
| 16 | 97.8 |
| 18 | 87.2 |
| 19 | 98.9 |
| 20 | 98.7 |
| 24 | 98.9 |
| 25 | 101.0 |
| 26 | 99.7 |
| 30 | 94.4 |
| 34 | 94.6 |
| 38 | 91.9 |
| 39 | 91.4 |
| 40 | 96.3 |
| 41 | 93.4 |
| 42 | 101.0 |
| 43 | 100.0 |
| 44 | 62.9 |
| 48 | 104.0 |
| 49 | 93.9 |
| 50 | 88.8 |
| 55 | 82.2 |

Experimental Example 2

Cofactor Recruitment Test

Cofactor recruitment test was performed by Alpha Screen (Histidine Detection Kit, PerkinElmer) method. First, a test compound diluted with an assay buffer (50 mM Tris-HCl (pH 7.5), 50 mM KCl, 1 mM DTT, 0.1% BSA) was added to a 384 well plate by 5 μL each. Then, RORγt diluted with an assay buffer to 125 nM was added by 10 μL each, after which solutions of 25 nM biotinylated SRC-1 peptide (biotin-CLTARHKILHRLLQEGSPSD), 12.5 μg/mL acceptor beads and 12.5 μg/mL donor beads, which was prepared with the assay buffer, were added by 10 μL each. The mixture was stood in a dark place for 1 hr, and the signal value was measured by Envision (PerkinElmer).

The results (signal value inhibitory rate at test compound 1 μM) measured by the above-mentioned method are shown in Table 3.

TABLE 3

| Test compound (Example No.) | inhibitory rate (%) |
|---|---|
| 3 | 99.7 |
| 4 | 101.0 |
| 14 | 101.0 |
| 16 | 98.6 |
| 18 | 101.0 |
| 19 | 101.0 |
| 20 | 101.0 |
| 24 | 101.0 |
| 25 | 100.0 |
| 26 | 101.0 |
| 30 | 100.0 |
| 34 | 103.0 |
| 38 | 102.0 |
| 39 | 102.0 |
| 40 | 102.0 |
| 41 | 100.0 |
| 42 | 101.0 |
| 43 | 102.0 |
| 44 | 98.7 |
| 48 | 106.0 |
| 49 | 104.0 |
| 50 | 103.0 |
| 55 | 104.0 |

Experimental Example 3

Jurkat Reporter Test

The Jurkat cells used for the reporter test were cultured in a culture medium (RPMI (Invitrogen), 10% FCS (AusGeneX), 100 U/mL penicillin, 100 μg/mL streptomycin). On the day of the test, $4\times10^7$ cells were recovered by a centrifugal operation (1000 rpm, 5 min.) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector (53 μg) wherein a human IL-17 ROR response element was inserted into the upstream of luciferase of pGL 4.28 (Promega), and a vector (27 μg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 μg/mL streptomycin, 5 μM lovastatin), and plated in a 96 well plate by 90 μL each. A test compound diluted with the reaction medium was added by 10 μL each, and the cells were cultured overnight in an incubator. Bright-Glo (Promega) was added by 100 μL each, and the mixture was stirred at room temperature for 10 min, and the luminescence level was measured by Envision (PerkinElmer).

The results (luminescence level inhibitory rate at test compound 3 μM) measured by the above-mentioned method are shown in Table 4.

TABLE 4

| Test compound (Example No.) | inhibitory rate (%) |
|---|---|
| 3 | 82.6 |
| 4 | 103.0 |
| 14 | 103.0 |
| 16 | 100.0 |
| 18 | 100.0 |
| 19 | 103.0 |
| 20 | 102.0 |
| 24 | 100.0 |
| 25 | 103.0 |
| 26 | 102.0 |
| 30 | 92.5 |
| 34 | 82.7 |
| 38 | 99.4 |
| 39 | 93.2 |
| 40 | 99.3 |
| 41 | 96.4 |
| 42 | 104.0 |
| 43 | 104.0 |
| 44 | 77.8 |
| 48 | 115.0 |
| 49 | 109.0 |
| 50 | 110.0 |
| 55 | 102.0 |

Experimental Example 4

Mouse Th17 Cell Differentiation Test

CD4 positive naive T cells were collected from the spleen cells of BALB/c mice (female, 8-11w, Charles River Laboratories Japan, Inc.) using CD4+CD62L+ T Cell Isolation kit II (Miltenyi Biotec). The CD4 positive naive T cells in a 96 well plate ($3\times10^5$ cells/well) were stimulated (37° C. for culture) with anti-mouse CD3ε antibody (Bio X cell) (10 μg/mL, solid phase) and anti-CD28 antibody (Bio X cell) (5 μg/mL) for 4 days in the presence of anti-IFN-γ antibody (BioLegend), anti-IL-4 antibody (BioLegend), anti-IL-2 antibody (BioLegend), IL-6, TGF-β and IL-23 to differentiate into Th17 cells. The compound was dissolved in DMSO and then added thereto. The cells were cultured under these conditions for 4 days, and differentiation of the Th17 cells was evaluated by using the concentration of IL-17A, which was measured by ELISA, in the culture supernatant obtained by centrifugation.

The results (inhibitory rate at 10 μM of test compound) evaluated by the above-mentioned method are shown in Table 5.

TABLE 5

| Test compound (Example No.) | inhibitory rate (%) |
|---|---|
| 3 | 97.1 |
| 4 | 97.0 |
| 14 | 96.0 |
| Step 1 of Example 15 | 93.2 |
| 16 | 96.0 |
| 18 | 95.8 |
| 19 | 95.8 |
| 20 | 95.8 |
| 24 | 96.0 |
| 25 | 96.1 |
| 26 | 96.1 |
| 30 | 96.1 |
| 34 | 96.3 |
| 48 | 96.9 |

Experimental Example 5

Human Th17 Cell Differentiation Test

CD4 positive naive T cells were isolated from peripheral blood mononuclear cells (PBMC) collected from human peripheral blood by a density gradient centrifugation method. The CD4 positive naive T cells were seeded in a 96 well plate ($2\times10^4$ cells/well), and stimulated (37° C. for culture) with anti-CD 3/28Ab Dynabeads (Invitrogen) for 6 days in the presence of IL-1β, IL-6, IL-23, TGFβ, anti-IFNγ Ab (BioLegend) and anti-IL-4 Ab (BioLegend) to differentiate into Th17 cells. The compound was dissolved in DMSO and then added thereto. After culture for 6 days, the concentration of IL-17A in the culture supernatant obtained by centrifugation was measured by ELISA to evaluate differentiation of the Th17 cells.

The results (inhibitory rate at 10 μM of test compound) evaluated by the above-mentioned method are shown in Table 6.

TABLE 6

| Test compound (Example No.) | inhibitory rate (%) |
|---|---|
| 3 | 80.0 |
| 4 | 100.0 |
| 14 | 99.3 |
| 16 | 96.2 |
| 18 | 98.5 |
| 19 | 95.2 |
| 20 | 89.9 |
| 30 | 100.0 |

Experimental Example 6

IL17 Production Test in Human PBMC

Peripheral blood mononuclear cells (PBMC) collected from human peripheral blood by a density gradient centrifugation method were stimulated by Dynabeads (registered trade mark; anti-CD3/CD28 antibody) and cultured at 37° C. for 3 days. The compound was dissolved in DMSO and then added thereto. After culture for 3 days under such conditions, the concentration of IL-17A in the culture supernatant obtained by centrifugation was measured by ELISA to evaluate the effect of the compound on IL-17 production.

The results (inhibitory rate at 10 μM of test compound) evaluated by the above-mentioned method are shown in Table 7.

TABLE 7

| Test compound (Example No.) | inhibitory rate (%) |
|---|---|
| 3 | 73.3 |
| 4 | 88.3 |
| 14 | 95.0 |
| 16 | 91.0 |
| 18 | 96.0 |
| 19 | 87.0 |
| 20 | 84.0 |
| 30 | 100.0 |
| 48 | 97.6 |

Experimental Example 7

Effect on IL-17A Gene Expression Induced by Anti-CD3 Antibody Stimulation in Mouse Colon 1. Stimulation with Anti-CD3 Antibody and Collection of Colon Tissue An anti-CD3 antibody (5 μg/500 μL/mouse, BioXcell) or saline (500 μL/mouse) was intraperitoneally administered to Balb/c mice (female, 8 weeks old). Three hours after the administration, the mice were anesthetized by ether inhalation, and euthanized by cervical spine fracture dislocation. Then, the mice underwent laparotomy, and colons were isolated. The obtained colons were washed with saline, and then, immersed in RNA stabilization buffer (RNAlater, QIAGEN) at 4° C. for 18 hours or longer. Meanwhile, a suspension of a compound in 0.5% methylcellulose was orally administered an hour before administration of anti-CD3 antibody.

2. RNA Extraction from Colon Tissue and RT-PCR

The colon tissues were retrieved from RNAlater, and immediately immersed in 5 mL of RLT buffer (RNeasy Mini Kit, QIAGEN). Then, the tissues were homogenized at room temperature. Total RNA was extracted from the homogenized solution in accordance with the protocol of RNeasy Mini Kit (QIAGEN), and cDNA was prepared using high capacity RNA-to-cDNA Kit (Applied biosystems). mRNAs of various cytokines were detected by realtime-PCR (TaqMan PCR) using the obtained cDNA as a template. TaqMan universal master mixII (Applied biosystems) was used as PCR buffer, and TaqMan Gene Expression Assays (Applied biosystems): Mm00439619_m1 (IL-17A), Mm00801778 m1 (IFN-γ) and 43252341E (β-actin) were used for detection of each cytokine gene, respectively. The expression levels of each gene were shown as normalized values calculated using β-actin expression level.

3. Statistical Analysis

All the data were shown as mean values±SE. Statistical analyses were performed by Student's t test and William's test. It was found that there was a significant difference between two groups when P value is $P<0.05$ or $P<0.025$.

4. Result of Experiment

Figure 2:
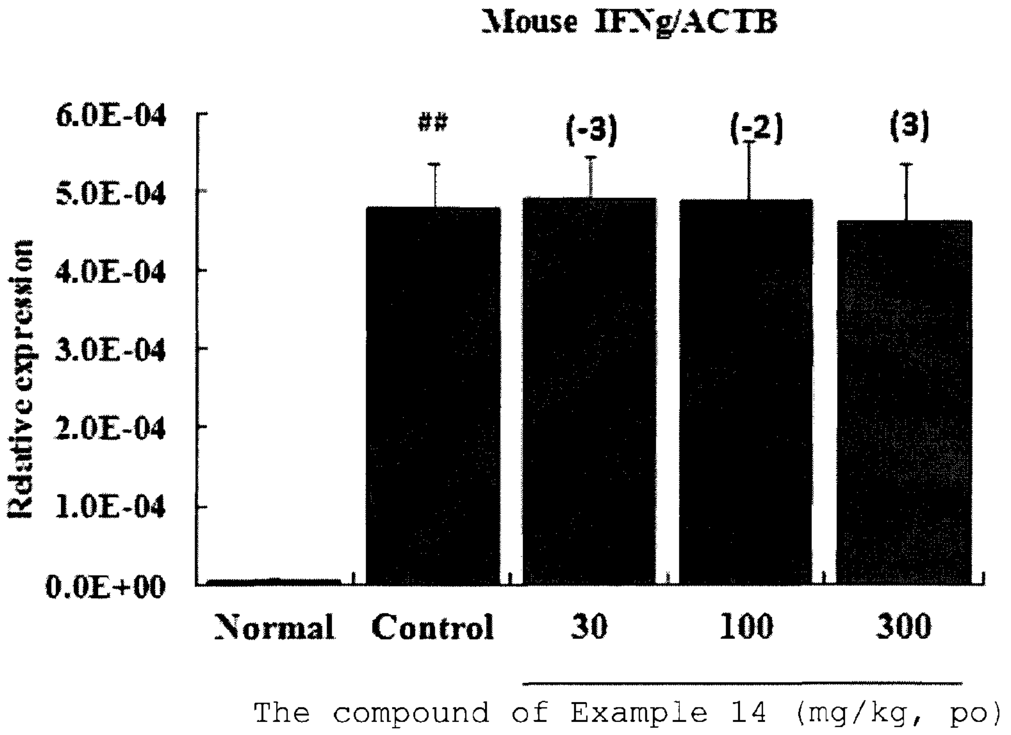
FIG. 2 shows an effect of the compound of Example 14 on IFN-γ gene expression caused by stimulation with anti-CD3 antibody in mouse colon.

It was confirmed that mRNA expressions of IL-17A and IFN-γ in colon tissue were significantly enhanced by intraperitoneally administering an anti-CD3 antibody to Balb/c mice, compared with the saline-administered group. Regarding these increases of expression, the compound of Example 14 (30, 100 and 300 mg/kg, po) significantly suppressed IL-17A expression in a dose-dependent manner, and the inhibition rates were 10, 25 and 53%, respectively (FIG. 1). On the other hand, it did not affect IFN-γ expression (FIG. 2).

Experimental Example 8

Effect on IL-17A Gene Expression in Lymph Node of EAE Rat Model

1. EAE (Experimental Allergic Encephalomyelitis) Sensitization

A killed *Mycobacterium tuberculosis*, H37Ra (DIFCO), was suspended at the concentration of 2 mg/mL in Freund Incomplete adjuvant (DIFCO), and 5 mg of MBP (Sigma) was dissolved in 1.25 mL of saline (Otsuka). These two solutions were mixed at the ratio of 1:1 using glass syringe with a three-way stopcock until emulsion was obtained. The emulsion was intracutaneously administered to the bottom of the right foot of Lewis rats (male, 7 weeks old) at 0.1 mL/rat.

2. Compound Administration

A suspension of the compound of Example 14 in 0.5% methylcellulose was orally administered twice a day from the day of sensitization at the dose of 30, 100 or 300 mg/kg. The last administration was performed on the 5$^{th}$ day after sensitization, and an autopsy was performed 4 hours after the last administration.

3. Analysis of IL-17A Expression

The autopsy was performed on the 5$^{th}$ day after the sensitization, and popliteal lymph nodes of the right leg were collected. The lymph nodes were immersed in RNA later (Applied Biosystems), stored at 4° C. overnight, and then, the lymph nodes were homogenized with a homogenizer in 1 mL of Isogen (Wako), and total RNA was purified. cDNA was synthesized by reverse transcription reaction using High Capacity cDNA Reverse Transcription Kit with RNase Inhibitor (Applied Biosystems). The synthesized cDNA was detected by PCR reaction using Taqman Gene Expression Master Mix (Applied Biosystems) and 7900HT Fast realtime PCR system (Applied Biosystems) (Stage 1: 50° C., 2 min, Stage 2: 95° C., 10 min, Stage 3: 95° C., 15 sec, 60° C., 1 min, 40 cycle). The primers and probes used in the reaction are as follows.

rat IL-17A:

```
Forward primer:
                                        (SEQ ID NO: 1)
5'-GCTCCAGAAGGCCCTCAGA-3'

Reverse primer:
                                        (SEQ ID NO: 2)
5'-GTCCTCATTGCGGCTCAGA-3'

Probe:
                                        (SEQ ID NO: 3)
5'-TACCTCAACCGTTCCACTTCACCCTGG-3'
```

rat GAPDH:

```
Forward primer:
                                        (SEQ ID NO: 4)
5'-GTGTTCCTACCCCCAATGTATCC-3'

Reverse primer:
                                        (SEQ ID NO: 5)
5'-GATGTCATCATACTTGGCAGGTTT-3'

Probe:
                                        (SEQ ID NO: 6)
5'-TTGTGGATCTGACATGCCGCCTG-3'
```

4. Result of Experiment

Figure 3:
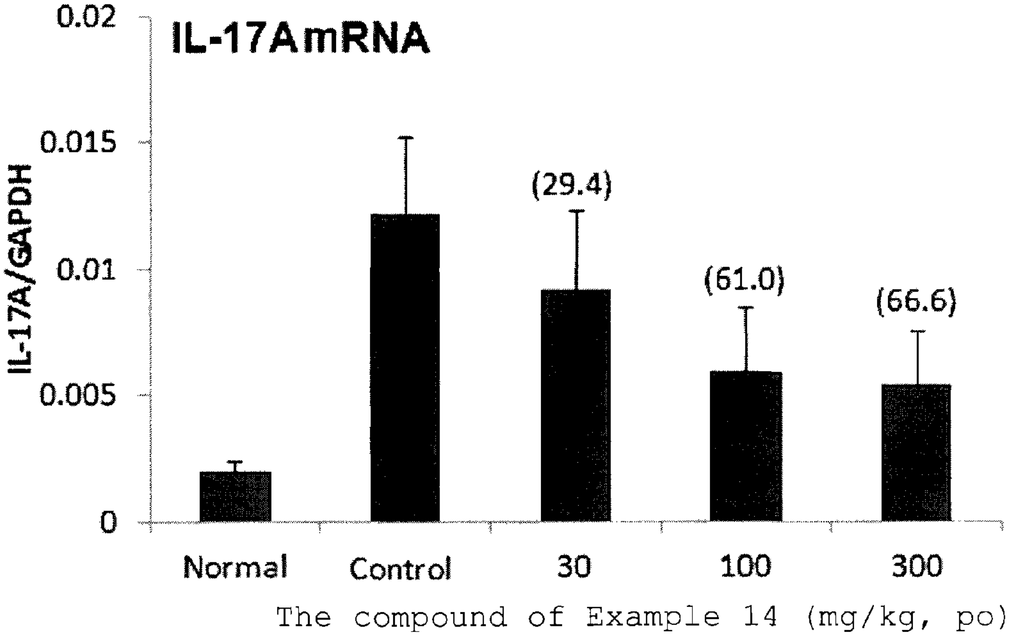
FIG. 3 shows an effect of the compound of Example 14 on IL-17A gene expression in lymph node of EAE rat model.

The compound of Example 14 (30, 100 and 300 mg/kg, po) tended to suppress the increase in IL-17A gene expression in lymph node of EAE-sensitized rat in a dose-dependent manner (FIG. 3).

INDUSTRIAL APPLICABILITY

The compound of the present invention has a superior RORγt inhibitory action, and useful as an agent for the prophylaxis or treatment of inflammatory bowel disease (IBD), ulcerative colitis (UC), Crohn's disease (CD), rheumatoid arthritis, multiple sclerosis, psoriasis and the like.

This application is based on patent application No. 207358/2011 filed in Japan, the contents of which are encompassed in full herein.

The invention claimed is:

1. A compound represented by the formula (I'):

(I')

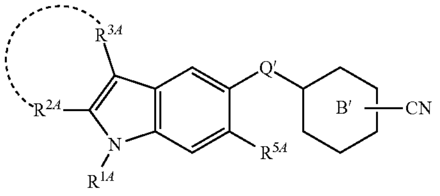

wherein $R^{1A}$ is an optionally substituted hydrocarbon group or an optionally substituted hydrocarbon-oxy group, $R^{2A}$ and $R^{3A}$ are each independently a hydrogen atom, an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^{2A}$ and $R^{3A}$ optionally form, together with the carbon atoms which they are bonded to, an optionally substituted hydrocarbon ring, $R^{5A}$ is a hydrogen atom or a halogen atom, Q' is a bivalent group selected from (I'a)

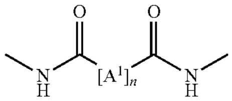

(I'b)

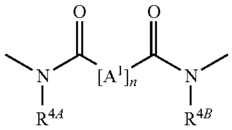

(I'c)

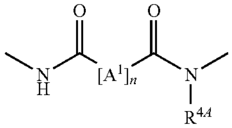

(I'd)

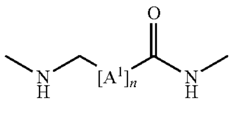

(I'e)

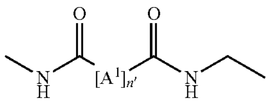

(I'f)

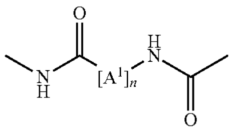

-continued (I'g)

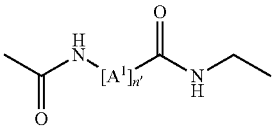

(I'h)

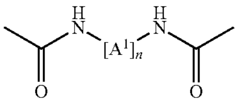

(I'i)

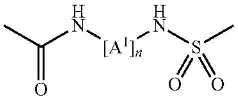

(I'j)

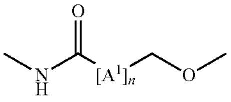

(I'k)

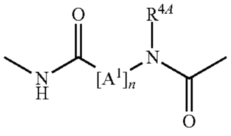

(I'l)

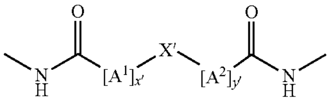

(I'm)

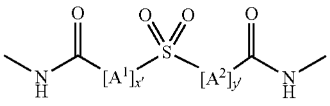

(I'n)

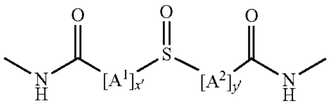

(I'o)

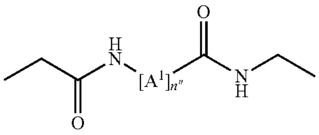

and (I'p)

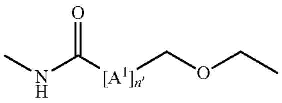

wherein $[A^1]$ are the same or different and each is a methylene group optionally substituted by substituent(s) selected from a hydroxy group, a phenyl group and an optionally substituted $C_{1-6}$ alkyl group, wherein the two substituents bonded to the single carbon atom are optionally combined to each other to form a hydrocarbon ring, and $[A^2]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in $[A^1]$ or $[A^2]$ is optionally combined to the substituent on the adjacent methylene group to form an optionally substituted hydrocarbon ring, $R^{4A}$ and $R^{4B}$ are the same or different and each is an optionally substituted hydrocarbon group, X' is an oxygen atom, a sulfur atom, or an imino group having an optionally substituted hydrocarbon group or a hydrogen atom, n is an integer of 1 to 5, n' is an integer of 1 to 4, n" is an integer of 1 to 3, and x' and y' are each 0 or natural number, and the sum is 0 to 4, and Ring B' is a benzene ring optionally having additional substituent(s), or a pyridine ring optionally having additional substituent(s), provided that when $R^{5A}$ is a halogen atom, then Ring B' is a benzene ring optionally having additional substituent(s), provided that 2-(2-((4-cyanophenyl)amino)-2-oxoethoxy)-N-(9-ethyl-9H-carbazol-3-yl)acetamide and N-(4-cyanophenyl)-N'-(9-ethyl-9H-carbazol-3-yl)-3-methylpentanediamide are excluded, or a salt thereof.

2. The compound or salt of claim 1, wherein $R^{5A}$ is a hydrogen atom, Q' is a bivalent group selected from (I'a)

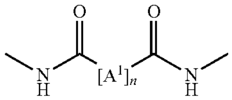

(I'b)

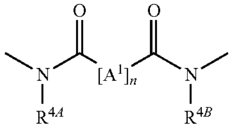

(I'c)

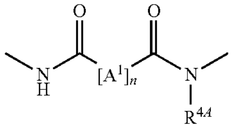

(I'd)

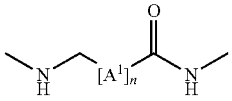

(I'e)

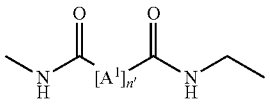

(I'f)

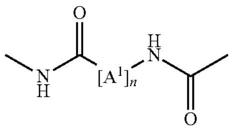

(I'g)

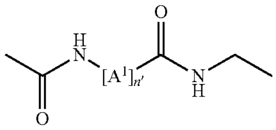

(I'h)

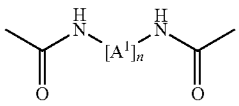

-continued (I'i)

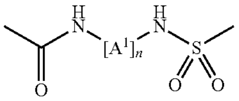

(I'j)

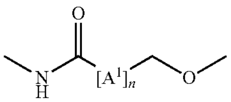

(I'k)

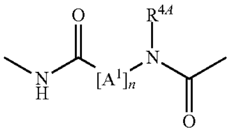

(I'l)

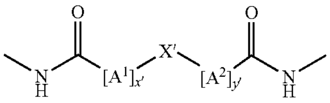

(I'm)

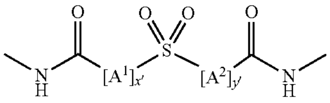

and (I'n)

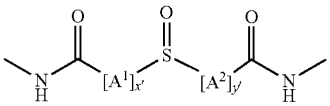

wherein $[A^1]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, and $[A^2]$ are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in $[A^1]$ or $[A^2]$ is optionally combined to the substituent on the adjacent methylene group to form an optionally substituted hydrocarbon ring, and the other symbols are as defined in claim 1, and Ring B' is a benzene ring optionally further substituted by substituent(s) excluding cyano.

3. The compound or salt of claim 1, wherein $R^{2A}$ and $R^{3A}$ are each independently a $C_{1-6}$ alkyl group, or $R^{2A}$ and $R^{3A}$ form, together with the carbon atoms which they are bonded to, an optionally substituted hydrocarbon ring.

4. The compound or salt of claim 1, wherein Q' is a bivalent group selected from (I'a)

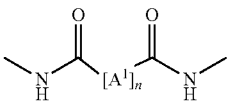

-continued (I'f)

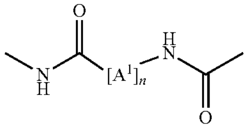

(I'j)

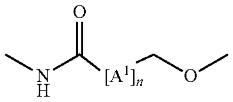

(I'l')

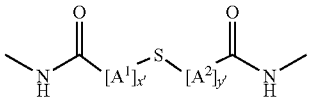

and (I'n)

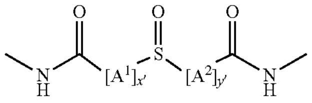

wherein each symbol is as defined in claim 1.

5. N-(4-Cyanophenyl)-N'-(9-ethyl-2,3,4,9-tetrahydro-1H-carbazol-6-yl)-3-methylpentanediamide or a salt thereof.

6. N-(3-Chloro-4-cyanophenyl)-N'-(9-ethyl-9H-carbazol-3-yl)-3-methylpentanediamide or a salt thereof.

7. N-{4-[(3-Chloro-4-cyanophenyl)amino]-2-methyl-4-oxobutyl}-9-ethyl-9H-carbazole-3-carboxamide or a salt thereof.

8. A medicament comprising a compound represented by the formula (I'):

(I')

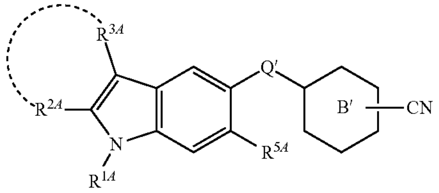

wherein $R^{1A}$ is an optionally substituted hydrocarbon group or an optionally substituted hydrocarbon-oxy group, $R^{2A}$ and $R^{3A}$ are each independently a hydrogen atom, an optionally substituted hydrocarbon group, an optionally substituted hydrocarbon-oxy group, an acyl group, a halogen atom, a cyano group, an optionally substituted hydrocarbon-amino group, an optionally substituted hydrocarbon-sulfanyl group, an optionally substituted hydrocarbon-sulfenyl group, an optionally substituted hydrocarbon-sulfonyl group or a nitro group, or $R^{2A}$ and $R^{3A}$ optionally form, together with the carbon atoms which they are bonded to, an optionally substituted hydrocarbon ring, $R^{5A}$ is a hydrogen atom or a halogen atom, Q' is a bivalent group selected from (I'a)

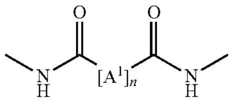

-continued (I'b)

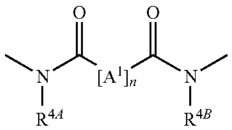

(I'c)

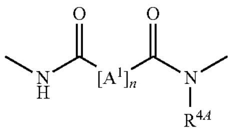

(I'd)

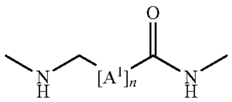

(I'e)

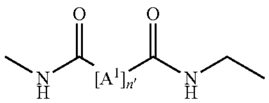

(I'f)

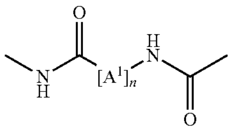

(I'g)

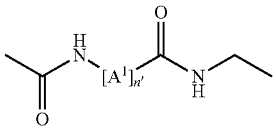

(I'h)

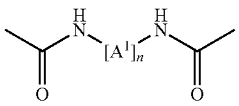

(I'i)

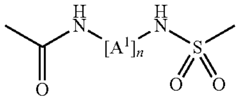

(I'j)

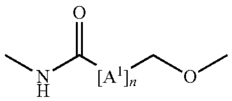

(I'k)

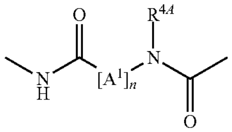

(I'l)

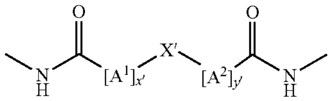

(I'm)

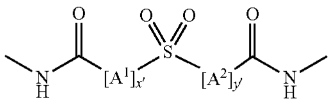

(I'n)

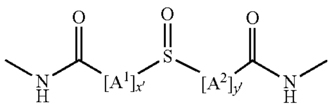

-continued (I'o)

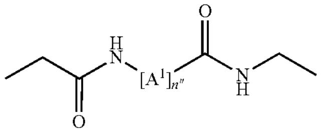

and (I'p)

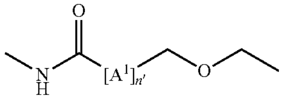

wherein

[$A^1$] are the same or different and each is a methylene group optionally substituted by substituent(s) selected from a hydroxy group, a phenyl group and an optionally substituted $C_{1-6}$ alkyl group, wherein the two substituents bonded to the single carbon atom are optionally combined to each other to form a hydrocarbon ring, and [$A^2$] are the same or different and each is a methylene group optionally substituted by substituent(s) selected from a hydroxy group and an optionally substituted $C_{1-6}$ alkyl group, wherein the two substituents bonded to the single carbon atom are optionally combined to each other to form a hydrocarbon ring, or the methylene group in [$A^1$] or [$A^2$] is optionally combined to the substituent on the adjacent methylene group to form an optionally substituted hydrocarbon ring, $R^{4A}$ and $R^{4B}$ are the same or different and each is an optionally substituted hydrocarbon group, X' is an oxygen atom, a sulfur atom, or an imino group having an optionally substituted hydrocarbon group or a hydrogen atom, n is an integer of 1 to 5, n' is an integer of 1 to 4, n" is an integer of 1 to 3, and x' and y' are each 0 or natural number, and the sum is 0 to 4, and Ring B' is a benzene ring optionally having additional substituent(s), or a pyridine ring optionally having additional substituent(s), provided that when $R^{5A}$ is a halogen atom, then Ring B' is a benzene ring optionally having additional substituent(s), or a salt thereof.

9. The medicament of claim 8, which is an RORγt inhibitor.

10. The medicament of claim 8, which is an agent for the treatment of inflammatory bowel disease (IBD), ulcerative colitis (UC), Crohn's disease (CD), rheumatoid arthritis, multiple sclerosis or psoriasis.

11. A method of inhibiting RORγt, which comprises administering an effective amount of the compound or salt of claim 1 to a mammal.

12. A method for the treatment of inflammatory bowel disease (IBD), ulcerative colitis (UC), Crohn's disease (CD), rheumatoid arthritis, multiple sclerosis or psoriasis, which comprises administering an effective amount of the compound or salt of claim 1 to a mammal.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: Forward primer for rat IL-17A

<400> SEQUENCE: 1

gctccagaag gccctcaga                                                   19


<210> SEQ ID NO 2
<211> LENGTH: 19
<212> TYPE: DNA
<213> ORGANISM: Artificial
<220> FEATURE:
<223> OTHER INFORMATION: Reverse primer for rat IL-17A

<400> SEQUENCE: 2

gtcctcattg cggctcaga                                                   19


<210> SEQ ID NO 3
<211> LENGTH: 27
<212> TYPE: DNA
<213> ORGANISM: Artificial
<220> FEATURE:
<223> OTHER INFORMATION: Probe for rat IL-17A

<400> SEQUENCE: 3

tacctcaacc gttccacttc accctgg                                          27


<210> SEQ ID NO 4
<211> LENGTH: 23
<212> TYPE: DNA
<213> ORGANISM: Artificial
<220> FEATURE:
<223> OTHER INFORMATION: Forward primer for rat GAPDH

<400> SEQUENCE: 4

gtgttcctac ccccaatgta tcc                                              23


<210> SEQ ID NO 5
<211> LENGTH: 24
<212> TYPE: DNA
<213> ORGANISM: Artificial
<220> FEATURE:
<223> OTHER INFORMATION: Reverse primer for rat GAPDH

<400> SEQUENCE: 5

gatgtcatca tacttggcag gttt                                             24


<210> SEQ ID NO 6
<211> LENGTH: 23
<212> TYPE: DNA
<213> ORGANISM: Artificial
<220> FEATURE:
<223> OTHER INFORMATION: Probe for rat GAPDH

<400> SEQUENCE: 6

ttgtggatct gacatgccgc ctg                                              23
```